US012340509B2

(12) United States Patent
Amundson et al.

(10) Patent No.: US 12,340,509 B2
(45) Date of Patent: *Jun. 24, 2025

(54) SYSTEMS AND METHODS FOR AUTOMATED DIGITAL IMAGE CONTENT EXTRACTION AND ANALYSIS

(71) Applicant: UnitedHealth Group Incorporated, Minnetonka, MN (US)

(72) Inventors: Russell H. Amundson, Merion Station, PA (US); Saurabh Bhargava, Eden Prairie, MN (US); Rama Krishna Singh, Greater Noida (IN); Ravi Pande, Noida (IN); Vishwakant Gupta, Noida (IN); Destiny L. Babjack, Bethel Park, PA (US); Gaurav Mantri, Gurugram (IN); Abhinav Agrawal, Gulabpura (IN); Sapeksh Suman, Greater Noida West (IN)

(73) Assignee: UnitedHealth Group Incorporated, Minnetonka, MN (US)

( * ) Notice: Subject to any disclaimer, the term of this patent is extended or adjusted under 35 U.S.C. 154(b) by 546 days.

This patent is subject to a terminal disclaimer.

(21) Appl. No.: 17/191,963

(22) Filed: Mar. 4, 2021

(65) Prior Publication Data

US 2021/0295504 A1    Sep. 23, 2021

Related U.S. Application Data

(63) Continuation of application No. 17/191,921, filed on Mar. 4, 2021, now Pat. No. 11,869,189.

(Continued)

(51) Int. Cl.
   *G06T 7/00*       (2017.01)
   *G06F 18/2137*    (2023.01)
   (Continued)

(52) U.S. Cl.
   CPC ...... *G06T 7/0014* (2013.01); *G06F 18/21375* (2023.01); *G06F 18/24* (2023.01);
   (Continued)

(58) Field of Classification Search
   CPC ......... G06T 7/0014; G06T 7/11; G06T 7/337; G06T 7/90; G06T 7/70; G06T 3/60;
   (Continued)

(56) References Cited

U.S. PATENT DOCUMENTS 4,688,780 A * 8/1987 Hanz .................. A61B 6/0421
                                                     5/601
8,548,828 B1    10/2013 Longmire
                (Continued)

OTHER PUBLICATIONS

"Eyelid Drooping—Blepharoptosis," RSIP Vision—Custom Medtech Imaging Algorithms, [article, online], (8 pages). [Retrieved from the Internet Jun. 7, 2021] <URL: https://www.rsipvision.com/eyelid-drooping-blepharoptosis/>.

(Continued)

*Primary Examiner* — Andrew W Bee
*Assistant Examiner* — Winta Gebreslassie
(74) *Attorney, Agent, or Firm* — Alston & Bird LLP

(57) ABSTRACT

Systems and methods are configured to extract images from provided source data files and to preprocess such images for content-based image analysis. An image analysis system applies one or more machine-learning based models for identifying specific features within analyzed images, and for determining one or more measurements based at least in part on the identified features. Such measurements may be embodied as absolute measurements for determining an absolute distance between features, or relative measurements for determining a relative relationship between fea- (Continued)

tures. The determined measurements are input into one or more machine-learning based models for determining a classification for the image.

22 Claims, 36 Drawing Sheets
(32 of 36 Drawing Sheet(s) Filed in Color)

Related U.S. Application Data

(60) Provisional application No. 62/991,686, filed on Mar. 19, 2020.

(51) Int. Cl.
| | | |
|---|---|---|
| *G06F 18/24* | (2023.01) | |
| *G06T 3/60* | (2024.01) | |
| *G06T 7/11* | (2017.01) | |
| *G06T 7/33* | (2017.01) | |
| *G06T 7/70* | (2017.01) | |
| *G06T 7/90* | (2017.01) | |
| *G06V 10/764* | (2022.01) | |
| *G06V 10/77* | (2022.01) | |
| *G16H 30/40* | (2018.01) | |
| *G16H 40/67* | (2018.01) | |

(52) U.S. Cl.
CPC .............. *G06T 3/60* (2013.01); *G06T 7/0012* (2013.01); *G06T 7/11* (2017.01); *G06T 7/337* (2017.01); *G06T 7/70* (2017.01); *G06T 7/90* (2017.01); *G06V 10/764* (2022.01); *G06V 10/7715* (2022.01); *G16H 30/40* (2018.01); *G16H 40/67* (2018.01); *G06T 2207/10024* (2013.01); *G06T 2207/20024* (2013.01); *G06T 2207/20081* (2013.01); *G06T 2207/20084* (2013.01); *G06T 2207/30004* (2013.01); *G06T 2207/30012* (2013.01); *G06T 2207/30068* (2013.01); *G06T 2207/30088* (2013.01); *G06T 2207/30096* (2013.01)

(58) Field of Classification Search
CPC ......... G06T 7/0012; G06T 2207/10024; G06T 2207/20024; G06T 2207/20081; G06T 2207/20084; G06T 2207/30004; G06T 2207/30012; G06T 2207/30068; G06T 2207/30088; G06T 2207/30096; G16H 40/67; G16H 30/40; G06V 10/7715; G06V 10/764; G06F 18/21375; G06F 18/24
See application file for complete search history.

(56) References Cited

U.S. PATENT DOCUMENTS

| | | |
|---|---|---|
| 8,898,798 B2 | 11/2014 | Rogers et al. |
| 8,954,339 B2 | 2/2015 | Schaffer |
| 10,242,443 B2 | 3/2019 | Hsieh et al. |
| 2014/0064583 A1* | 3/2014 | Wang ............... A61B 6/463 382/128 |
| 2014/0088989 A1 | 3/2014 | Krishnapuram et al. |
| 2017/0330320 A1 | 11/2017 | Lynch et al. |
| 2018/0040122 A1* | 2/2018 | Kang ................ A61B 6/504 |
| 2018/0060512 A1 | 3/2018 | Sorenson et al. |
| 2018/0342060 A1* | 11/2018 | Yao .................... G06F 3/167 |
| 2019/0138693 A1 | 5/2019 | Muller et al. |
| 2019/0392950 A1 | 12/2019 | Conroy |
| 2020/0004561 A1 | 1/2020 | Kottler et al. |
| 2020/0082507 A1 | 3/2020 | Fang et al. |
| 2020/0085546 A1 | 3/2020 | Li et al. |
| 2020/0258615 A1* | 8/2020 | Goshen ................. G06T 7/11 |
| 2021/0090694 A1 | 3/2021 | Colley et al. |
| 2021/0174503 A1* | 6/2021 | Trautwein ............ G16H 50/70 |
| 2022/0019771 A1* | 1/2022 | Matsunami .......... G06V 40/20 |
| 2022/0039774 A1* | 2/2022 | Wang ................ A61B 8/4472 |
| 2022/0284609 A1* | 9/2022 | Shree ................... G06T 7/33 |

OTHER PUBLICATIONS

"Pannus Is Not the Same Thing as Panniculus," Bariatric Pal, Apr. 22, 2014, (7 pages), [article, online]. [Retrieved from the Internet Jun. 7, 2021] <URL: https://www.bariatricpal.com/topic/305193-pannus-is-not-the-same-thing-as-panniculus/>.

"sovaSage—Reinventing Sleep Therapy," [online], (2 pages). [Retrieved from the Internet Jun. 7, 2021] <URL: https://www.sovasage.com/solution/>.

Borojeni, Azadeh A.T. et al. "Normative Ranges of Nasal Airflow Variables in Healthy Adults," International Journal of Computer Assisted Radiology and Surgery, Jan. 2020, vol. 15, No. 1, pp. 87-98. doi: 10.1007/s11548-019-02023-y. Epub: Jul. 2, 2019, PMID: 31267334; PMCID: PMC6939154.

Cress, C. Ray. "Panniculus-Pannus," JAMA the Journal of the American Medical Association, vol. 226, No. 3, p. 353, Oct. 15, 1973. doi: 10.1001/jama.1973.03230030065024.

Froomkin, A. Michael et al. "When Als Outperform Doctors: Confronting the Challenges of a Tort-Induced Over-Reliance on Machine Learning," University of Miami School of Law Institutional Repository, vol. 61 Ariz. L. Rev. 33, Feb. 20, 2019, (68 pages).

Notice of Allowance and Fees Due for U.S. Appl. No. 17/191,921, dated Aug. 22, 2023, (11 pages), United States Patent and Trademark Office, US.

Non-Final Rejection Mailed on Feb. 23, 2024 for U.S. Appl. No. 17/191,868, 9 page(s).

Notice of Allowance and Fees Due (PTOL-85) Mailed on Aug. 22, 2023 for U.S. Appl. No. 17/191,921, 11 page (s).

Notice of Allowance and Fees Due (PTOL-85) Mailed on Jun. 24, 2024 for U.S. Appl. No. 17/191,868, 10 page (s).

Notice of Allowance and Fees Due (PTOL-85) Mailed on Nov. 8, 2023 for U.S. Appl. No. 17/191,921, 2 page (s).

Notice of Allowance and Fees Due (PTOL-85) Mailed on Sep. 25, 2023 for U.S. Appl. No. 17/191,921, 2 page (s).

* cited by examiner

*Image credit: Medical Images / Image Source RF*

*Image credit: Medical Images / Shero*

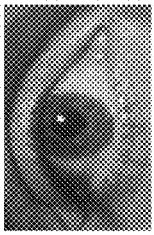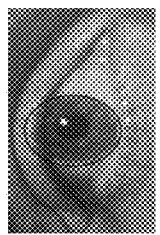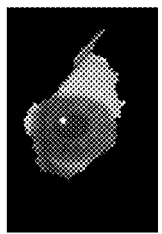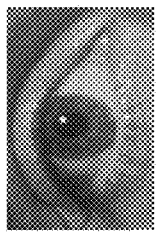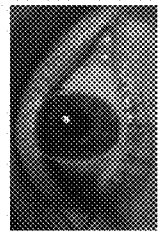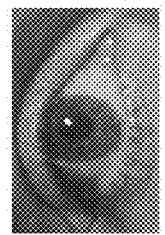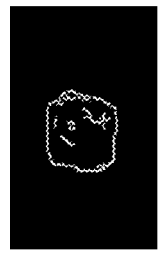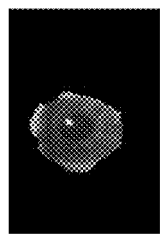
FIG. 11A  FIG. 11B  FIG. 11C  FIG. 11D  FIG. 11E
*Image credit: Medical Images / ISM / BARRAQUER, Barcelona*
FIG. 12A  FIG. 12B  FIG. 12C  FIG. 12D  FIG. 12E
*Image credit: Medical Images / ISM / BARRAQUER, Barcelona*
FIG. 13A  FIG. 13B  FIG. 13C  FIG. 13D  FIG. 13E
*Image credit: Medical Images / ISM / BARRAQUER, Barcelona*

*Image credit: Medical Images / ISM / BARRAQUER, Barcelona*

*Image credit: Medical Images / Shero*

Image credit: Medical Images / ISM / BARRAQUER, Barcelona

Image credit: Medical Images / ISM / BARRAQUER, Barcelona

Image credit: Medical Images / Shero

Image credit: Medical Images / Shero

*Image credit: Medical Images / Shero*

*Image credit: Medical Images / Shero*

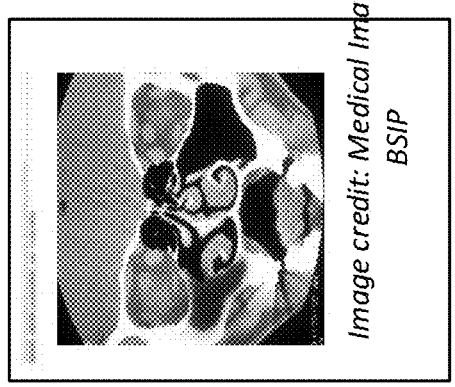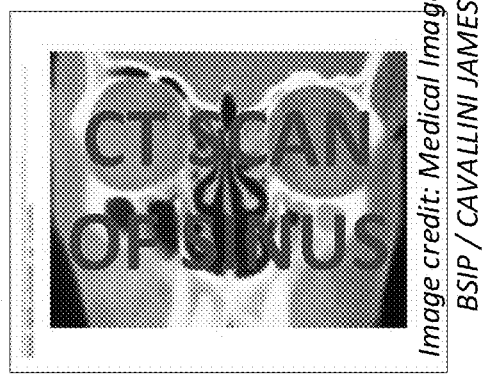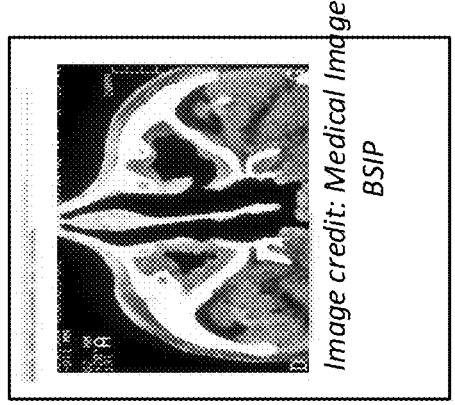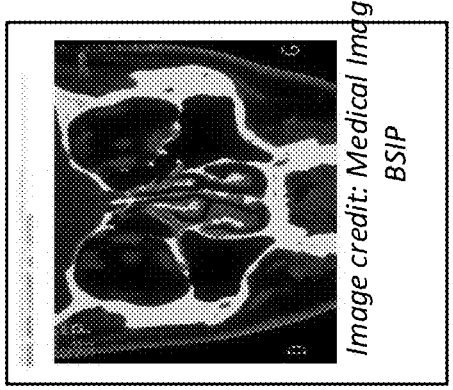
FIG. 19A

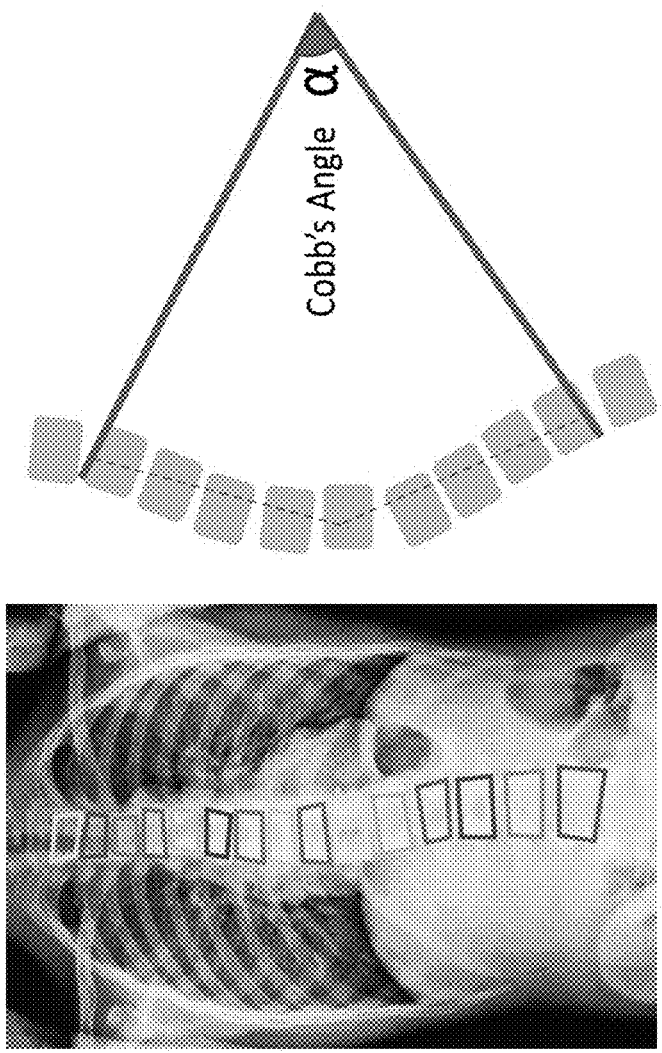
FIG. 20C
FIG. 20B
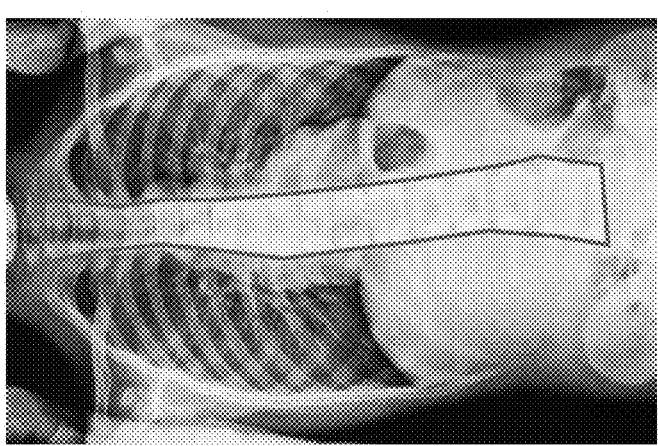
FIG. 20A

*Image credit: Adobe Stock Images*

*Image credit: Adobe Stock Images*

*Image credit: Adobe Stock Images*

*Image credit: Adobe Stock Images*

*Image credit: Medical Images / Allan Harris*

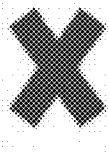
Back View
FIG. 31A
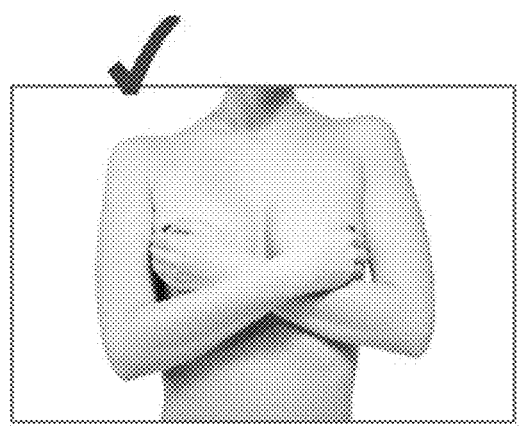
Front view – Shoulder Visible
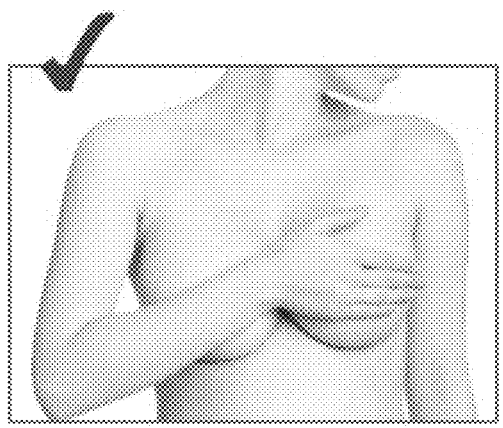
Front view – Shoulder visible
FIG. 31B

SYSTEMS AND METHODS FOR AUTOMATED DIGITAL IMAGE CONTENT EXTRACTION AND ANALYSIS

CROSS-REFERENCE TO RELATED APPLICATIONS

This patent application is a continuation of U.S. patent application Ser. No. 17/191,921, filed Mar. 4, 2021, which claims priority to U.S. Provisional Appl. Ser. No. 62/991,686 filed Mar. 19, 2020, which is incorporated herein by reference in its entirety.

This patent application is additionally related to co-pending U.S. patent application Ser. No. 17/191,868, filed Mar. 4, 2021, which is incorporated herein by reference in its entirety.

BACKGROUND

Exchanging information relating to certain topics is facilitated by the inclusion of images as support for (or in place of) textual descriptions of information to be exchanged. These visual images may be particularly helpful in providing complete descriptions of certain medical conditions through the use of photographs or other images generated through applicable imaging techniques (e.g., X-ray, Magnetic Resonance Imaging (MRI), CT-scan, and/or the like). However, generated images have historically been unsuitable for automated review via computer-implemented systems, such as for automated diagnoses of medical conditions reflected within those images. Accordingly, a need exists for systems and methods configured for automated review of images to establish objective image content and/or to perform automated analysis of the content of images.

BRIEF SUMMARY

Various embodiments are directed to computing system and methods configured for applying objective image content analysis processes so as to determine the presence (or absence) of objective image characteristics. Various embodiments receive data indicative of an intended analytical process to be applied to a particular image, and the image analysis system retrieves appropriate image analysis rules and models for performing the intended analytical process. The image analysis system then identifies reference features within the image for analysis, and utilizes those reference features to establish a scale and/or a point of reference to determine absolute or relative characteristics of various features identified within the image. Those characteristics may be compared against applicable objective criteria that may be utilized to perform an automated diagnosis and/or identification of characteristics of the image. The resulting diagnosis and/or identification of characteristics of the image may be utilized to select appropriate routing of the image (and/or an associated data file generated with the image). Appropriate reports may be made available via one or more tools based at least in part on the results of the image analysis.

Certain embodiments are directed to an image analysis system configured for identifying characteristics of features present within an image, the image analysis system comprising: one or more non-transitory memory storage areas; and one or more processors collectively configured to: receive image data comprising at least one embedded image; identify image analysis criteria stored within the non-transitory memory storage areas, wherein the image analysis criteria comprises at least one feature identification model and at least one scaling model; apply the at least one feature identification model to the at least one embedded image to identify a plurality of included features represented within the at least one embedded image, wherein the plurality of included features comprises at least one reference feature; apply the at least one scaling model, based at least in part on the at least one reference feature, to establish an absolute measurement scale for the at least one embedded image; measure, via the absolute measurement scale, a distance between locations within the at least one embedded image and associated with at least two of the plurality of included features; and determine, based at least in part on the image analysis criteria and the distance between the at least two of the plurality of included features, image characteristics for the image data.

In certain embodiments, the one or more processors are further configured to: generate a visual scale overlay based at least in part on the absolute measurement scale; and generate a display comprising the at least one embedded image overlaid with the visual scale overlay. In certain embodiments, the visual scale overlay comprises a visual grid having grid lines a defined absolute distance apart. In various embodiments, the visual scale overlay comprises one or more visual boundaries identifying boundaries of one or more of the plurality of included features. In certain embodiments, the one or more processors are further configured to: determine a transmission destination based at least in part on the image characteristics for the image data; and transmit the image data to the transmission destination. In various embodiments, the image data is received from a user computing entity; and wherein the one or more processors are further configured to transmit data comprising the image characteristics to the user computing entity. In certain embodiments, the one or more processors are further configured to: determine, based at least in part on application of the at least one feature identification model, whether at least one reference feature is present within the at least one embedded image; and upon determining that the at least one reference feature is not present within the at least one embedded image, transmit an error message to the user computing entity.

Various embodiments are directed to a computer-implemented method for identifying characteristics of features present within an image, the computer-implemented method comprising: receiving, via one or more processors, image data comprising at least one embedded image; identifying, via the one or more processors, image analysis criteria stored within the non-transitory memory storage areas, wherein the image analysis criteria comprises at least one feature identification model and at least one scaling model; applying, via the one or more processors, the at least one feature identification model to the at least one embedded image to identify a plurality of included features represented within the at least one embedded image, wherein the plurality of included features comprises at least one reference feature; applying, via the one or more processors, the at least one scaling model, based at least in part on the at least one reference feature, to establish an absolute measurement scale for the at least one embedded image; measuring, via the absolute measurement scale, a distance between locations within the at least one embedded image and associated with at least two of the plurality of included features; and determining, based at least in part on the image analysis criteria and the distance between the at least two of the plurality of included features, image characteristics for the image data.

In certain embodiments, the method further comprises generating a visual scale overlay based at least in part on the absolute measurement scale; and generating a display comprising the at least one embedded image overlaid with the visual scale overlay. In various embodiments, the visual scale overlay comprises a visual grid having grid lines a defined absolute distance apart. Moreover, in certain embodiments, the visual scale overlay comprises one or more visual boundaries identifying boundaries of one or more of the plurality of included features. In various embodiments, the method further comprises determining a transmission destination based at least in part on the image characteristics for the image data; and transmitting the image data to the transmission destination. In various embodiments, the image data is received from a user computing entity; and wherein the one or more processors are further configured to transmit data comprising the image characteristics to the user computing entity. In certain embodiments, the method further comprises determining, based at least in part on application of the at least one feature identification model, whether at least one reference feature is present within the at least one embedded image; and upon determining that the at least one reference feature is not present within the at least one embedded image, transmitting an error message to the user computing entity.

Certain embodiments are directed to a computer program product for identifying characteristics of features present within an image, the computer program product comprising at least one non-transitory computer-readable storage medium having computer-readable program code portions stored therein, the computer-readable program code portions configured to cause an executing processor to: receive image data comprising at least one embedded image; identify image analysis criteria stored within the non-transitory memory storage areas, wherein the image analysis criteria comprises at least one feature identification model and at least one scaling model; apply the at least one feature identification model to the at least one embedded image to identify a plurality of included features represented within the at least one embedded image, wherein the plurality of included features comprises at least one reference feature; apply the at least one scaling model, based at least in part on the at least one reference feature, to establish an absolute measurement scale for the at least one embedded image; measure, via the absolute measurement scale, a distance between locations within the at least one embedded image and associated with at least two of the plurality of included features; and determine, based at least in part on the image analysis criteria and the distance between the at least two of the plurality of included features, image characteristics for the image data.

In various embodiments, the computer program product further comprises one or more executable portions configured to: generate a visual scale overlay based at least in part on the absolute measurement scale; and generate a display comprising the at least one embedded image overlaid with the visual scale overlay. In certain embodiments, the visual scale overlay comprises a visual grid having grid lines a defined absolute distance apart. In various embodiments, the visual scale overlay comprises one or more visual boundaries identifying boundaries of one or more of the plurality of included features. In various embodiments, the computer program product further comprises one or more executable portions configured to: determining a transmission destination based at least in part on the image characteristics for the image data; and transmitting the image data to the transmission destination. In certain embodiments, the image data is received from a user computing entity; and wherein the one or more processors are further configured to transmit data comprising the image characteristics to the user computing entity. Moreover, certain embodiments comprise one or more executable portions configured to: determine, based at least in part on application of the at least one feature identification model, whether at least one reference feature is present within the at least one embedded image; and upon determining that the at least one reference feature is not present within the at least one embedded image, transmitting an error message to the user computing entity.

Certain embodiments are directed to an image analysis system configured for identifying characteristics of features present within an image, the image analysis system comprising: one or more non-transitory memory storage areas; and one or more processors collectively configured to: receive image data comprising at least one embedded image; identify image analysis criteria stored within the non-transitory memory storage areas, wherein the image analysis criteria comprises at least one feature identification model; apply the at least one feature identification model to the at least one embedded image to identify a plurality of included features represented within the embedded image; determine, based at least in part on the at least one feature identification model and the plurality of included features identified within the embedded images, feature characteristics of one or more of the plurality of included features; and determine, based at least in part on the image analysis criteria and the feature characteristics of the one or more of the plurality of included features, an image classification for the image data.

In certain embodiments, the one or more processors are further configured to: determine an orientation of each of the plurality of included features; determine a relative positioning between at least two of the plurality of included features; and determine, based at least in part on the image analysis criteria and the relative positioning between the at least two of the plurality of included features, the image classification for the image data. In various embodiments, determining a relative positioning between at least two of the plurality of included features comprises determining an angle of orientation between the at least two of the plurality of included features. In certain embodiments, determining a relative positioning between at least two of the plurality of included features comprises determining a relative distance between portions of each of the at least two of the plurality of included features, wherein the relative distance is a percentage of a size of one of the at least two of the plurality of included features. Moreover, in certain embodiments, the at least one feature identification model comprises a supervised machine-learning feature identification model configured to: identify a plurality of features represented within the embedded image; and classify one or more of the plurality of features represented within the embedded image; and wherein determining an image classification for the image data comprises determining image characteristics based at least in part on a classification of the one or more of the plurality of features represented within the embedded image. In certain embodiments, classifying the one or more of the plurality of features represented within the embedded image comprises classifying a skin lesion based at least in part on a convolutional neural network based feature identification model. Moreover, in various embodiments, classifying the one or more of the plurality of features represented within the embedded image comprises classifying a breast mass within a mammograph based at least in part on a convolutional neural network based feature identification model.

In certain embodiments, classifying the one or more of the plurality of features represented within the embedded image comprises determining a ratio between measurements of one or more vertebrae. In other embodiments, classifying the one or more of the plurality of features represented within the embedded image comprises comparing a location of a pubic symphysis relative to a detected lower edge of a hanging abdominal panniculus. In certain embodiments, classifying the one or more of the plurality of features represented within the embedded image comprises detecting an indention within a patient's shoulder. In various embodiments, classifying the one or more of the plurality of features represented within the embedded image comprises detecting a symmetry of a detected nose.

Certain embodiments are directed to a computer-implemented method for identifying characteristics of features present within an image, the computer-implemented method comprising: receiving, via one or more processors, image data comprising at least one embedded image; identifying, via the one or more processors, image analysis criteria stored within the non-transitory memory storage areas, wherein the image analysis criteria comprises at least one feature identification model; applying, via the one or more processors, the at least one feature identification model to the at least one embedded image to identify a plurality of included features represented within the embedded image; determining, based at least in part on the at least one feature identification model and the plurality of included features identified within the embedded images, feature characteristics of one or more of the plurality of included features; and determining, based at least in part on the image analysis criteria and the feature characteristics of the one or more of the plurality of included features, an image classification for the image data.

In certain embodiments, the method further comprises determining an orientation of each of the plurality of included features; determining a relative positioning between at least two of the plurality of included features; and determining, based at least in part on the image analysis criteria and the relative positioning between the at least two of the plurality of included features, the image classification for the image data. In various embodiments, determining a relative positioning between at least two of the plurality of included features comprises determining an angle of orientation between the at least two of the plurality of included features. In certain embodiments, determining a relative positioning between at least two of the plurality of included features comprises determining a relative distance between portions of each of the at least two of the plurality of included features, wherein the relative distance is a percentage of a size of one of the at least two of the plurality of included features. Moreover, in certain embodiments, the at least one feature identification model comprises a supervised machine-learning feature identification model configured to: identify a plurality of features represented within the embedded image; and classify one or more of the plurality of features represented within the embedded image; and wherein determining an image classification for the image data comprises determining image characteristics based at least in part on a classification of the one or more of the plurality of features represented within the embedded image. In certain embodiments, classifying the one or more of the plurality of features represented within the embedded image comprises classifying a skin lesion based at least in part on a convolutional neural network based feature identification model. In certain embodiments, classifying the one or more of the plurality of features represented within the embedded image comprises classifying a breast mass within a mammograph based at least in part on a convolutional neural network based feature identification model. In certain embodiments, classifying the one or more of the plurality of features represented within the embedded image comprises determining a ratio between measurements of one or more vertebrae. In other embodiments, classifying the one or more of the plurality of features represented within the embedded image comprises comparing a location of a pubic symphysis relative to a detected lower edge of a hanging abdominal panniculus. In certain embodiments, classifying the one or more of the plurality of features represented within the embedded image comprises detecting an indention within a patient's shoulder. In various embodiments, classifying the one or more of the plurality of features represented within the embedded image comprises detecting a symmetry of a detected nose.

Certain embodiments are directed to a computer program product for identifying characteristics of features present within an image, the computer program product comprising at least one non-transitory computer-readable storage medium having computer-readable program code portions stored therein, the computer-readable program code portions configured to cause an executing processor to: receive image data comprising at least one embedded image; identify image analysis criteria stored within the non-transitory memory storage areas, wherein the image analysis criteria comprises at least one feature identification model; apply the at least one feature identification model to the at least one embedded image to identify a plurality of included features represented within the embedded image; determine, based at least in part on the at least one feature identification model and the plurality of included features identified within the embedded images, feature characteristics of one or more of the plurality of included features; and determine, based at least in part on the image analysis criteria and the feature characteristics of the one or more of the plurality of included features, an image classification for the image data.

In certain embodiments, the executable portions are further configured to cause an executing processor to: determine an orientation of each of the plurality of included features; determine a relative positioning between at least two of the plurality of included features; and determine, based at least in part on the image analysis criteria and the relative positioning between the at least two of the plurality of included features, the image classification for the image data. In various embodiments, determining a relative positioning between at least two of the plurality of included features comprises determining an angle of orientation between the at least two of the plurality of included features. In certain embodiments, determining a relative positioning between at least two of the plurality of included features comprises determining a relative distance between portions of each of the at least two of the plurality of included features, wherein the relative distance is a percentage of a size of one of the at least two of the plurality of included features. Moreover, in certain embodiments, the at least one feature identification model comprises a supervised machine-learning feature identification model configured to: identify a plurality of features represented within the embedded image; and classify one or more of the plurality of features represented within the embedded image; and wherein determining an image classification for the image data comprises determining image characteristics based at least in part on a classification of the one or more of the plurality of features represented within the embedded image. In certain embodiments, classifying the one or more of the plurality of features represented within the embedded image comprises classifying a skin lesion based at least in part on a convolutional neural network based feature identification model. In certain embodiments, classifying the one or more of the plurality of features represented within the embedded image comprises classifying a breast mass within a mammograph based at least in part on a convolutional neural network based feature identification model.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Reference will now be made to the accompanying drawings, which are not necessarily drawn to scale, and wherein:

FIGS. 11A-13E are example images illustrating various processes for detecting sub-features in accordance with certain embodiments;

FIGS. 19A-19E are example images illustrating processes for extraction and analysis of sinusitis images in accordance with certain embodiments;

FIGS. 20A-21C are example images illustrating processes for extraction and analysis of scoliosis images in accordance with certain embodiments;

FIGS. 31A-32B illustrate example frontal torso images indicating filters for classifying images relating to breast surgery according to certain embodiments.

DETAILED DESCRIPTION

Figure 1:
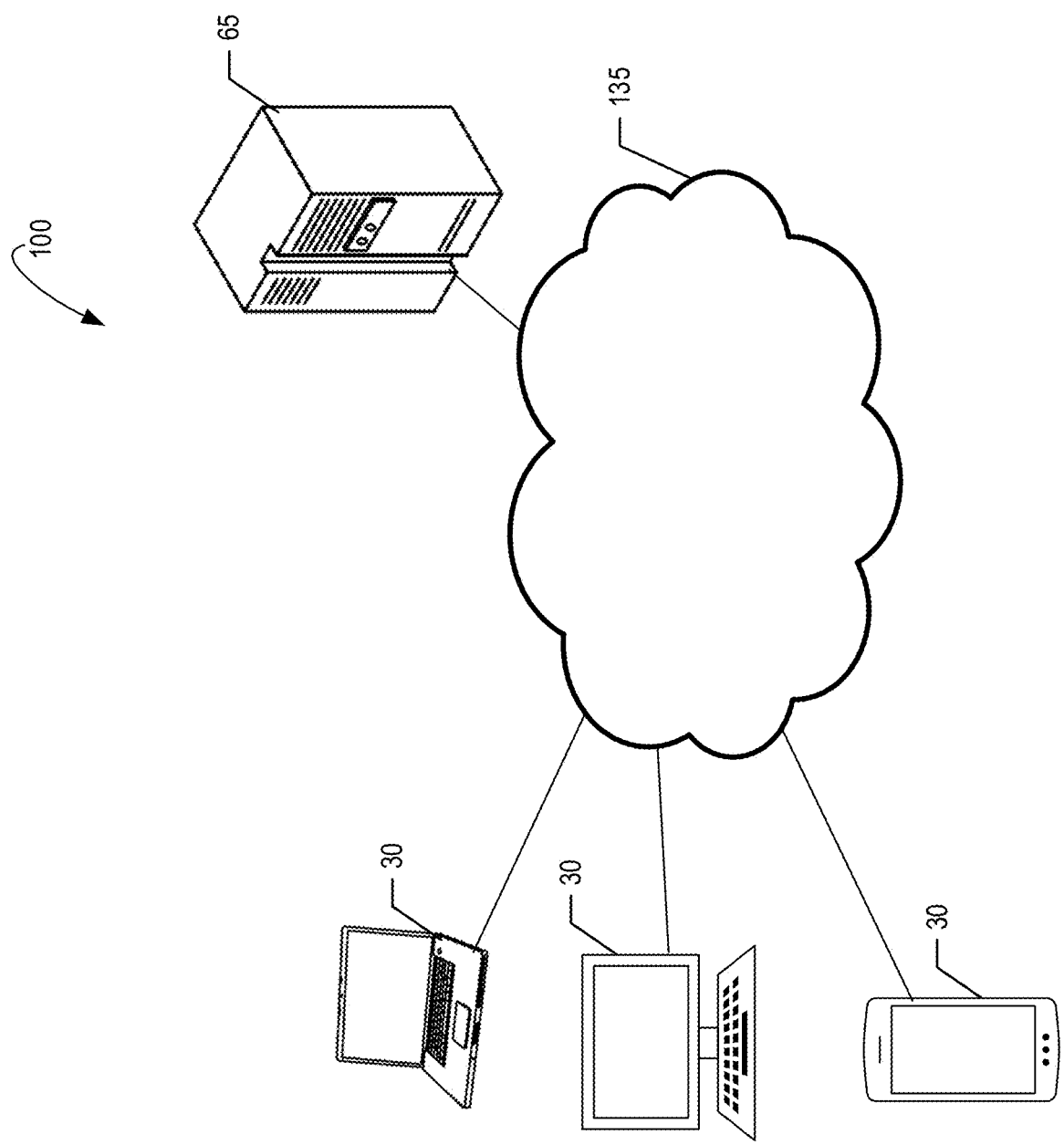
FIG. 1 is a diagram of a system that can be used in conjunction with various embodiments of the present invention.

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

I. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magneto resistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. EXEMPLARY SYSTEM ARCHITECTURE

FIG. 1 provides an illustration of a system 100 that can be used in conjunction with various embodiments of the present invention. As shown in FIG. 1, the system 100 may comprise one or more image analysis systems 65, one or more user computing entities 30 (e.g., which may encompass handheld computing devices, laptop computing devices, desktop computing devices, and/or one or more Internet of Things (IoT) devices, and/or the like, one or more networks 135, and/or the like. Each of the components of the system may be in electronic communication with, for example, one another over the same or different wireless or wired networks 135 including, for example, a wired or wireless Personal Area Network (PAN), Local Area Network (LAN), Metropolitan Area Network (MAN), Wide Area Network (WAN), and/or the like. Additionally, while FIG. 1 illustrate certain system entities as separate, standalone entities, the various embodiments are not limited to this particular architecture.

a. Exemplary Image Analysis System

Figure 2:
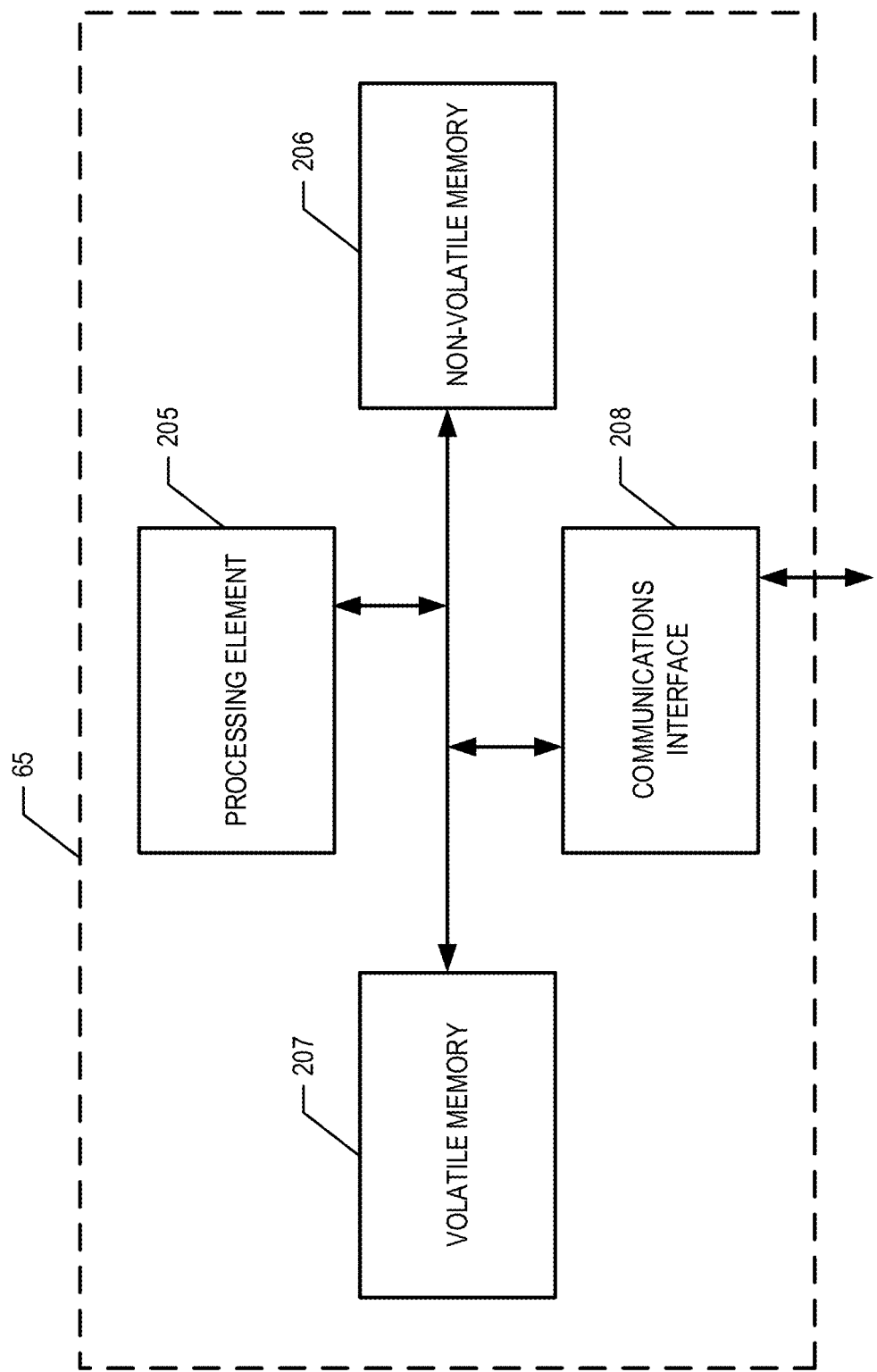
FIG. 2 is a schematic of an image analysis system in accordance with certain embodiments of the present invention.

FIG. 2 provides a schematic of an image analysis system 65 according to one embodiment of the present invention. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the image analysis system 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the image analysis system 65 may communicate with other computing entities, one or more user computing entities 30, and/or the like.

As shown in FIG. 2, in one embodiment, the image analysis system 65 may include or be in communication with one or more processing elements 205 (also referred to as processors, processing circuitry, and/or similar terms used herein interchangeably) that communicate with other elements within the image analysis system 65 via a bus, for example, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the image analysis system 65 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 206 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, metadata repositories database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to refer to a structured or unstructured collection of information/data that is stored in a computer-readable storage medium.

Memory media 206 (e.g., metadata repository) may also be embodied as a data storage device or devices, as a separate database server or servers, or as a combination of data storage devices and separate database servers. Further, in some embodiments, memory media 206 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third-party provider and where some or all of the information/data required for the operation of the system may be stored. As a person of ordinary skill in the art would recognize, the information/data required for the operation of the system may also be partially stored in the cloud data storage system and partially stored in a locally maintained data storage system.

Memory media 206 (e.g., metadata repository) may include information/data accessed and stored by the system to facilitate the operations of the system. More specifically, memory media 206 may encompass one or more data stores configured to store information/data usable in certain embodiments. For example, such data storage repositories may comprise stored data of one or more models utilized for identifying features and/or classifications of various images (e.g., training data utilized by one or more machine-learning models). Data stored within such data repositories may be utilized during operation of various embodiments as discussed herein.

In one embodiment, the image analysis system 65 may further include or be in communication with volatile media (also referred to as volatile storage, memory, memory storage, memory circuitry and/or similar terms used herein interchangeably). In one embodiment, the volatile storage or memory may also include one or more volatile storage or memory media 207 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205. Thus, the databases, database instances, database management system entities, data, applications, programs, program modules, scripts, source code, object code, byte code, compiled code, interpreted code, machine code, executable instructions, and/or the like may be used to control certain aspects of the operation of the image analysis system 65 with the assistance of the processing element 205 and operating system.

As indicated, in one embodiment, the image analysis system 65 may also include one or more network and/or communications interfaces 208 for communicating with various computing entities (e.g., user computing entities 30), such as by communicating data, content, information, and/or similar terms used herein interchangeably that can be transmitted, received, operated on, processed, displayed, stored, and/or the like. For instance, the image analysis system 65 may communicate with computing entities or communication interfaces of other computing entities, user computing entities 30, and/or the like. In this regard, the image analysis system 65 may access various data assets.

As indicated, in one embodiment, the image analysis system 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the image analysis system 65 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The image analysis system 65 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), Hypertext Markup Language (HTML), and/or the like.

As will be appreciated, one or more of the image analysis system's components may be located remotely from other image analysis system 65 components, such as in a distributed system. Furthermore, one or more of the components may be aggregated and additional components performing functions described herein may be included in the image analysis system 65. Thus, the image analysis system 65 can be adapted to accommodate a variety of needs and circumstances.

b. Exemplary User Computing Entity

Figure 3:
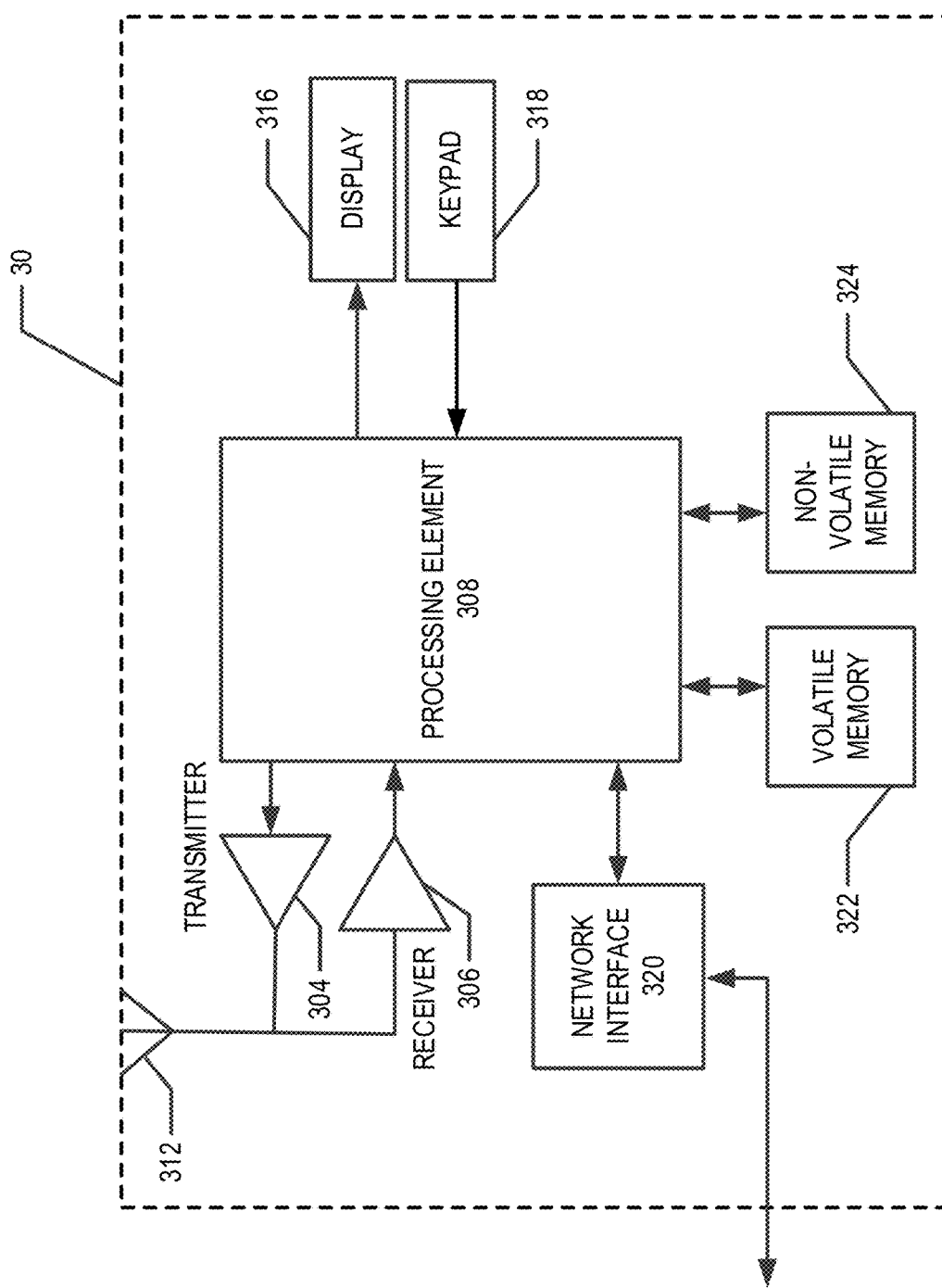
FIG. 3 is a schematic of a user computing entity in accordance with certain embodiments of the present invention.

FIG. 3 provides an illustrative schematic representative of user computing entity 30 that can be used in conjunction with embodiments of the present invention. As will be recognized, the user computing entity 30 may be operated by an agent and include components and features similar to those described in conjunction with the image analysis system 65. Further, as shown in FIG. 3, the user computing entity 30 may include additional components and features. For example, the user computing entity 30 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as a image analysis system 65, another user computing entity 30, and/or the like. In this regard, the user computing entity 30 may be capable of operating with one or more air interface standards, communication protocols, modulation types, and access types. More particularly, the user computing entity 30 may operate in accordance with any of a number of wireless communication standards and protocols. In a particular embodiment, the user computing entity 30 may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 30 can communicate with various other entities using concepts such as Unstructured Supplementary Service data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 30 can also download changes, add-ons, and updates, for instance, to its firmware, software (e.g., including executable instructions, applications, program modules), and operating system.

According to one embodiment, the user computing entity 30 may include location determining aspects, devices, modules, functionalities, and/or similar words used herein interchangeably. For example, the user computing entity 30 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data/data may be determined by triangulating the position in connection with a variety of other systems, including cellular towers, Wi-Fi access points, and/or the like. Similarly, the user computing entity 30 may include indoor positioning aspects, such as a location module adapted to acquire, for example, latitude, longitude, altitude, geocode, course, direction, heading, speed, time, date, and/ or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, Near Field Communication (NFC) transmitters, and/or the like. These indoor positioning aspects can be used in a variety of settings to determine the location of someone or something to within inches or centimeters.

The user computing entity 30 may also comprise one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, user interface, dashboard, webpage, and/or similar words used herein interchangeably executing on and/or accessible via the user computing entity 30 to cause display or audible presentation of information/data and for user interaction therewith via one or more user input interfaces. The user output interface may be updated dynamically from communication with the image analysis system 65. The user input interface can comprise any of a number of devices allowing the user computing entity 30 to receive information/data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 30 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 30 can collect information/data, user interaction/input, and/or the like.

The user computing entity 30 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entity 30.

c. Exemplary Networks

In one embodiment, the networks 135 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 135 may have any suitable communication range associated therewith and may include, for example, global networks (e.g., the Internet), MANs, WANs, LANs, or PANs. In addition, the networks 135 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

III. EXEMPLARY SYSTEM OPERATION

Details regarding various embodiments are described with respect to FIGS. 4-24 herein. As discussed herein, certain embodiments are configured to execute various image analysis processes to determine various characteristics of the substantive contents of an image, and to execute one or more processes selected based at least in part on the determined contents of the images.

a. Overview

Certain embodiments are configured for analysis of various images utilizing appropriately selected image analysis processes. Such image analysis processes may be selected automatically, based at least in part on the contents of an image to be analyzed, based on the contents of documents/reports containing the images to be analyzed, and/or the like. In certain embodiments, such image analysis processes may comprise machine-learning models configured for identifying features and/or sub-features reflected within images under analysis, and for utilizing those identified features and/or sub-features for determining various characteristics of the image. As just one non-limiting example, the image analysis system may be configured for identifying various features within an image, and for performing absolute and/or relative measurements (e.g., distance-based, angle-based, and/or the like) between multiple identified features and/or sub-features. In certain embodiments, the image analysis system may be configured to characterize one or more features identified within an image, for example, utilizing machine-learning based models for classifying the features identified within the images. In any event, based at least in part on the results of the analytical processes executed for the image, the image analysis system may be configured to provide appropriate results to a user computing entity supplying the image, and to perform various post-processing steps, such as routing the image to an approving user computing entity, selected based at least in part on the results of the analysis conducted for the image.

1. Technical Problem

Image analysis has historically required at least some amount of manual review to make objective and subjective determinations regarding the contents of those images. Particularly when reviewing images of multiple subjects having distinguishing features (e.g., photographing humans), structured rule-based analyses of those images may be difficult to automate in light of the distinguishing features present within each image. Moreover, the subject matter of individual images may have different perspectives, (e.g., slight variations in orientation of an imaging device versus the subject matter of the image), which may impact the ability to perform objective comparisons between the subject matter of an individual image and corresponding analytical requirements. Such inherent differences in image data contents inherently impede the use of automated systems and methods for analyzing contents of images.

2. Technical Solution

To address the inherently technical challenges associated with analyzing the content of individual images and/or other files containing one or more images, various embodiments utilize a structured series of analytical modules each utilizing rule-based and/or machine-learning based models to identify relevant features within an image, to establish appropriate scales, and/or reference points (e.g., based at least in part on the identified relevant features within the image), so as to enable objective determinations of various image characteristics.

b. Image Pre-Processing

Image analysis systems 65 in accordance with various embodiments operate together with an image pre-processing system (which may be a separate system or may execute as a part of the image analysis system 65 as discussed herein). In certain embodiments, the image pre-processing systems and/or methods may operate in accordance with the processes discussed within co-pending U.S. patent application Ser. No. 17/191,868, filed concurrently herewith, the contents of which are incorporated herein by reference in their entirety.

In certain embodiments, the image preprocessing methodologies comprise processes and/or corresponding modules for receiving a plurality of source data files. These source data files may be received from any of a variety of data sources, such as directly from individual user computing entities 30, from external systems (e.g., electronic health record systems operating to store medical notes received from individual care providers relating to individual patients, and/or the like). The image analysis system 65 may utilize any of a variety of mechanisms for intaking data files, such as application program interfaces (APIs) configured to identify a particular source data file, a file intake channel such as a File Transfer Protocol (FTP) system, a Cross File Transfer (CFT) system, SSH File Transfer Protocol (SFTP), an Enterprise Clinical Archive System (ECAS), a file upload system, an email system, via accessing file repositories (e.g., third party file repositories), a website in communication with the image analysis system, a locally stored application of a user computing entity managed by the image analysis system 65, and/or the like. Moreover, the image analysis system 65 may be configured for receiving source data files of a plurality of data file types, such as PDFs, image files (e.g., .jpg, .gif, .tiff, and/or the like), document files (e.g., .docx, .doc), spreadsheet files, webpage files, and/or the like. Such source data files may comprise clinical notes generated by a healthcare provider or other documents/reports (or other source data files) comprising both textual and image-based data.

In order to enable processing of any of the plurality of file types, the image analysis system 65 is configured to convert the received source data files into a standardized file type, such as an image file type. For multi-page source data files, each page may be separately converted to a separate standardized file type for individual analysis of each page of the source data file.

The image pre-processing may additionally comprise steps for identifying those standardized image files comprising embedded images of a sufficient size and/or quality for further analysis. Such identification process may proceed in accordance with a histogram color segmentation analysis analyzing each pixel within an image data file to determine color values associated therewith. These color values may be RGB color values or other color values that may be indicative of a shade or color of the pixel. Each pixel may then be classified as white (e.g., having a value of 255 for each of Red, Green, and Blue color channels), black (e.g., having a value of 0 for each of Red, Green, and Blue color channels), or other (e.g., pixels that are neither white nor black). The image analysis system 65 may utilize thresholds to differentiate between white, black, and other colors (e.g., those pixels having color values above a white threshold may be considered white; those pixels having color values below a black threshold may be considered black; and/or the like). It should be understood that other values for distinguishing between white, black, and other pixels may be utilized. Upon identifying color values for each pixel, the image analysis system 65 may be configured to generate a color profile for the image data file, indicating an overall percentage of white pixels, black pixels, and/or other pixels within the image data file. The image analysis system 65 may then compare the color profile for the image data file against one or more thresholds to identify those image data files comprising embedded images of suitable size for further analysis. For example, the image analysis system 65 may determine whether the image profile for an image data file indicates that the image data file comprises a percentage of black pixels greater than a threshold percentage (e.g., 75%) and/or a percentage of white pixels greater than a threshold percentage (e.g., 75%) to determine whether the image data file contains embedded images of suitable quality for further analysis. Further to the above example, if the image data file comprises more black pixels than the threshold amount or if the image data file comprises more white pixels than the threshold amount, the image data file may be determined to be unsuitable for further analysis. The image analysis system 65 may then flag those image data files as irrelevant for further analysis (e.g., by updating metadata associated with those image data files with a relevant flag; by discarding those image data files from the data storage directory; and/or the like).

Figure 5B:
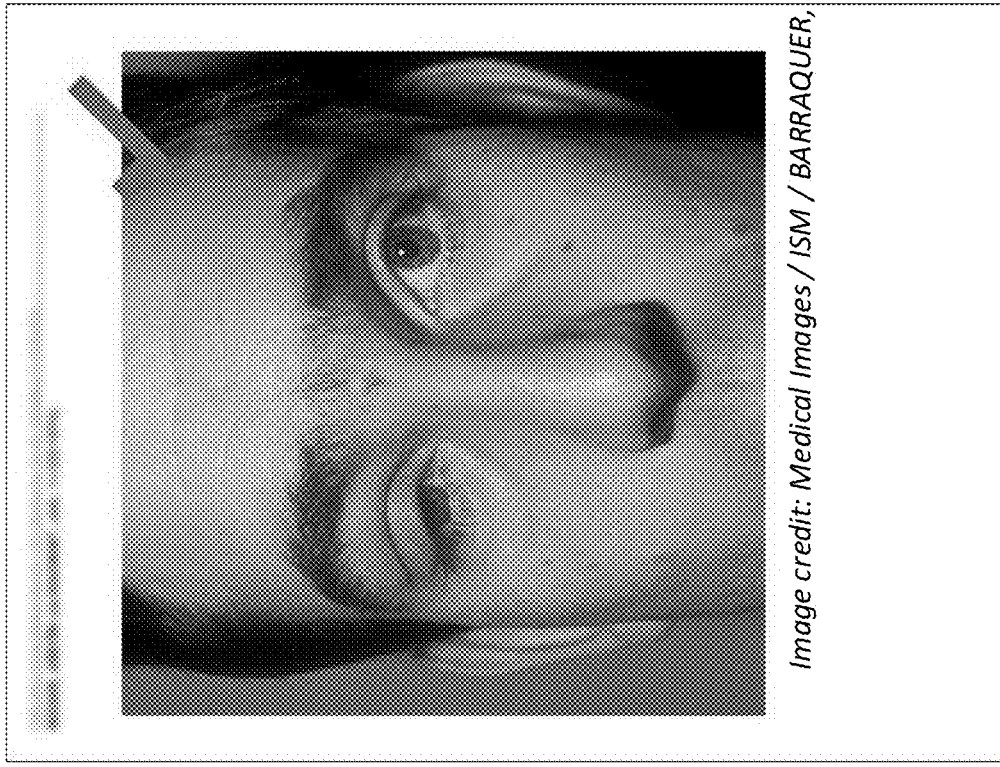
FIGS. 5A-5B are example images extracted from a source data file in accordance with certain embodiments.
Figure 5A:
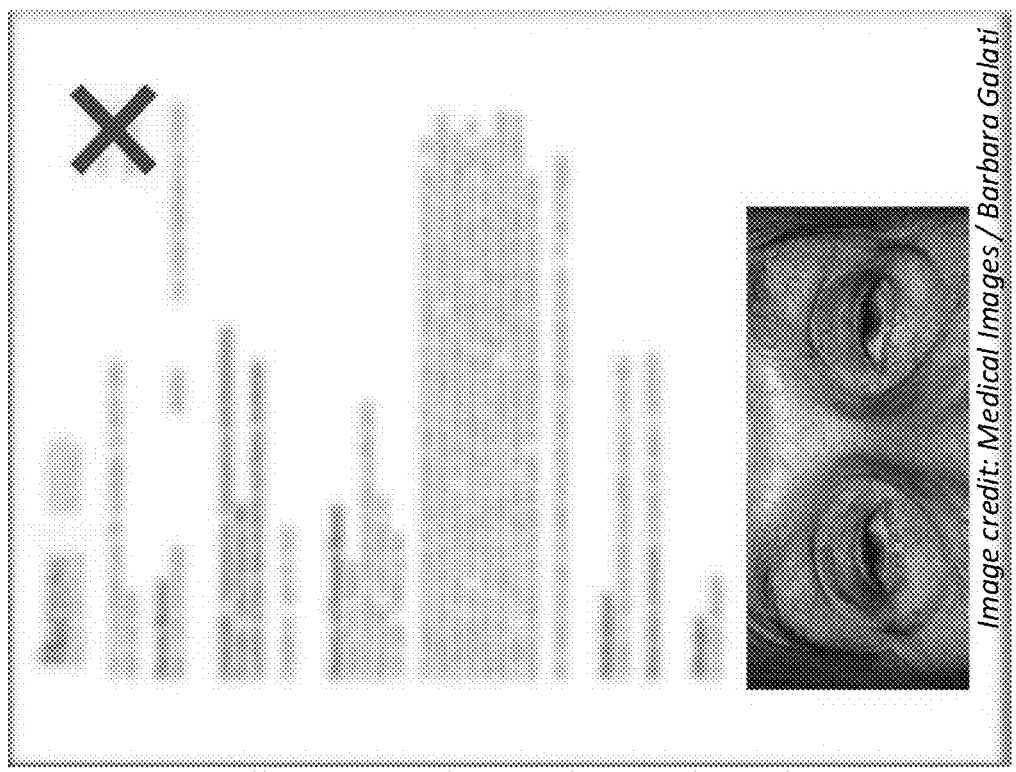

FIGS. 5A-5B illustrate differences between an image data file having an embedded image unsuitable for further analysis (FIG. 5A) and an image data file having an embedded image suitable for further analysis (FIG. 5B). Because the image data file of FIG. 5A has a high percentage of white pixels and a relatively small color photograph, the histogram color analysis determines that the number of white pixels exceeds a threshold value indicating the image data file is unsuitable for further analysis. By contrast, the image data file of FIG. 5B does not have a high percentage of white pixels or black pixels, as determined by a histogram color analysis, indicating that the image data file includes a color photograph of sufficient size for further analysis.

In certain embodiments, the image pre-processing steps may additionally determine whether identified embedded images are of a sufficient size for further analysis. The size of each embedded image may thus be identified (e.g., via image feature edge detection processes to identify the boundaries of each image), and the determined size of each image may be compared against a minimize image size (e.g., 400 pixels by 400 pixels). Those images having a size less than the threshold size may be discarded or otherwise excluded from further analysis.

Figure 6A:
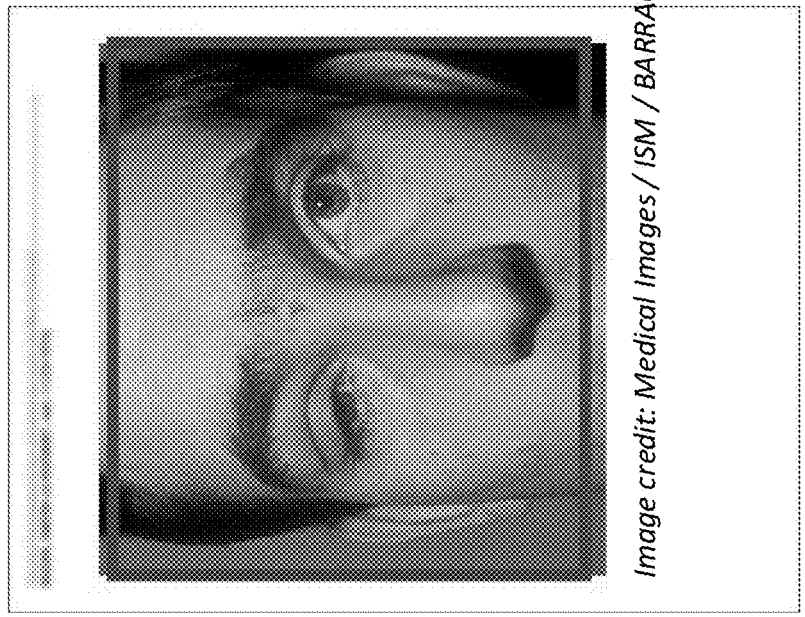
FIGS. 6A-6C are example images illustrating detection of feature orientation within such images in accordance with certain embodiments.
Figures 6B, 6C:
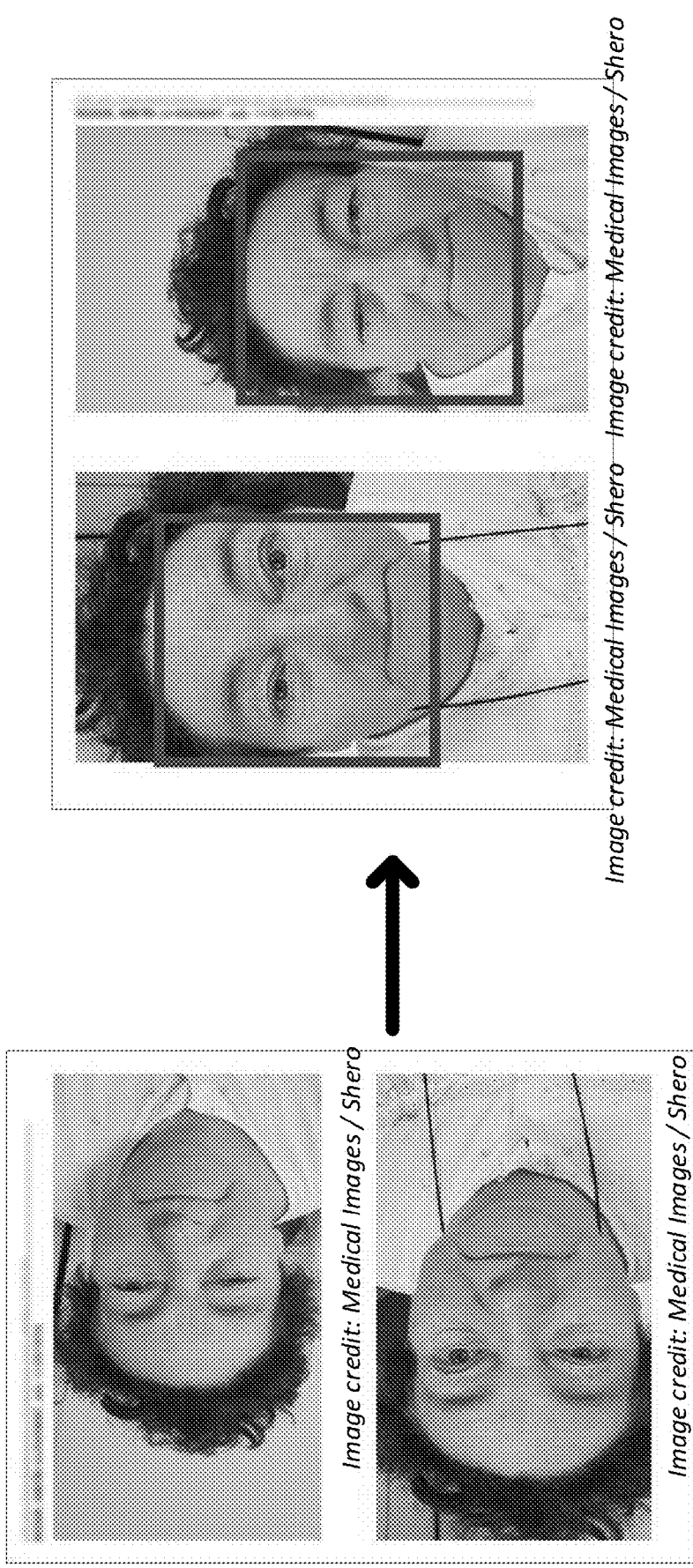

Moreover, as reflected in FIGS. 6A-6C, in certain embodiments the image pre-processing steps may additionally comprise detecting various features within an image to determine the orientation of the image. In certain embodiments, upon determining that the image orientation does not satisfy image analysis criteria, the image pre-processing steps may additionally comprise rotating the image to satisfy applicable image analysis criteria.

Figure 7B:
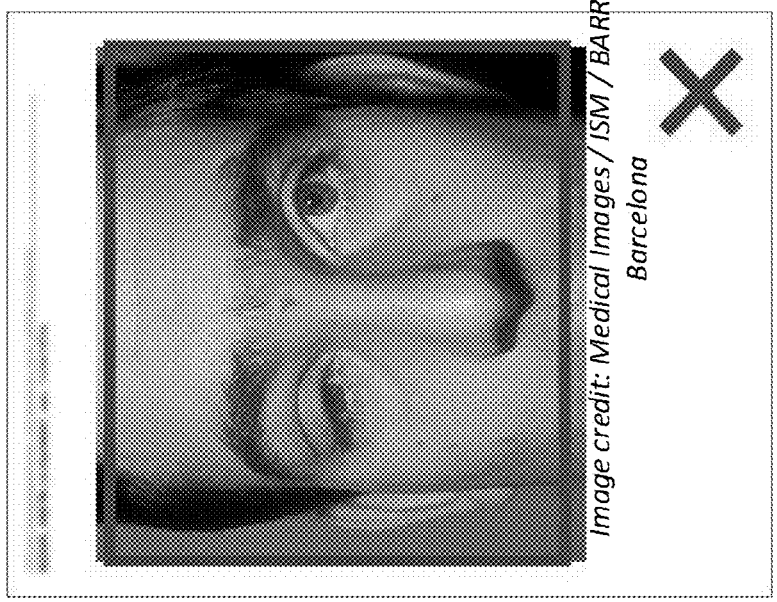
FIGS. 7A-7B are example images illustrating application of at least one quality control filter in accordance with certain embodiments.
Figure 7A:
Figure 8B:
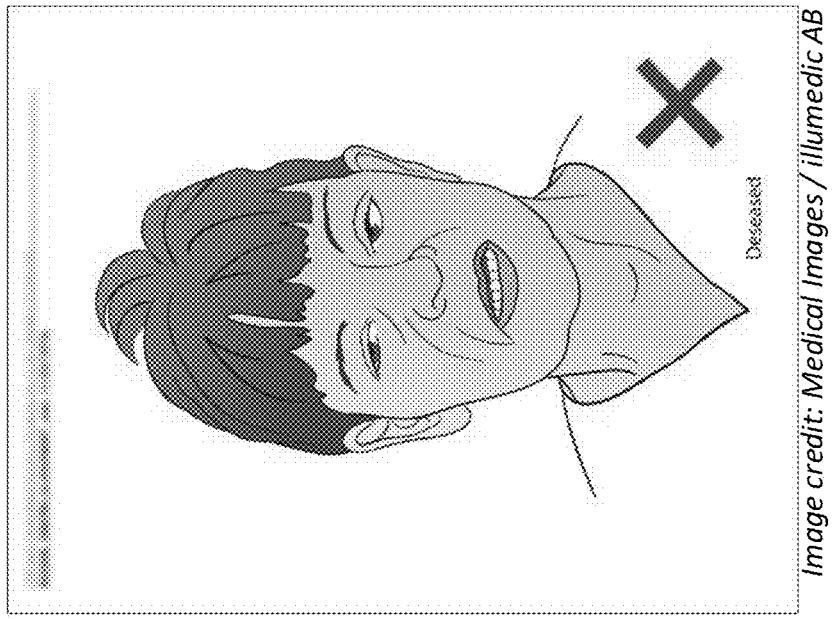
FIGS. 8A-8B are example images illustrating application of another quality control filter in accordance with certain embodiments.
Figure 8A:
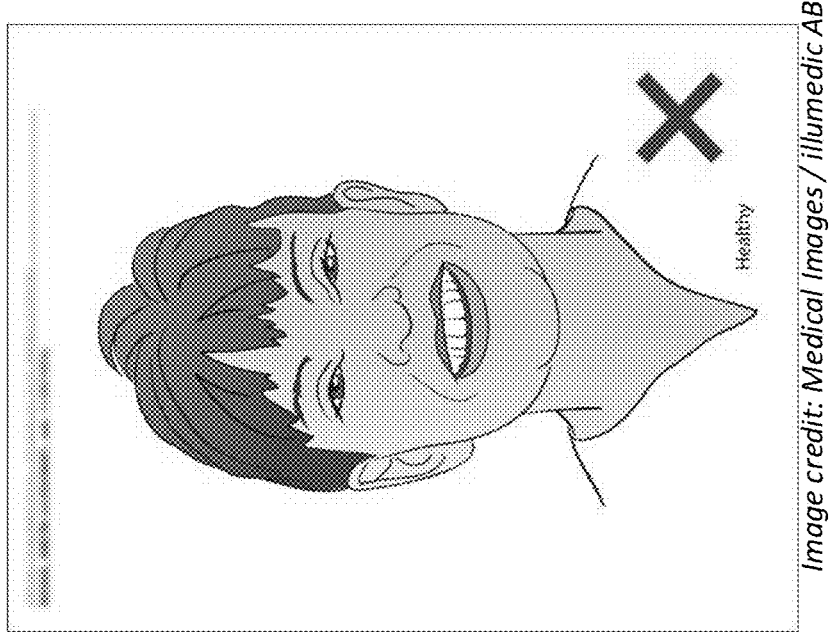
Figure 9B:
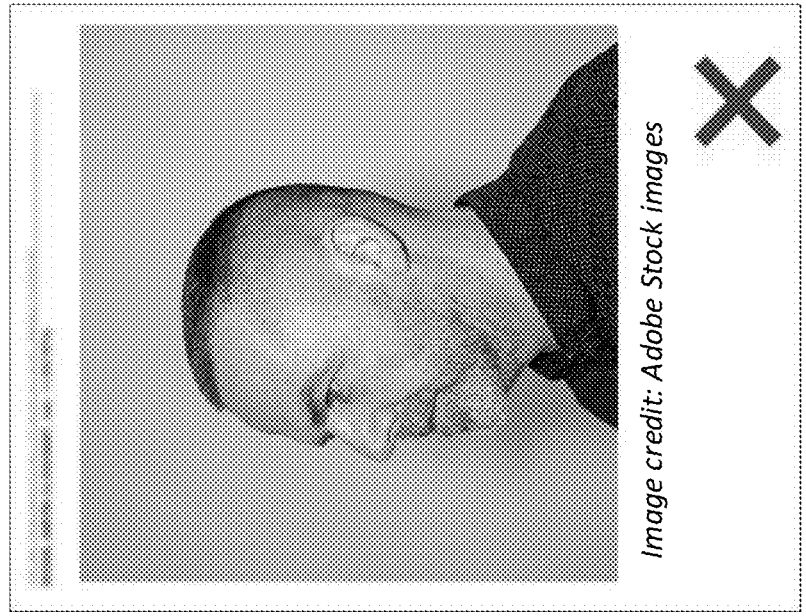
FIGS. 9A-9B are example images illustrating application of a content-orientation based filter in accordance with certain embodiments.
Figure 9A:

The image pre-processing steps may additionally comprise one or more additional quality-control processes, such as ensuring the image color profile is adequate for further analysis (e.g., determining whether a photograph is full-color or grey-scale, such as reflected in FIGS. 7A-7B), ensuring the images are photographs (or other appropriate imaging-device-generated images, rather than illustrations as reflected in FIGS. 8A-8B) for further analysis, and/or the like.

In certain embodiments, the image preprocessing process may additionally comprise certain steps for identifying features within the image, and for ensuring that those features deemed necessary for a relevant image analysis process are present within the image and oriented properly within the image to enable an objective determination of characteristics of the image in accordance with a relevant image analysis model. As an example with reference to FIGS. 9A-9B, the image preprocessing steps may comprise image analysis criteria indicating that a frontal-facial image is required for further analysis, and thus detecting (through machine-learning models) that the contents of an image does not satisfy applicable image analysis criteria may result in a determination that the image is inappropriate for further analysis. However, it should be understood that certain of these processes may be performed as a part of the image analysis process as discussed herein. In other embodiments, certain additional preprocessing steps as discussed herein may be performed during or after image analysis processes as discussed herein.

c. Feature Detection

Figure 4:
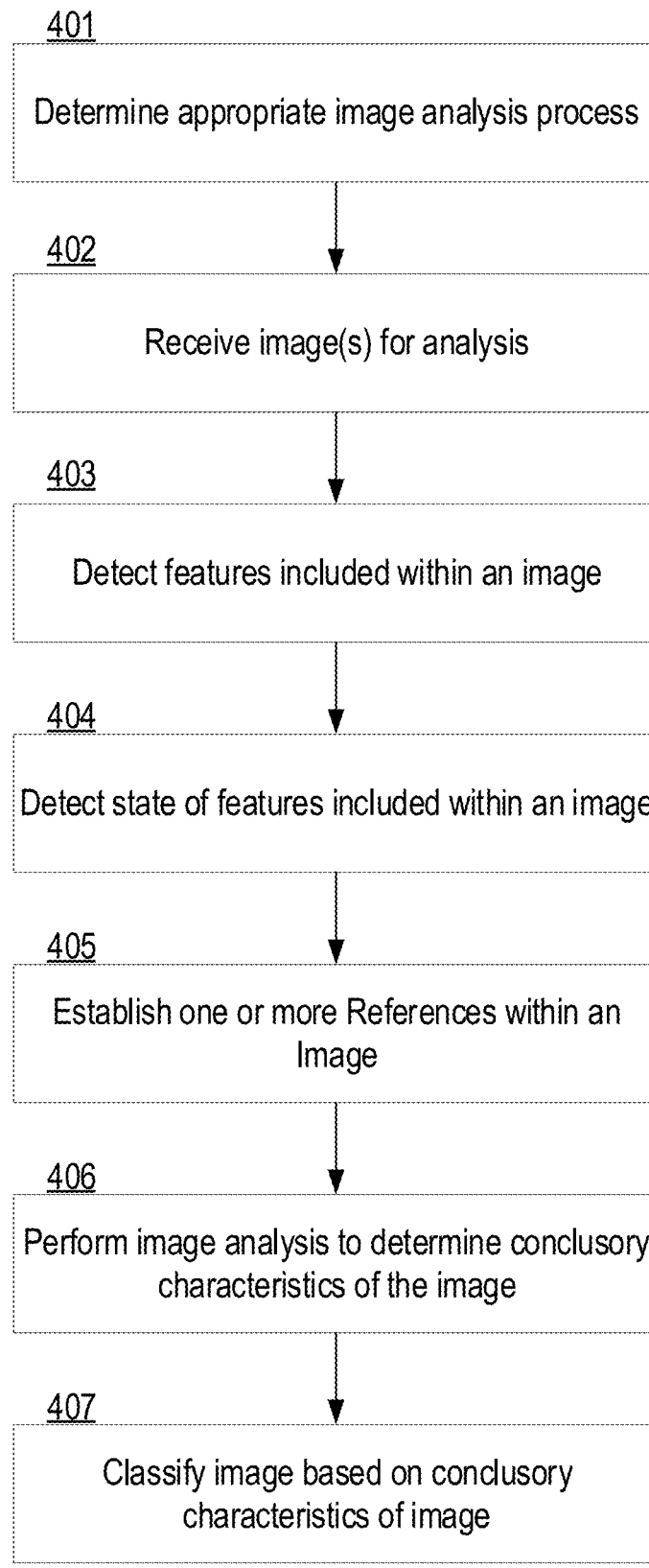
FIG. 4 is a flow diagram illustrating operation of processing images according to certain embodiments.

FIG. 4 provides a flowchart illustrating various steps involved in image analysis in accordance with certain embodiments. Image analysis may relate to analysis of specific features present within an image, and thus the process may begin with a determination of an appropriate analysis to be completed for a particular image, as indicated at Block 401. It should be understood that the determination of an appropriate image analysis may be identified during image pre-processing in accordance with certain embodiments. The image analysis process to be utilized for certain embodiments may comprise image analysis criteria, which may specify particular features to be identified and/or to be utilized for measurements (relative or absolute) during image analysis. Moreover, the image analysis criteria may additionally comprise and/or may specify particular models for use in identifying features within an image, for classifying features within an image, and/or the like. Such models may thus be generated and/or utilized for specific image analysis processes, thereby enabling the usage of specific models that need not include considerations of irrelevant aspects for the image analysis. As just one example, a determination of an appropriate image analysis may comprise specifying whether a blepharoptosis analysis, a sinusitis analysis, a scoliosis analysis, a skin lesion analysis, a vertebrae thinning analysis, a vertebroplasty analysis, a spinal canal analysis, a panniculectomy analysis, an orthognathic analysis, a breast surgery analysis, a rhinoplasty analysis, and/or the like is a most appropriate analysis for a particular image. It should be understood that the foregoing image analyses are merely examples, and other analyses may be utilized for certain embodiments. Moreover, although the discussed image analyses are specifically provided in accordance with medical diagnostic related imaging, it should be understood that image analyses according to certain embodiments may be utilized for other image-related analyses.

In certain embodiments, the identification of a relevant image analysis process may comprise receipt of user input identifying a selection of an image analysis process. In other embodiments, the identification of a relevant image analysis process may proceed automatically by the image analysis system 65, for example, by reviewing data provided together with the images (e.g., as a part of the source data file(s) provided and including the embedded images for analysis). It should be understood that any of a variety of methodologies may be provided for identifying a relevant image analysis process for performing the image analysis.

With reference to Block 402 of FIG. 4, the image analysis system 65 receives the images for further analysis in accordance with the identified image analysis process. It should be understood that the receipt of images may begin with preprocessing steps (including image selection), as discussed briefly above, such that only those images deemed sufficiently relevant and of sufficient quality for performing the image analysis process may be received and/or otherwise utilized for additional analysis. In yet other embodiments, the image analysis system 65 may receive a plurality of images which may be received together with corresponding priority scores for those images, thereby enabling a sequential processing methodology of those images, such that the images deemed to have a highest or best priority score are reviewed first, and lower-priority images are only reviewed if the higher-priority images do not yield a successful image analysis. As discussed in greater detail herein with specific reference to certain example configurations, certain image analysis processes may utilize a plurality of images simultaneously (e.g., collectively providing a three-dimensional representation of an imaged feature), and accordingly image analysis processes may utilize a plurality of images for conducting image analysis as discussed herein.

In certain embodiments, receipt of images may comprise receiving images provided via an application program interface (API), such that the image analysis system 65 may appropriately intake the images together with necessary metadata for further analysis. The images may be provided from a user computing entity 30 associated with a user, or the images may be provided from a preprocessing module in certain embodiments.

As indicated at Block 403, the image analysis system 65 is configured to detect individual features relevant for the image analysis that are present within the image. Accordingly, utilizing the image analysis criteria received previously, the image analysis system 65 identifies individual features within the image that are relevant for further analysis. For example, the image analysis criteria may indicate (e.g., within a list, a matrix, a reference table, and/or the like), specific features within an image to be identified, and individual entries within the feature listing may be associated with specific models (e.g., machine-learning based models) utilized for identifying those features within an image. However, it should be understood that a single model (e.g., a single machine-learning model) may be utilized for identifying all relevant features within a particular image in accordance with image analysis criteria.

As just one example, the machine-learning model may comprise a convolutional neural network (CNN) configured for identifying individual features of an image. The machine-learning model may be trained utilizing supervised training data in accordance with certain embodiments, utilizing labels within training data images identifying specific features therein. As a non-limiting example explained in greater detail in accordance with the described examples, when analyzing images for a blepharoptosis diagnosis, the patient's nose, eyes, irises, and eyelids may be detected within the image.

In various embodiments, the image analysis system 65 may further assign image-based characteristics to features detected within an image. For example, the image-based characteristics may be indicative of a relative location of a detected feature within an image. As a non-limiting example, after detecting a specific feature (e.g., via the CNN discussed above), the image analysis system 65 may determine a relative location of the detected feature within the image. The location may be relative, such as by detecting multiple features having a similar classification and assigning relative locations to each detected feature (e.g., a feature identified as the most-left feature, such as by pixel-location, may be assigned a "left" designation). The location may be relative to the image itself, such as by assigning a "left" designation to a feature indicated as being to the left of a center-point of the image (e.g., by comparing a pixel-based location of the detected feature relative to a total number of pixels within the width of the image). Analogous configurations may be utilized for "right," "top," "bottom" and/or other location-based designations of features within an image.

d. Feature State Detection

Once features have been identified within the embedded images, the image analysis system 65 of certain embodiments is configured to detect a state of one or more of the detected features, as indicated at Block 404 of FIG. 4. The detected state may be indicative of whether further analysis may be conducted on the embedded images. As a specific example, the image analysis system 65 may be configured to detect eyes reflected within an embedded image, and to detect the state of the eyes as being open, closed, partially closed, and/or the like.

As a part of identifying a state of features identified within the embedded images, the image analysis system 65 may be configured to identify sub-features, as well as a position of those sub-features relative to the including feature. With reference to the above-referenced example, the image analysis system 65 may identify the eyelid (and a lower edge of an upper eyelid) as a sub-feature of the eye, such that the image analysis system 65 may identify a position of the lower-edge of the upper eyelid relative to the overall eye, so as to determine whether the eye is open, closed, partially closed, and/or the like. In certain embodiments, the image analysis system 65 may be configured to identify a percentage value corresponding to a position of a sub-feature of a feature (e.g., indicating a percentage-closed that a an eyelid is, such as 30% closed, 80% closed, 100% closed, and/or the like).

Identifying the status of features may be performed utilizing a machine-learning model configured for comparing the image as a whole, or a portion of an image (e.g., a portion of an image containing a detected feature) against a training set providing example images of corresponding features in various states. For example, an initial determination of a state of a particular feature may be determined utilizing a binary classification model (e.g., a convolutional neural network) trained to classify identified features into one of two states. As a specific example, upon detecting a patient's eye within a patient facial photograph, the binary classification model may be utilized to classify the patient's eye as "open" or "closed." The image analysis system 65 may utilize cropped partial images placed around a detected feature, such as an individual detected eye within the image (and removing the surrounding portion of the image, including other portions of the patient's face) as input to the binary classification, such that a classification may be assigned to each individual detected feature. The image analysis system 65 may store data indicative of the resulting classification assigned to the feature within a data file corresponding with the image.

In certain embodiments, the classification model may be configured to assign one of more than two possible states to a detected feature. In the example relating to a patient's eye, the possible states may be indicated as "open," "closed," or "almost closed." As discussed in greater detail herein, the feature classification determined for one or more features within an image may be utilized for determining an appropriate routing of the image for further review. For example, an "almost closed" determination may be utilized to route the image to a human reviewer, because the state of the patient's eye may not be suitable for automated measurements of various features as discussed in greater detail herein.

In other embodiments, the image analysis system 65 is configured to utilize one or more machine-learning models to identify a plurality of sub-features within the identified feature, thereby enabling measurements (e.g., absolute measurements based on detected reference scales or relative measurements between sub-features).

Additional feature states may be detected in certain embodiments, which may utilize additional binary (or other discrete) classifications to provide a multi-stage classification detection system. Other, non-discrete classifications may be utilized in certain embodiments, such as detecting a relative position/orientation of a sub-feature. As an example, a feature state classification may comprise an eye gaze determination model, which may be utilized to detect the relative direction of a patient's eye gaze relative to a camera. This non-discrete classification system may be utilized together with discrete state assignment criteria, such as to assign an image classification as to whether the patient is/is not gazing directly at the camera utilized to generate the image.

e. Establishing a Reference within the Image

In certain embodiments, the image analysis system 65 identifies and tags features and/or sub-features as reference points within the image to enable further analysis (as indicated at Block 405 of FIG. 4), such as absolute-measurement-based analysis, relative-measurement-based analysis, feature classification-based analysis, and/or the like. Certain features and/or sub-features may be identified as a part of the feature-state classification methodologies as discussed above, and accordingly the image analysis system 65 may simply tag these identified features for further analysis.

Figure 16:
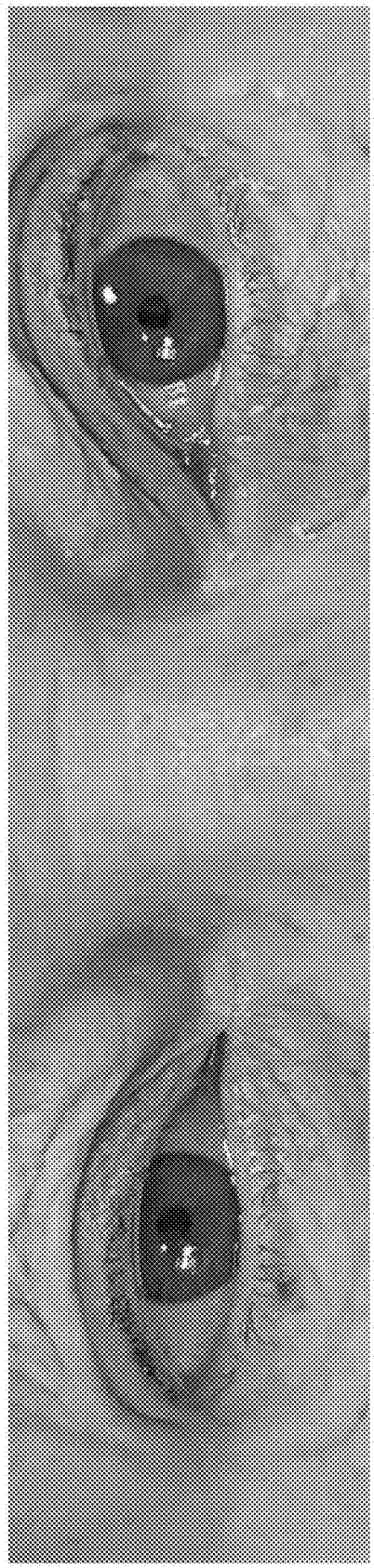
FIG. 16 is an example image illustrating application of sub-feature detection models in accordance with certain embodiments.

However, in certain embodiments, individual features and/or sub-features may be identified separately from those methodologies discussed above. As just one example, predictive-shape based analysis may be utilized to operate in conjunction with machine-learning based models (e.g., a convolutional neural network) to identify the boundaries of a feature defined within an image. By utilizing a predictive shape (e.g., a parabola, a circle, an oval, a square, and/or the like) as well as a machine-learning based model configured for identifying specific points on a boundary of a feature (as illustrated in FIG. 16 and discussed in greater detail with respect to the Blepharoptosis analysis discussed above), the image analysis system 65 may be configured to automatically connect detected individual points of a detected feature utilizing the predicted shape to generate an estimated boundary of the detected feature. As a specific example, the image analysis system 65 may comprise data indicating that a predicted shape of upper eyelids is a parabolic shape, the image analysis system 65 may be configured to utilize a machine-learning-based model to identify a plurality of points along an edge of a detected patient eyelid within an image, and to utilize parabolic modelling to connect those detected points to generate a predicted edge of an eyelid. This predicted edge may be utilized for later analysis, such as for determining an absolute or relative measurement of the positioning of the detected edge of the eyelid relative to other detected features within the image. It should be understood that other modelling may be utilized as well, such as analyzing and/or classifying a detected feature based at least in part on the generated equation utilized for modelling an edge of a feature (e.g., coefficients determined to be within an equation for modeling the curvature of a parabolic feature).

Other feature detection analyses may comprise machine-learning based analyses to match a detected feature with one of a plurality of stored templates each indicative of an available estimated feature shape. The available estimated feature shapes may be scaled to match the boundaries of a detected feature, thereby enabling more detailed analysis of the detected feature, such as center-point locating of the detected features. As a non-limiting example, the image analysis system 65 may utilize convolutional neural networks to identify irises shown within an image and to match the detected irises against one of a plurality of available iris shapes, thereby enabling the identification of a center-point of the detected irises. Moreover, as discussed in greater detail herein, the image analysis system 65 may store data indicative of an estimated overall size of an iris, such that data indicative of a scaling factor utilized to match a detected iris against one of a plurality of available estimated iris shapes may be utilized as a scaling factor for the image overall, such that absolute-measurements may be performed.

As a specific example of a process that may be utilized for matching features with one or more available templates corresponding to alternative shapes corresponding to the matched feature, a cropped portion of an image corresponding with a detected feature may be utilized for further analysis and detection of sub-features in accordance with an example analysis as indicated in FIGS. 11A-11E. By utilizing a cropped portion of an image (as reflected within FIG. 11A), the available contours reflected within the image is reduced, thereby reducing the number of false-positive feature identifications within the image. The cropped portion of the image may be converted to grayscale as reflected in FIG. 11B, and image noise may be removed via one or more image clarifying algorithms, such as Gaussian blur removal algorithms. Using the resulting clarified, grayscale image, contour edges may be detected within the image as being locations characterized as high intensity changes across a defined distance/number of pixels, the resulting image illustrating detected images is reflected in FIG. 11C. For example, Canny Detection algorithms may be utilized for detecting edges within the image. One or more geometric shape detection algorithms may be applied to the detected edges, such as a circle-detection algorithm (e.g., Hough Circles) utilized for detecting circles within the image, the resulting image having detected circle is reflected in FIG. 11D, with FIG. 11E representing potential circle detection errors in the event that a high sensitivity of detecting circles is utilized. Because this analysis is performed on a relatively small cropped portion of the image, the image analysis system 65 may operate with an assumption that only one set of edges within the cropped portion of the image will likely match the geometric shape of the model utilized. As an example, when detecting an iris within a cropped portion of an image corresponding with a patient's eye, the image analysis system 65 may determine that any edges determined to correspond with a circular shape is indicative of the location of the iris within the eye. Utilizing a larger cropped portion of an image, such as an entire patient's face, may result in false-positive identifications of an iris, since other edges within the image may be indicated as having a generally circular shape.

Certain embodiments, such as those reflected within FIGS. 12A-12E, may incorporate additional image-cropping methodologies for further refining the geometric-based image classification. For example, after converting a cropped image to grayscale (as reflected at FIG. 12A) an image mask may be applied to isolate a particular region of interest within the cropped image as reflected within FIG. 12B, such that edge detection (reflected within FIG. 12C) and later geometric-based image classification (e.g., detecting circular edges, as reflected in FIG. 12D) may be performed only on edges detected within the masked region (FIG. 12E reflects shape detection errors upon utilizing a higher sensitivity to detection of a desired shape). The image mask may be applied to a grayscale image (e.g., after removal of noise), and may identify regions satisfying an intensity criteria for defining edges of the generated mask. Details of the image occurring outside of the masked region may be removed from the image, and edges may then be identified based on the masked image before applying the geometric-based model.

FIGS. 13A-13E reflects yet another specific example configuration of a process that may be utilized for matching features with one or more available templates corresponding to alternative shapes corresponding to the matched feature, a cropped portion of an image corresponding with a detected feature may be utilized for further analysis and detection of sub-features. The image analysis system 65 may be configured to utilize a cropped color image of a feature (as shown at FIG. 13A), and to apply a color-based threshold (e.g., color intensity-based thresholding) to identify a darkest portion of an image. A color mask may be applied based on the detected darkest portion of the image as reflected within FIG. 13B. Moreover, the image analysis system 65 is configured to detect contour edges within the image as being locations characterized as high intensity changes across a defined distance/number of pixels as reflected within FIG. 13C. For example, Canny Detection algorithms may be utilized for detecting edges within the image. One or more geometric shape detection algorithms may be applied to the detected edges as indicated at FIG. 13D, such as a circle-detection algorithm (e.g., Hough Circles) utilized for detecting circles within the image. Although the resulting analysis may be utilized for identifying analogous features within mirrored features (e.g., utilizing a right eye analysis to identify a left-eye iris, as reflected in FIG. 13E), such a configuration may introduce errors in detection of substantially mirrored features without a separate analysis. Because this analysis is performed on a relatively small cropped portion of the image, the image analysis system 65 may operate with an assumption that only one set of edges within the cropped portion of the image will likely match the geometric shape of the model utilized. Moreover, when detecting edges corresponding to features (or sub-features) that are likely to be determined as the darkest portion of the image, the detected edges after identifying the darkest portion of the image are likely to be the edges of the feature (or sub-feature) to be identified. One or more geometric shape detection algorithms may be applied to the detected edges, such as a circle-detection algorithm (e.g., Hough Circles) utilized for detecting circles within the image. The detected geometric shape may correspond with the feature (or sub-feature) to be detected.

Figure 15D:
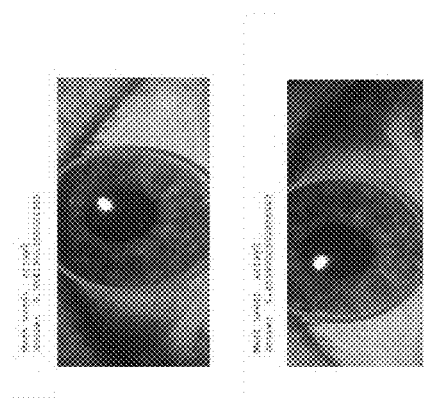
Figure 15C:
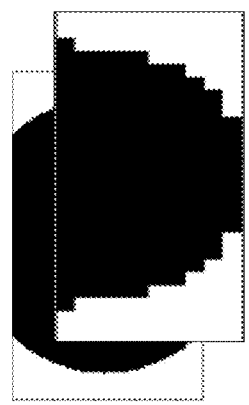
Figure 15B:
Figure 15A:
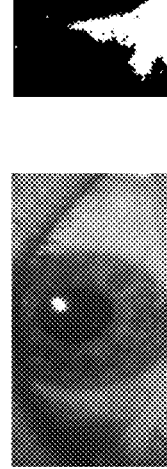

Upon identifying a desired feature to be detected, the image analysis system 65 may be configured to match the detected feature (or sub-feature) with a corresponding template as reflected within FIGS. 14A-14C and FIGS. 15A-15D. The image analysis system 65 may store a plurality of templates corresponding to one or more features (or sub-features) so as to enable accurate further analysis, for example, based on characteristics or specific locations within the feature to be detected. As just one example, utilizing a geometric shape identified within the image and determined to correspond with the feature (or sub-feature) to be detected within a cropped portion of an image (as reflected within FIG. 14A), the image analysis system 65 may generate a binary mask of the detected feature shape (e.g., a circular binary mask) as reflected within FIG. 14B (detecting a shape) and FIG. 14C (generating the binary mask based on the detected shape), that may be utilized for comparison against a library of available templates. Alternatively, a grayscale image (as shown at FIG. 15A) may be utilized for generating a binary mask (as shown at FIG. 15B) that may be utilized for detecting binary mask templates (as shown at FIG. 15C) corresponding with the image. The selected template may then be applied to the cropped image (as shown at FIG. 15D). Each of these templates may have corresponding features indicated in metadata stored with the templates, such as criteria for identifying a center-point of a feature corresponding with the template. To identify a matching template, the image analysis system 65 may generate a match score for each template indicating a degree of match between the template and the binary mask generated for the detected shape. The match score may be determined via any of a variety of methodologies, such as detecting a vector distance between a vector representation of the binary mask and a vector representation of the template (e.g., each vector representation being generated via a neural network analysis of the corresponding image). After generating match scores for each template, a closest match between the binary mask generated for the image and a template is determined, and the corresponding template is utilized for further analysis of the image. For example, based on characteristics stored in association with the image, the image analysis system 65 detects specific features of the image (e.g., a center-point of a detected feature or sub-feature; an edge of the detected feature or sub-feature, and/or the like), thereby enabling measurements between the specific points corresponding with the feature or sub-feature and other indicated points, contours, edges, and/or the like of the image.

f. Absolute-Measurement-Based Image Analysis

As indicated at Block 406 of FIG. 4, the image analysis system 65 is configured to utilize the detected features of an image as discussed above to perform one or more image analysis processes determined to be relevant for a particular image (e.g., based on user input specifying an image analysis to be performed). Such image analysis may comprise absolute-measurement-based image analysis, such as utilizing a detected scale for an image as well as known sizes (e.g., estimated sizes) of features detected within an image to measure the absolute distance between two or more features within the image. Such measurements may be performed utilizing any of a variety of measurement units, such as millimeters, inches, feet, and/or the like.

As noted above, certain detected features within an image may have a known size. The known size may be expressed in terms of a known distance between edges of a detected feature, such that the known distance may be correlated to the number of pixels within the image spanning the same distance. The image analysis system 65 may then utilize this known distance to assign an absolute size to each pixel, such that an absolute measurement within the image may be performed by counting the number of pixels between points within the image. As an example, an iris may have a known diameter (e.g., 10 mm), such that the number of pixels within the image between opposing edges of a detected iris may be utilized to generate a reference scale for the image, thereby establishing a size (e.g., in millimeters) of each pixel within the image.

When performing absolute-measurement-based analysis of an image, the image analysis system 65 is configured to detect two (or more) measurement points within an image, and to detect the number of pixels between those reference points, such that an absolute distance may be determined based on the measured number of pixels and the established scale (e.g., the established absolute size attributable to each pixel).

The individual points within an image for measuring may be identified via any of a variety of methodologies. For example, a single point may be identified as a center of one or more detected features, and the distance between the center of detected features may be determined. As another example, the edges of one or more detected features may be identified, and the minimum distance (or maximum distance) between edges of two or more features may be identified. As yet another example, a point attributable to a feature may be identified (e.g., a center, a defined point on an edge, and/or the like), and the image analysis system 65 may measure the distance between the identified point, in a defined direction (e.g., directly up within an image) to a point on an edge of another detected feature. Various combinations of these or other measurement strategies may be utilized in certain embodiments.

In certain embodiments, the image analysis process may store data indicative of measurement distance criteria for classifying images as reflected within Block 407 of FIG. 4. These measurement distance criteria may comprise one or more thresholds, one or more ranges, and/or the like that may be utilized for classifying the overall image. In certain embodiments, a plurality of measurement distance criteria may be stored for use with a particular measurement. Each of the plurality of measurement distance criteria may be applicable according to differing circumstances. With brief reference to the Blepharoptosis example discussed in detail below, the plurality of measurement distance criteria may comprise a plurality of maximum measurement distances for automatically assigning a Blepharoptosis diagnosis, each of the maximum measurement distances may apply for a different jurisdiction (e.g., different states and/or countries may utilize a different measurement criteria for establishing a Blepharoptosis diagnosis), for different ages (e.g., children may be subject to a different measurement criteria for establishing a Blepharoptosis diagnosis than adults), and/or the like. Accordingly, applying a particular measurement distance criterion may additionally comprise selecting an applicable measurement distance criterion based on one or more characteristics of a patient and/or other characteristics or data associated with a particular image.

As discussed in greater detail herein, the overall image classification may be utilized to determine appropriate further processing steps for the image, such as appropriate image routing for further analysis (e.g., to an appropriate human based on automated detections of images), to initiate payment based on documentation including the overall image, to update records corresponding with the image (e.g., update patient records to reflect a diagnosis determined based on the image analysis), and/or the like. For example, a distance threshold may be utilized, such that measured distances between specified features may be utilized for classifying an overall image. A distance between defined features above a threshold may result in the image receiving a first classification, a distance below the threshold may result in the image receiving a second classification. Moreover, upon determining that the distance between the defined features cannot be determined with sufficient accuracy, a third classification may be assigned to the image (e.g., the third classification being an error classification that results in generation of an alert to a user computing entity 30 providing the image that indicates that a new image is required for completion of the image analysis).

g. Relative-Measurement-Based Image Analysis

With reference again to Blocks 406-407 of FIG. 4, the image analysis system 65 may be configured to perform relative-measurement based image analysis for particular features identified within an image. The relative-measurement-based image analysis may comprise determining relative positions of multiple features, sub-features, and/or the like within an image, determining characteristics of a particular feature based at least in part on a matched template corresponding with the feature, and/or the like.

As just one example, the relative location of detected features within an image may be determined, such as by determining a relative orientation of the features (e.g., whether the features are aligned relative to one another, a percentage of misalignment/alignment relative to one another, a relative orientation (e.g., in degrees, radians, and/or the like) of features), and/or the like. To detect the relative location of detected features, edges of each feature may be detected, as discussed above. The edges of each feature may then be utilized to compare the detected features relative to one or more templates (e.g., through template matching processes discussed above) that may be correlated with feature characteristics, such as a feature orientation (e.g., defining a top of the feature, defining a front of the feature, and/or the like). By identifying an orientation of each individual feature, one or more reference planes may be associated with the feature within the image (that may be utilized for determining a relative orientation to other features, that may be utilized to determine a degree of alignment/misalignment relative to other features, and/or the like).

For those image analysis processes utilized for determining an angular orientation between two or more detected features, the image analysis system 65 may be configured to detect an angle between reference planes corresponding with each of the detected features. The detected angle may be compared against angle-based criteria, such as angular thresholds that may be utilized for classifying the image (e.g., as reflected within Block 407 of FIG. 4). As a non-limiting example, upon determining that the detected angle is above an angle threshold, the image may be assigned a first classification, and upon determining that the detected angle is below an angle threshold, the image may be assigned a second classification. As discussed in greater detail herein, the overall image classification may be utilized to determine appropriate further processing steps for the image, such as appropriate image routing for further analysis (e.g., to an appropriate human based on automated detections of images), to initiate payment based on documentation including the overall image, to update records corresponding with the image (e.g., update patient records to reflect a diagnosis determined based on the image analysis), and/or the like.

For those image analysis processes utilized for determining an alignment between features, the image analysis system 65 may be configured to detect a percentage of each of two or more features that are overlapping (e.g., by identifying a number of pixels between corresponding reference planes of each feature that are overlapping within at least one direction (e.g., a vertical direction) relative to a total number of pixels between reference planes corresponding with each detected feature. The detected percentage of alignment/misalignment may be utilized for classifying the image (e.g., as reflected within Block 407 of FIG. 4). As a non-limiting example, upon determining that the percentage of alignment is above an alignment threshold, the image may be assigned a first classification, and upon determining that the percentage of alignment is below the alignment threshold, the image may be assigned a second classification. As discussed in greater detail herein, the overall image classification may be utilized to determine appropriate further processing steps for the image, such as appropriate image routing for further analysis (e.g., to an appropriate human based on automated detections of images), to initiate payment based on documentation including the overall image, to update records corresponding with the image (e.g., update patient records to reflect a diagnosis determined based on the image analysis), and/or the like.

In other embodiments, an image analysis process may be utilized for detecting relative sizes of detected features (or between various portions of a detected feature) and/or sub-features within an image for providing an image classification. As an example, two or more features (or sub-features) may be detected within an image, wherein a first feature is located entirely within a second feature. The relative size of the first feature within the second feature (e.g., the percentage of a region within the second feature that is attributable to the first feature) may be utilized for classifying the image. A fill percentage threshold may be assigned to the image, and the detected fill percentage (e.g., the percentage of the second feature that is filled by the first feature) may be utilized for classifying the image. As a non-limiting example, upon determining that the fill percentage is above a fill percentage threshold, the image may be assigned a first classification, and upon determining that the fill percentage is below the fill percentage threshold, the image may be assigned a second classification. As discussed in greater detail herein, the overall image classification may be utilized to determine appropriate further processing steps for the image, such as appropriate image routing for further analysis (e.g., to an appropriate human based on automated detections of images), to initiate payment based on documentation including the overall image, to update records corresponding with the image (e.g., update patient records to reflect a diagnosis determined based on the image analysis), and/or the like.

In yet other embodiments, an image analysis process may be utilized for detecting relative sizes of detected features within an image for providing an image classification at least in part by determining a size ratio between two or more detected features (or between various portions of a single detected feature). As an example, two or more features may be detected within an image, wherein a first feature does not overlap with a second feature (i.e., the first feature and the second feature are discrete features identifiable within the image). The ratio of the size of the first feature to the size of the second feature (e.g., by overall area, by length, by width, and/or the like) may be utilized for classifying the image. The image analysis process may utilize a reference ratio for classifying the image, such that determined ratios of sizes between the first feature and the second feature that significantly deviate from the reference ratio may receive a first classification, whereas images reflecting a ratio between the first feature and the second feature that at least substantially matches the reference ratio may receive a second classification. In certain embodiments, determining whether the detected ratio between the first feature and the second feature deviates significantly from the reference ratio may be determined based at least in part on a threshold (e.g., based at least in part on a standard deviation of a sample data set relative to the reference ratio) and/or may be determined via a machine-learning model. As a specific example discussed in greater detail herein, an image of an underside of a patient's nose may be utilized to determine a ratio of sizes between a patient's nasal openings. A determination that the size ratio between the patient's nasal openings is significantly different than 1:1 (a ratio that would be indicative of at least substantially equal nasal openings), may be indicative of a nasal deformity, such as a nasal cavity collapse that may require a surgical rhinoplasty to correct.

As noted above, relative-measurement-based image analysis may utilize assigned classifications to certain features (or sub-features) for classifying the overall image. As an example, an identified feature within an image may be compared against one or more templates each having corresponding image classifications associated therewith. Based on the template identified as having a highest match score, the image classification corresponding with the template may be applied to the image.

As yet another example, certain embodiments may be configured to identify interruptions within a feature (e.g., to identify an indention within a surface of a feature) and/or to determine a relative depth of an interruption within a surface of a feature. The image analysis process may utilize a relative depth criteria for identifying whether a particular image satisfies a particular criteria. With reference to the below examples, an image analysis process may identify indentions within a patient's shoulders caused by bra straps, as a proxy for determining whether a patient's breasts are sufficiently heavy to justify breast surgery. Based on the presence or absence of an indention within the patient's shoulder skin, as detected by the image analysis process, and/or based at least in part on the depth of a detected indention within the patient's shoulder skin, the image analysis process may generate a classification to be assigned to an image that may be indicative of whether a claim for breast surgery is likely to be approved.

h. Image Analysis Tools

In certain embodiments, the image analysis system 65 is configured to provide one or more image analysis tools that may be accessible to one or more user computing entities 30 (e.g., via a web-browser based access, via a software program installed on the user computing entities, and/or the like). The image analysis tools may be configured for generating and/or otherwise providing a graphical user interface providing user-readable data regarding the results of the image analysis discussed above. In certain embodiments, the image analysis tool may be configured for providing a series of interactive user interfaces that may be provided to a user computing entity 30 and may be configured to enable the user to provide various user input. For example, a first user interface may be configured to enable a user to upload a file/document having one or more embedded images therein. The image analysis tool may then provide the uploaded files/documents to one or more preprocessing and/or image analysis systems 65 as discussed herein. The image analysis tool may then display one or more additional user interfaces to the user computing entity 30, such as a user interface indicating that the image analysis is being performed, and/or one or more user interfaces indicating the results of the image analysis, including annotations provided on the image at relevant portions of the image to provide additional indications to the user of the results of the image analysis.

The generated annotations may comprise graphical markers of identified features (e.g., a line illustrating a detected edge of a feature or sub-feature, a point indicating a point of reference for measurements, a boundary following a detected edge of a feature or sub-feature, a line indicating an estimated location of feature, a line indicating an estimated centerline of a feature, and/or the like). Moreover, in certain embodiments, the image analysis tool may be configured to selectively overlay one or more reference features, such as a reference grid having constant-sized grid blocks such as that shown in FIG. 17. These constant-sized grid blocks may be sized based at least in part on a detected reference size, thereby enabling a user to self-measure distances between various features within the image.

In certain embodiments, the various annotations may be selectively applied to an image, such as in accordance with user-input selecting one or more annotations to be applied to the image. Accordingly, the image analysis tool may be provided with a user interface comprising one or more interactive elements enabling a user to select one or more annotations to be applied to a displayed image. Moreover, in certain embodiments a user may manipulate annotations already present within an image, and/or the user may provide annotations or other indications of approval of use of images and/or attestation of various provided annotations.

Figure 18A:
Figure 18B:
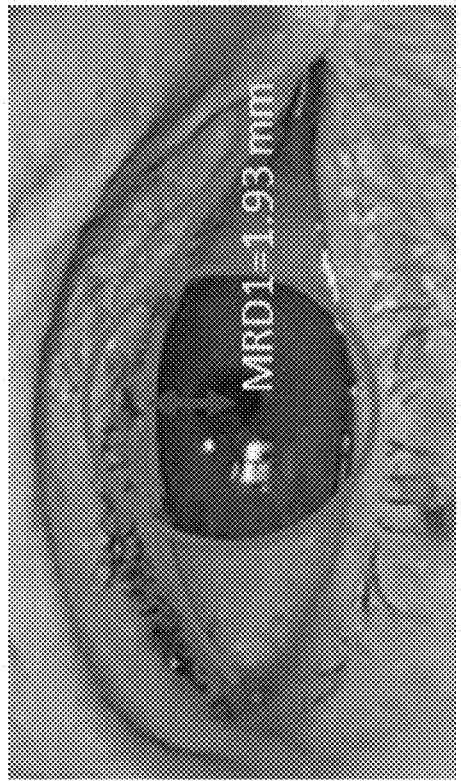

In certain embodiments, the image analysis tool may additionally comprise one or more features enabling users to generate custom reports, such as comprising images having overlaid annotations as discussed above, that may be output and provided to the user computing entity 30. As an example with reference to FIGS. 18A-18B, the annotated images may comprise images having overlaid shapes corresponding to identified features (e.g., illustrating an identified iris, an identified eyelid, and an identified measurement distance), and may be provided in various cropped image sizes, such as illustrating a pair of eyes as shown in FIG. 18A or a single eye, as shown in FIG. 18B. In certain embodiments, the generated reports may be provided to the user computing entity 30 for local storage thereon. In other embodiments, the generated reports may be provided to the user computing entity 30 for printing a physical report. It should be understood that these and/or other features for providing reports generated via the image analysis tool may be utilized in certain embodiments.

i. Image Routing

As noted above, the image analysis system 65 is configured to route images (and/or the documents/reports/files) to one of a plurality of routing locations based on an image classification assigned during the above-mentioned image analysis. For example, a document/report/file having at least one image embedded therein and having a first classification may be routed to a first location (e.g., transmitted to a first user computing entity 30) and a document/report/file having at least one image embedded therein and having a second classification may be routed to a second location (e.g., transmitted to a second user computing entity 30). Particularly when implemented in a healthcare claim approval context, the image analysis system 65 may be utilized for routing images (and corresponding reports/documents) to appropriate healthcare review staff based on an automated determination that a claim for which the document/report is generated has been indicated as meeting the criteria for approval of coverage or indicated as not meeting the criteria for approval of coverage (e.g., through an initial automated approval process). The automated determination of whether a claim has been indicated as meeting the criteria for approval of coverage may be accomplished based on a classification assigned to at least one image embedded within a report/document corresponding with a claim. For example, for particular claims, an indication of meeting the criteria for an approval of coverage may be provided upon determining that an embedded image is assigned a first classification, and an indication that a claim has not met the criteria for approval of coverage may be provided upon determining that the embedded image is assigned a second classification.

In certain embodiments, upon determining that the claim has been indicated as meeting applicable criteria for approval through the initial automated approval process (e.g., having a corresponding classification indicating approval of the claim), the claim including embedded images analyzed as discussed above may be routed to a nurse for a final determination of whether the claim has met the criteria for approval of coverage, while those claims indicated as not meeting the applicable criteria for approval of coverage based on the initial automated approval process may be routed to a licensed physician for final determination that the claim has not met the applicable criteria for approval of coverage.

j. Blepharoptosis Analysis Example

An image analysis system 65 according to certain embodiments may be configured to automatically diagnose various medical conditions of a patient that may be diagnosed based on images generated for the patient. Such images may comprise photographs for certain conditions, MRI-images for certain conditions, X-ray images for certain conditions, and/or other image types that may be useful for diagnosing other medical conditions. As just one example, the image analysis system 65 may be configured for diagnosing Blepharoptosis utilizing photographs of a patient's face. Specifically, the image analysis system 65 may be configured to detect the location of a patient's iris within each eye, and to measure a distance between a center of the patient's iris to the lower edge of the patient's upper eye-lid while the patient's eyes are fully open. Upon a determination that the measured distance satisfies a Blepharoptosis diagnosis criteria, such as a determination that the measured distance is less than a Blepharoptosis diagnosis threshold (e.g., an applicable Blepharoptosis diagnosis threshold selected from a plurality of available Blepharoptosis diagnosis thresholds based at least in part on data associated with an analyzed image, such as patient-specific data indicative of a patient location, a patient age, and/or the like), the image analysis system 65 is configured to generate data indicating a positive Blepharoptosis diagnosis. Alternatively, upon determining that the measured distance does not satisfy the applicable Blepharoptosis diagnosis criteria, the image analysis system 65 is configured to generate data indicative of a negative Blepharoptosis diagnosis. Based on the determined data indicative of a positive or negative Blepharoptosis diagnosis, the image analysis system 65 is configured to route the image (and/or any report/documentation containing the image) to an appropriate user computing entity 30 for determination of whether the claim has met the appropriate criteria for approval relating to payment of treatment for Blepharoptosis.

As discussed herein, images to be analyzed for a Blepharoptosis diagnosis may be extracted from reports and/or other documentation uploaded by care provider so as to automatically determine a diagnosis based at least in part on the images included in the report, and to thereby determine the accuracy of the report. Those reports and/or other documentation may comprise one or more images, text, and/or other documentation content, and accordingly the image analysis system 65 (alone or in combination with a separate image pre-processor) may extract images from the documentation, identify whether one or more of the extracted images are of sufficient quality for further analysis, and to pre-process the image to facilitate further analysis (e.g., by resizing images, by sharpening images, by rotating images, and/or the like), such as to enable application of machine-learning based models for identifying particular features and sub-features within the images. As discussed herein, such preprocessing may additionally comprise determining whether the patient's face is properly oriented within the image, determining whether the image has an appropriate color profile, and/or the like. One or more of these pre-processing methodologies may comprise one or more machine-learning based image analyses for automatically determining that the image is appropriate for further analysis thereof. Upon determining that the image is of sufficient quality and content, the image analysis system 65 performs Blepharoptosis specific image analysis to detect specific features of the patient's face, to determine a reference measurement scale, and for measuring the distance between the center of the patient's iris to the lower edge of the patient's upper eyelid (for each eye).

Figure 10B:
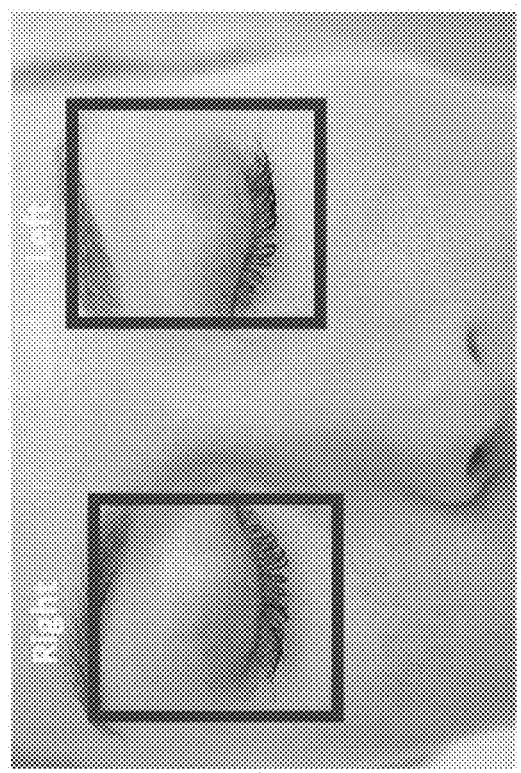
FIGS. 10A-10B are example images illustrating detection of specific features within an image in accordance with certain embodiments.
Figure 10A:
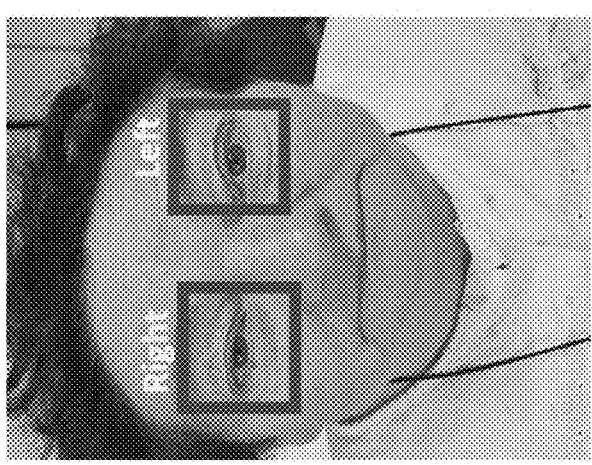
Figure 14C:
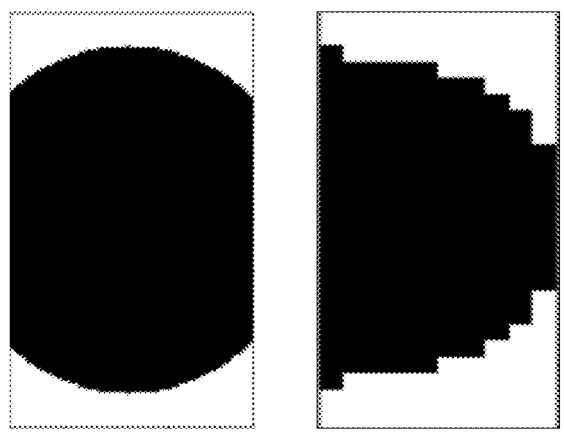
FIGS. 14A-15D are example images illustrating application of template matching processes with individual sub-features in accordance with certain embodiments.
Figure 14B:
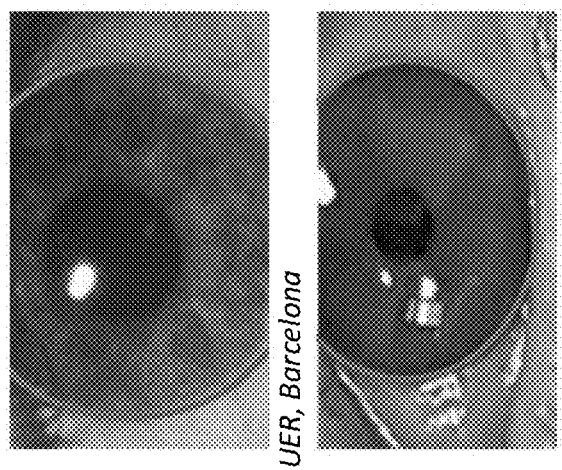
Figure 14A:
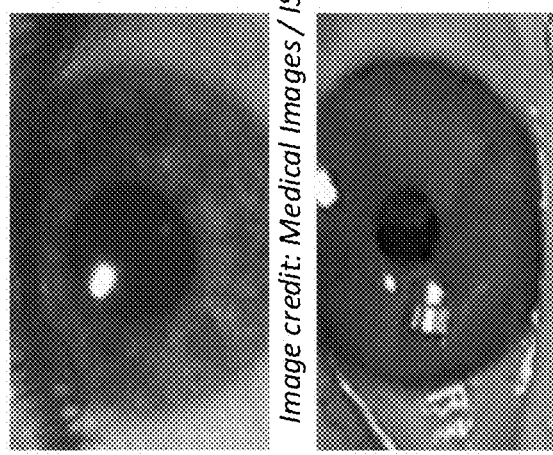

Within an image analyzed for Blepharoptosis diagnosis, the image analysis system 65 is configured to utilize convolutional neural networks to identify the patient's left and right eye within the image, as shown in the examples of FIGS. 10A-10B. The image analysis system 65 is configured to generate a bounding box to surround each detected eye, as shown in FIGS. 10A-10B. The bounding box may have a set size (e.g., 200 pixels by 200 pixels) or a relative size based on a detected size of a patient's eye.

Further analysis may then be performed on cropped images for each individual eye (thus excluding other portions of the patient's face within the image). Through the convolution neural network, or a separate convolutional neural network applied to the cropped images of the patient's eyes, the image analysis system 65 is configured to determine whether the patient's eyes are open, closed, or almost closed. Each of these discrete states may be identified by comparing the images against training data tagged with identical classification tags, thereby enabling the image analysis system 65 to determine whether the images of the patient's eyes most closely match the training data images of open eyes, closed eyes, or almost closed eyes. In certain embodiments, if the image analysis system 65 is incapable of determining the state of the patients eyes or if the image analysis system 65 determines that the patient's eyes are closed, the image analysis system 65 may generate an error to be provided to a user computing entity 30 originally providing the documentation including the embedded image, if no other images are available and satisfactory to complete the analysis. The error may indicate that additional images are necessary to complete the automated analysis. Moreover, upon determining that the patient's eyes are almost closed, the image analysis system 65 may conclude any further analysis and may provide the image to a human reviewer (e.g., a nurse or a physician operating a user computing entity 30) for further analysis.

Moreover, the image analysis system 65 may be further configured to determine a gaze of each of the detected patient's eyes, for example, based at least in part on convolutional neural networks utilizing training data classified via a binary classification system to indicate whether the eye is gazing at the camera (and therefore appropriate for further analysis) or the eye is not gazing at the camera (and therefore inappropriate for further analysis). It should be understood that other, non-binary or non-discrete classification systems may be utilized for classifying the patient's gaze, which may be utilized to determine whether the provided images are adequate for further analysis.

After determining that the image is appropriate for generating a Blepharoptosis diagnosis, the image analysis system 65 detects the lower edge of the patient's upper eyelids (for both eyes). As shown in FIG. 16, the image analysis system 65 identifies a plurality (e.g., 4) points along the lower edge of each eyelid, for example, utilizing edge-detection algorithms for distinctly identifying the lower-edge of the patient's eyelids (e.g., by identifying an edge between two components included in the image (e.g., based on differences in color on opposite sides of the identified edge). The image analysis system 65 then fits a parabolic curve to the four identified points (ending the parabolic curve at points identified as end points for each eyelid) to estimate the location of the lower edge of the patient's eyelid.

The image analysis system 65 additionally identifies the patient's iris in each eye for further analysis. To identify irises in a facial image, the image analysis system 65 utilizes an iris template repository comprising a plurality of iris templates of varying shapes that may be utilized to match to shapes detected within a facial image to indicate the location of the patient's iris, as well as a center-point of the patient's iris, even when the patient's iris is partially covered by the patient's eyelid. As discussed above, detection of an iris may be performed utilizing the cropped images of individual eyes of the patient, and applying one or more edge detection methodologies e.g., within a grayscale image, within a masked image, within a color-intensity-mapped image, and/or the like). Utilizing the location of detected edges within each cropped eye image, the image analysis system 65 utilizes circle-identification models to identify circular shapes within the cropped eye images, generates a binary mask of the circular shape identified within the cropped eye image, and identifies a closest matching iris template to the binary-masked image to determine an iris template most appropriate for the cropped eye image. To generate the binary-masked image, the image analysis system 65 is configured to convert a red-channel within the original image to binary (e.g., black and white), and the resulting binary image may be utilized for comparison with templates (e.g., utilizing a convolutional neural network to compare the binary mask against templates to identify a closest-matching template to be utilized for further analysis).

By matching an iris template with each eye within the facial image, the image analysis system 65 identifies boundaries of the patient's irises within the facial image. Moreover, the image analysis system 65 stores data indicating a patient's iris is to be estimated to have a 10 mm diameter. Thus, by identifying the edges of the patient's irises within the image, the image analysis system 65 is configured to determine a scale to be utilized for absolute measurements within the image, by determining the number of pixels across the diameter of the patient's iris, and correlating the determined pixel-based distance across the patient's iris with a 10 mm measurement, thereby enabling a determination of the absolute measurement distance to be correlated with each pixel within the image. Moreover, utilizing the iris template, the image analysis system 65 is configured to determine a center-point of the patient's irises (for each eye), despite a portion of each iris may be covered within the image by the patient's eyelid. For example, the center point of each eye may be identified geometrically, based on identified locations of edges of an identified iris.

Based on the determined center point of each iris, and the lower edge of each eyelid, the image analysis system 65 performs an absolute measurement of the distance between the center point of each iris and the corresponding lower edge of the upper eyelid (referred to as the MRD-1 measurement; an example MRD-1 measurement is visible within FIG. 18B). The image analysis system may be additionally configured to measure an MRD-2 distance, as the distance between the center of the iris and a detected upper edge of a lower eyelid, which may be detected in a manner similar to that discussed herein for detection of the lower edge of the upper eyelid. Moreover, the image analysis system 65 may store a Blepharoptosis diagnosis distance threshold that may be utilized for comparison to determine whether the image is indicative of a positive or a negative Blepharoptosis diagnosis. If the detected MRD-1 distance is less than (or equal to) the Blepharoptosis diagnosis distance, the image analysis system 65 may be configured to automatically provide a positive Blepharoptosis diagnosis, otherwise the image analysis system 65 is configured to automatically provide a negative Blepharoptosis diagnosis.

Figure 17:
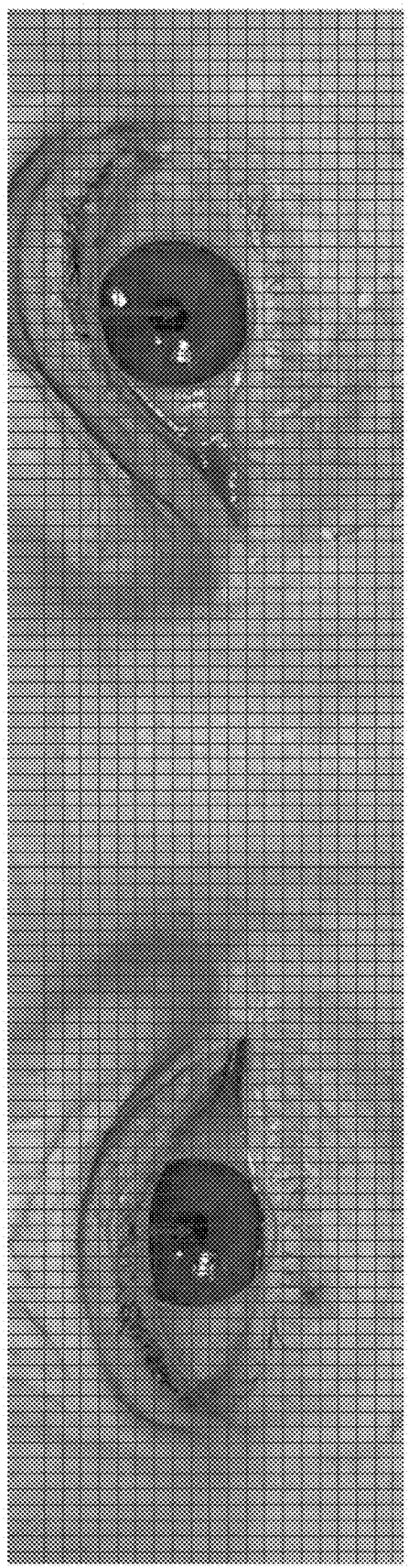
FIGS. 17-18B are example images illustrating example overlays that may be applied to an image within an image analysis tool in accordance with certain embodiments.

Based on the determined Blepharoptosis diagnosis, the image analysis system 65 is configured to route the image (and the containing report and/or document) to an appropriate user computing entity 30 corresponding to an approver (e.g., a nurse or a physician). The image analysis system 65 may be configured to route the image (and the containing report and/or document) to a first user computing entity 30 upon detecting a positive Blepharoptosis diagnosis, and to route the image (and the containing report and/or document) to a second user computing entity 30 upon detecting a negative Blepharoptosis diagnosis. In certain embodiments, the image (and the containing report and/or document) may be annotated automatically by the image analysis system 65 to facilitate human review. The annotations may comprise an annotated MRD-1 distance, a grid having blocks of a measured size based on the detected iris size (e.g., 1 mm grid blocks), an overlay of the detected iris, an overlay of the detected lower edge of the upper eyelids, and/or the like. As discussed above, those annotations may be selectively added and/or reviewed via user input to appropriate interactive elements of an image analysis tool to further facilitate human review. An example annotated figure is shown in FIG. 17.

k. Sinusitis Analysis Example

The image analysis system 65 may be configured for executing one of a plurality of image analysis processes, which may be selected based at least in part on user input, based at least in part on detected features within an image, based at least in part on detected text within a report/document containing the image, and/or the like. As another example, the image analysis system 65 may be configured for automatically finding sinus opacification—the absence of air within the defined bone contours of the sinus cavity (which may be indicative of sinusitis) based on CT images, utilizing an image analysis process as reflected within the images of FIGS. 19A-19E.

As discussed in reference to the Blepharoptosis diagnosis process discussed above, the image analysis system 65 may first extract images provided for analysis, and to determine whether the images are of sufficient quality and content to enable a finding of sinus opacification. Such images may be extracted from documents/reports or other data source files, as reflected at FIG. 19A. However, because a diagnosis is based on a CT image, rather than a photograph, the image analysis system 65 may be configured for implementing a different pre-processing and image quality check process than the Blepharoptosis diagnosis process discussed above.

Accordingly, after extracting images from the document (e.g., utilizing an edge detection algorithm based on a detected difference in color intensity between a generally white-background of a document and a generally-black background of a CT image), the image analysis system 65 may be configured to determine whether the CT image is of a sufficient size (e.g., in pixels) to enable an accurate determination of a finding of sinus opacification. Moreover, as discussed above, the image analysis system 65 may perform one or more image editing processes, such as image rotation, image sharpening, and/or the like to enable a more accurate determination of a finding of sinus opacification.

Once the image analysis system 65 has determined that the extracted image (examples of which are provided in FIG. 19B) is of sufficient size and quality to enable a finding of sinus opacification, and upon determining that the image is of a sufficient orientation to enable a finding of sinus opacification, the image analysis system may utilize one or more machine-learning based models for determining whether the content of the extracted image contains images of a patient's sinuses with sufficient clarity and orientation so as to enable an accurate assessment of whether the patient is suffering from sinus opacification, which may be indicative of sinusitis. As just one example, the image analysis system 65 may utilize a convolutional neural network to compare the contents of the extracted images with an image training set to determine whether the extracted image matches images within the training set that are deemed sufficient to enable a finding of sinus opacification.

Figure 19B:
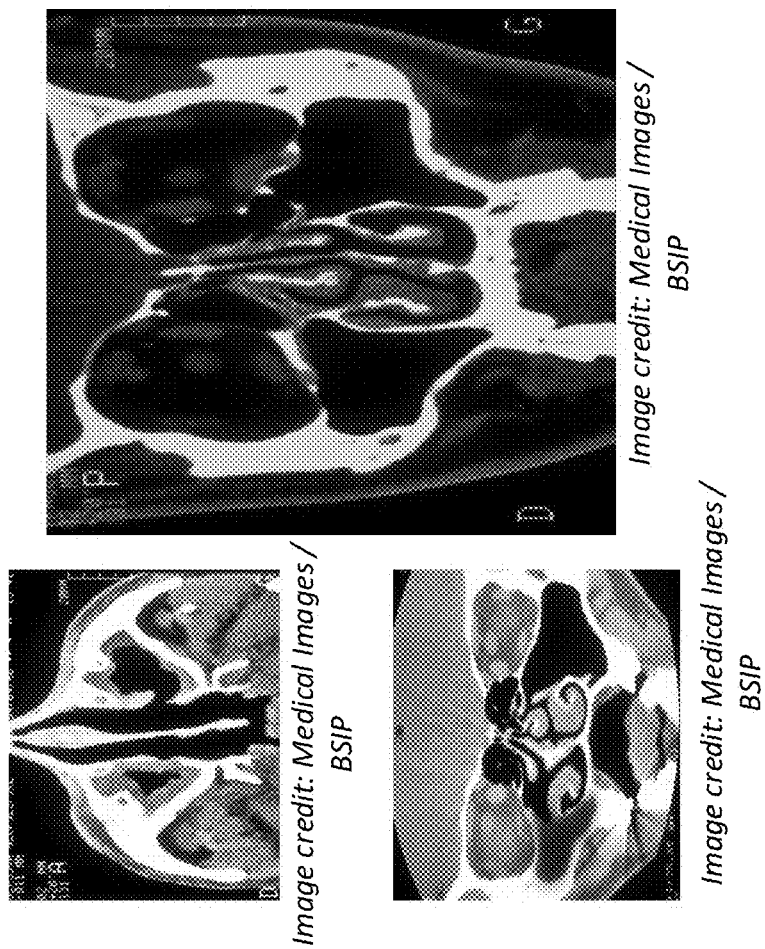
Figure 19D:
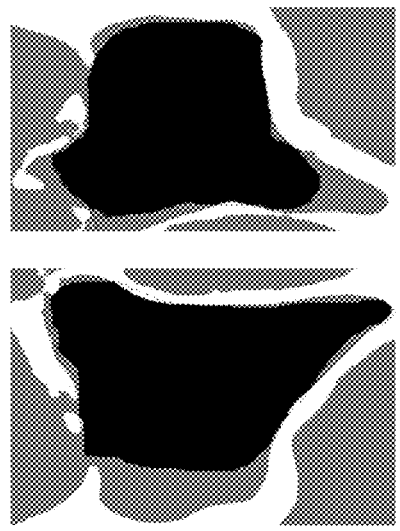
Figure 19E:
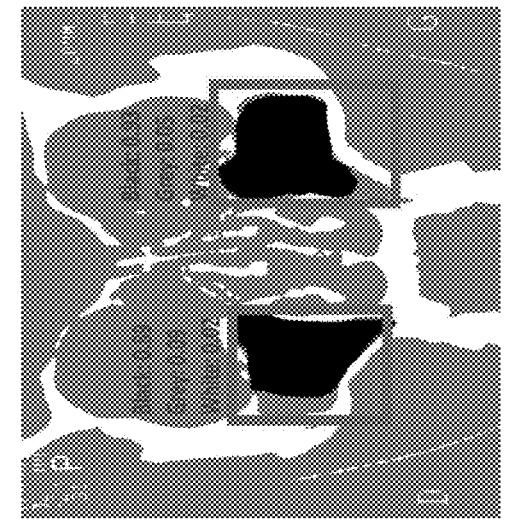
Figure 19C:
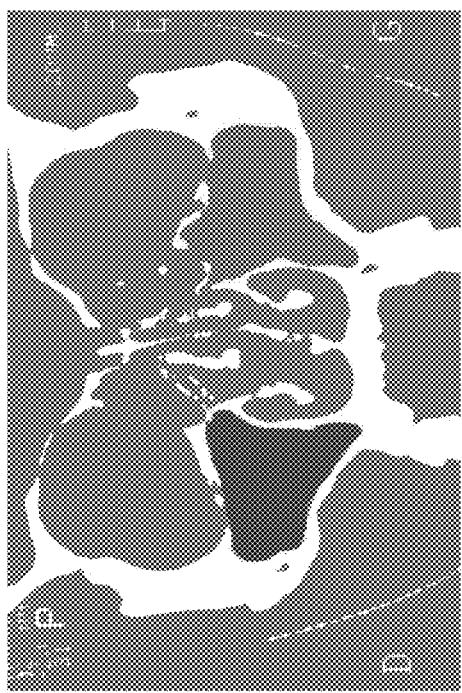

With reference to FIG. 19C, the image analysis system 65 applies a machine-learning-based (e.g., convolutional neural network) sinus detection model to identify the sinus cavities within the image. The sinus detection models may be configured to identify portions of the image having a known sinus cavity-shape, to identify relationships between various expected cavity shapes reflected within the image to identify a likely location of a sinus cavity within the image, and/or the like. The image analysis system 65 may then identify boundaries of each detected sinus cavity, for example, utilizing edge detection methodologies for identifying changes in image color intensity around an area identified as encompassing a sinus cavity. In certain embodiments, the image analysis system 65 is configured to generate an overlay (e.g., a color overlay, and image mask, and/or the like) having a shape, size, and location corresponding with the identified location of each sinus cavity within the image. The location, size, and boundaries of each sinus cavity may be stored (e.g., in metadata associated with the image) for further analysis. Moreover, in various embodiments, the image analysis system 65 may provide a bounding box surrounding the identified sinus cavities, such that the images may be cropped for further analysis.

Within each identified sinus cavity, the image analysis system 65 identifies tissue linings within the sinus cavity as reflected in FIG. 19D. The tissue linings may be identified as having a different color intensity within the image at a location determined to be within each identified sinus cavity. In various embodiments, the image analysis system 65 utilizes a sinusitis prediction engine to determine whether the identified sinus cavities and the identified tissue within each sinus cavity are collectively indicative of a sinus opacification (which may be indicative of a sinusitis condition). The sinusitis prediction engine may utilize a relative-measurement analysis configuration for determining whether sinus opacification finding criteria are satisfied.

As discussed above, the image analysis system 65 may store data indicative of a size (e.g., based on number of pixels, pixel-based area measurements, and/or the like) of the sinus cavities. The image analysis system 65 may similarly determine and store data indicative of a size (e.g., as a pixel-based measurement) of the area encompassed within identified boundaries of the tissue within the sinus cavity. The sinusitis prediction engine may encompass a machine-learning based (e.g., convolutional neural network based) models for determining whether a particular image is indicative of sinus opacification. For example, the sinusitis prediction engine may utilize a training data set (e.g., a labeled training data set) to determine a relevant percentage of coverage of the sinus cavity by the sinus tissue that is indicative of a finding of sinus opacification. Based on the determined sinus coverage percentage, the sinusitis prediction engine may calculate a sinus coverage percentage of the embedded image under analysis to determine whether the embedded image satisfies relevant sinus opacification finding criteria, which may be provided in the form of a threshold sinus coverage percentage. Other sinus opacification finding criteria may be implemented in certain embodiments, such as a percentage of a boundary of a sinus cavity in contact with identified sinus tissue, and/or the like. Because the sinus opacification finding criteria indicated above do not require absolute measurements between various features, the sinus opacification criteria may be implemented as relative-measurement-based analysis based on multiple identified features or sub-features (e.g., the sinus cavities and corresponding sinus tissue).

Upon determining whether the embedded image satisfies sinus opacification finding criteria, the image analysis system 65 assigns diagnosis data to be associated with the embedded image (and/or the documents/reports comprising the embedded image). The image analysis system 65 may thus generate and transmit data indicative of the resulting automatically generated diagnosis to the user computing entity 30 providing the embedded image, and may provide the document/report containing the embedded image, together with the embedded image (which may be annotated, such as with a visual overlay of the sinus cavity and sinus tissue, as well as a visual indication of the percentage of the sinus cavity occupied by the sinus tissue as reflected at Block 19E).

As discussed in reference to the Blepharoptosis analysis discussed above, based on a determination of whether a positive or negative finding of sinus opacification is determined for a particular embedded image, the image analysis system 65 may route the embedded image (e.g., together with the document/report containing the embedded image) to an appropriate user computing entity 30 for final approval of the determined diagnosis. For example, upon determining a positive finding of sinus opacification, the embedded image (e.g., together with the document/report containing the embedded image) may be routed to a first user computing entity 30 (e.g., operated by a nurse) for approval, and upon determining a negative finding of sinus opacification, the embedded image (e.g., together with the document/report containing the embedded image) may be routed to a second user computing entity 30 (e.g., operated by a physician) for evaluation.

Moreover, the image analysis system 65 may provide one or more image analysis tools, such as a user interface having a plurality of user input elements configured to enable a user to selectively apply one or more overlays to the embedded image that are indicative of the results of the sinus opacification analysis. As mentioned above, the image analysis system 65 may be configured to generate a visual overlay that may be selectively applied or removed from the embedded image to indicate the size, shape, and location of each of the identified sinus cavities and the identified sinus tissue. Moreover, the image analysis tool may automatically calculate a percentage of each sinus cavity occupied by the sinus tissue, and to display the calculated percentage within the embedded image.

l. Scoliosis Analysis Example

As noted above, the image analysis system 65 may be configured for executing one of a plurality of image analysis processes, which may be selected based at least in part on user input, based at least in part on detected features within an image, based at least in part on detected text within a report/document containing the image, and/or the like. As another example, the image analysis system 65 may be configured for diagnosing scoliosis based on X-ray images.

As discussed in reference to the Blepharoptosis diagnosis and sinus opacification diagnosis processes discussed above, the image analysis system 65 may first extract images provided for analysis, and to determine whether the images are of sufficient quality and content to enable a diagnosis of scoliosis. However, because a diagnosis is based on an X-ray image, rather than a photograph or a CT image, the image analysis system 65 may be configured for implementing a different pre-processing and image quality check process than the Blepharoptosis diagnosis and sinus opacification diagnosis processes discussed above.

Accordingly, after extracting images from the document (e.g., utilizing an edge detection algorithm based on a detected difference in color intensity between a generally white-background of a document and a generally-black background of an X-ray image), the image analysis system 65 may be configured to determine whether the X-ray image is of a sufficient size (e.g., in pixels) to enable an accurate determination of a scoliosis diagnosis. Moreover, as discussed above, the image analysis system 65 may perform one or more image editing processes, such as image rotation, image sharpening, and/or the like to enable a more accurate determination of a scoliosis diagnosis.

Once the image analysis system 65 has determined that the image is of sufficient size and quality to enable a scoliosis diagnosis, and upon determining that the image is of a sufficient orientation to enable a scoliosis diagnosis, the image analysis system 65 may utilize one or more machine-learning based models for determining whether the content of the extracted image contains images of a patient's spine with sufficient clarity and orientation so as to enable an accurate assessment of whether the patient is suffering from scoliosis. As just one example, the image analysis system 65 may utilize a convolutional neural network to compare the contents of the extracted images with an image training set to determine whether the extracted image matches images within the training set that are deemed sufficient to enable a diagnosis of scoliosis.

With reference to FIG. 20A, the image analysis system 65 applies a machine-learning based (e.g., convolutional neural network) spinal detection model to identify the spine within the image. The spinal detection model may be configured to identify portions of the image having a known spinal shape, to identify known relationships between various expected shapes represented within the X-ray image (e.g., where identified ribs connect with a larger elongated component—the spine—within the image), and/or the like. In certain embodiments, the identified spinal shape may be identified as having a color intensity deviation of less than a defined threshold percentage. The acceptable color intensity deviation may be identified by an appropriate machine-learning based model trained via a training data set in which the spine is identified in each image within the training data set, thereby enabling the machine-learning model to identify color intensity deviations within the indicated boundaries of an identified spine within each image of the training data set, so as to establish a maximum color deviation likely to be indicative of a continuous spine. The maximum color deviation may accommodate differences in color intensity in the X-ray image due at least in part to the presence of cartilage disks between individual bone vertebrae of the spine.

As shown at FIG. 20B, the image analysis system 65 may then identify individual vertebrae within the boundaries of the identified spine. The image analysis system 65 may utilize the above-noted differences in color intensity due to the presence of cartilage between individual vertebrae to identify the individual boundaries of each vertebrae. Any of a variety of methodologies may be utilized for identifying individual vertebrae, and such image analysis process may be performed within the boundaries set surrounding the spine identified within the image. In other embodiments however, the image analysis system 65 may expand the boundaries corresponding with the spine to accommodate potential errors in locating the boundaries of the spine, to accommodate the possibility that small portions of individual vertebrae may extend beyond the identified overall spinal boundary within the image.

In any event, within the identified boundaries of the image to be subject to further analysis for identifying individual vertebrae, the image analysis system 65 may identify boundaries between adjacent vertebrae and cartilage portions, so as to identify the boundaries of each individual vertebrae. Certain embodiments may execute such processes without further image manipulation. However, in other embodiments, the image analysis system 65 may generate one or more binary image masks based on detected intensity differences within regions of the image within the boundaries of the spine. The binary masks may thus emphasize the boundaries of each vertebrae, which may then be utilized to identify the location of each vertebrae boundary. Moreover, in certain embodiments, the image analysis system 65 may additionally utilize a machine-learning based vertebrae detection model to label each identified vertebrae. As just one example, the vertebrae detection model may utilize a labeled training data set in which each of a plurality of vertebrae within each image are individually labeled to uniquely identify each vertebrae visible within the image. The image analysis system 65 may then utilize this training data to review the embedded image provided for analysis to individually identify each vertebrae. Criteria utilized for identifying and labeling each vertebrae may comprise relative location-based criteria (e.g., relative location within the overall image, relative location compared with other identified vertebrae, relative location compared with other identified features of the image, such as the location of individual ribs, and/or the like).

Once individual vertebrae are identified, the image analysis system 65 may execute a relative measurement based image analysis process to determine whether the image is indicative of a scoliosis diagnosis. For example, an angle is measured between lines extending perpendicular to specific vertebrae located at the top and bottom of the spine, as shown in FIG. 20C. This angle, referred to as the Cobb's angle is determined by drawing a first line extending perpendicular to a central orientation line of a top-most identified vertebrae within the image and drawing a second line extending perpendicular to a central orientation line of a bottom-most identified vertebrae within the image. Cobb's angle is then measured at the intersection point between the first line and the second line. Because the determination of an angle between components is not dependent on the absolute size of any individual features (e.g., vertebrae), the image analysis system 65 need not determine absolute sizes of features identified within the image.

The image analysis system 65 may utilize a scoliosis diagnosis criteria for determining whether the image is indicative of a positive or negative scoliosis diagnosis. For example, the scoliosis diagnosis criteria may comprise a Cobb's angle threshold (which may be determined via manual user input identifying a threshold Cobb's angle for establishing a positive scoliosis diagnosis. In other embodiments, the scoliosis diagnosis criteria may be determined automatically, for example, utilizing a machine-learning based model utilizing a labeled data set comprising a plurality of spinal X-ray images each having corresponding labels indicating whether the image is indicative of a positive scoliosis diagnosis or a negative scoliosis diagnosis. The image analysis system 65 may utilize the training data to determine a threshold Cobb's angle for positively diagnosing scoliosis within an image under analysis.

Upon determining a Cobb's angle for the image and determining whether the Cobb's angle satisfies applicable scoliosis diagnosis criteria, the image analysis system 65 assigns diagnosis data to be associated with the embedded image (and/or the documents/reports comprising the embedded image). The image analysis system 65 may thus generate and transmit data indicative of the resulting automatically generated diagnosis to the user computing entity 30 providing the embedded image, and may provide the document/report containing the embedded image, together with the embedded image (which may be annotated, such as with a visual overlay of the identified spine, identified vertebrae, the generated first line and second line, the calculated Cobb's angle, and/or the like).

As discussed in reference to the Blepharoptosis analysis and the sinus opacification analysis discussed above, based on a determination of whether a positive or negative diagnosis of scoliosis is determined for a particular embedded image, the image analysis system 65 may route the embedded image (e.g., together with the document/report containing the embedded image) to an appropriate user computing entity 30 for final approval of the determined diagnosis. For example, upon determining a positive diagnosis of scoliosis, the embedded image (e.g., together with the document/report containing the embedded image) may be routed to a first user computing entity 30 (e.g., operated by a nurse) for approval, and upon determining a negative diagnosis of scoliosis, the embedded image (e.g., together with the document/report containing the embedded image) may be routed to a second user computing entity 30 (e.g., operated by a physician) for approval.

Figure 21C:
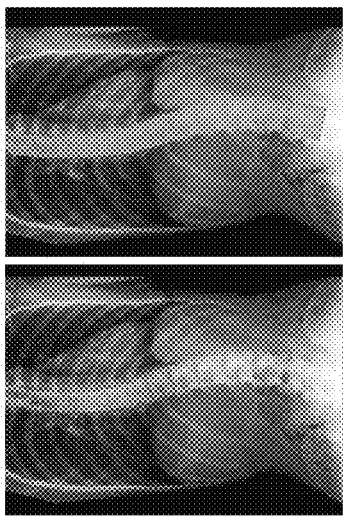
Figure 21B:
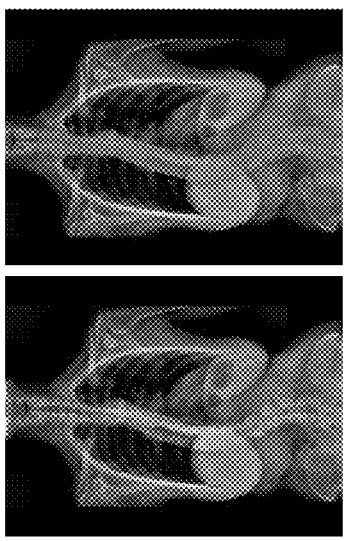
Figure 21A:
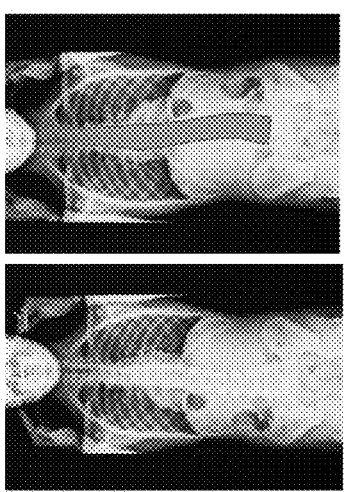

Moreover, the image analysis system 65 may provide one or more image analysis tools, such as a user interface having a plurality of user input elements configured to enable a user to selectively apply one or more overlays to the embedded image that are indicative of the results of the scoliosis diagnosis analysis. As mentioned above, the image analysis system 65 may be configured to generate a visual overlay that may be selectively applied or removed from the embedded image to indicate the size, shape, and location of the identified spine, the size, shape, and location of each of the identified vertebrae, the generated first line (extending from a top-most identified vertebrae), the generated second line (extending from the bottom-most identified vertebrae), the Cobb's angle, and/or the like. Example overlays are shown in FIGS. 21A-21C.

m. Skin Lesion Analysis Example

As noted above, the image analysis system 65 may be configured for executing one of a plurality of image analysis processes, which may be selected based at least in part on user input, based at least in part on detected features within an image, based at least in part on detected text within a report/document containing the image, and/or the like. As another example, the image analysis system 65 may be configured for diagnosing skin lesions based on photographs.

As discussed in reference to the Blepharoptosis diagnosis, sinus opacification diagnosis, and scoliosis diagnosis processes discussed above, the image analysis system 65 may first extract images provided for analysis, and may determine whether the images are of sufficient quality and content to enable a diagnosis of a skin lesion. In certain embodiments, such images may be provided as still-frame images or video-based images (e.g., a plurality of images provided in a chronological-based order) that may be previously captured (e.g., provided from an image library of a user computing entity) or captured in real-time (e.g., via an application executing on the user computing entity and/or a web-based application for capturing images with a camera of the user computing entity and communicating with the image analysis system 65). In certain embodiments in which a plurality of images are provided (e.g., as a part of a video), the image analysis system 65 automatically selects a most-appropriate image (e.g., based at least in part on a machine-learning based algorithm) for further analysis. For example, a most-appropriate image may be selected based at least in part on a determination that the most-appropriate image has clearly-defined edges of a skin lesion (e.g., an image having a highest contrast between adjacent pixels at an edge of a detected skin lesion identified through a machine-learning based model), such that a bounding box may be drawn around edges of the identified skin lesion to enable differentiation between various skin lesion types to enable classification of the skin lesion. Because a diagnosis is based on a color photograph, the image analysis system 65 may be configured for implementing image pre-processing features analogous to those discussed above in reference to the Blepharoptosis analysis process above. For example, the image analysis system 65 may detect color images embedded within the provided documents/reports to ensure that grayscale or black-and-white images are not provided for further analysis.

Accordingly, after extracting images from the document (e.g., utilizing an edge detection algorithm based on a detected difference in color intensity between a generally white-background of a document and background colors of a color photograph), the image analysis system 65 may be configured to determine whether the image is of a sufficient size (e.g., in pixels) to enable an accurate determination of a skin lesion diagnosis. Moreover, as discussed above, the image analysis system 65 may perform one or more image editing processes, such as image rotation, image sharpening, and/or the like to enable a more accurate determination of a scoliosis diagnosis. However, because the size and shape of various skin lesions may vary, the image analysis system 65 may not perform certain image editing processes, such as image rotation processes, as such image editing processes may not increase the accuracy of skin lesion diagnosis, and such image editing processes may not provide other benefits to users viewing the images (e.g., such as providing a point of reference for the generated images).

Once the image analysis system 65 has determined that the image is of sufficient quality to enable a diagnosis of a skin lesion reflected within the image, the image analysis system 65 may utilize one or more machine-learning based models for identifying boundaries of a skin lesion reflected within an image. The image analysis system 65 may utilize one or more feature detection models, such as those discussed in reference to the Blepharoptosis analysis discussed above for identifying the boundaries of a skin lesion reflected within an image. As an example, the image analysis system 65 may transform the image into grayscale and to perform color intensity determinations within individual pixels of the image, to identify a large change in color intensity reflected within the image. The image analysis system 65 may utilize the determined color intensity values corresponding with individual pixels to generate a binary mask corresponding with the color intensity values of the individual pixels. The boundaries of the binary mask may be identified as the boundaries of the skin lesion within the image. Data indicative of the boundaries of skin lesion may be stored as metadata with the embedded image.

Additional characteristics of the skin lesion may be determined, and corresponding lesion characteristic data may be stored in association with the image. For example, an average color of the skin lesion may be determined (e.g., by determining RGB color values for each pixel within the identified boundary of the skin lesion and determining an average RGB color value for the skin lesion). A percentage of color variation within the skin lesion may be determined (e.g., by determining RGB color values for each pixel within the identified boundary of the skin lesion and determining a maximum and minimum color value for each RGB color channel), and/or the like.

In certain embodiments, the image analysis system 65 may additionally utilize a skin lesion diagnosis model, such as a machine-learning based (e.g., convolutional neural network) skin lesion diagnosis model to automatically classify a skin lesion type. The skin lesion diagnosis model may utilize a training data set comprising images of a plurality of skin lesions, with each image having a corresponding label identifying a skin lesion type. Although the training data set may comprise images of a plurality of skin lesion types, recognizing that other skin lesions types may not be reflected within the training data set, the image analysis system 65 may utilize a scoring model for assigning a relevance score for each skin lesion type reflected within the training data set when determining a likely skin lesion type for a particular image. The skin lesion type having a highest score may be indicated as the likely skin lesion type reflected within the image, however only if the determined relevance score exceeds a defined relevance threshold.

The relevance scoring methodology may be performed utilizing the convolution neural network configuration mentioned above. Accordingly, a vector representation of an image of a skin lesion may be generated, and the image analysis system 65 may compare the vector representation of the image against vector representations of images within the training data set. A vector distance may be determined between the image under analysis and each image within the training data set, and an average vector distance may be determined for each skin lesion type (e.g., determining the average distance between the image under analysis and each image within the training data set having a corresponding label of a particular skin lesion type). The skin lesion type determined to have a closest average distance with the image under analysis may be determined to be the most-likely skin lesion type for assignment to the image under analysis. However, to minimize potential false-positive indications of a particular skin lesion type assigned to an image, the image analysis system 65 may utilize a relevance threshold for assigning a skin lesion type to a particular image. The relevance threshold may be determined automatically based on various characteristics of a training data set (e.g., a standard deviation generated for vector representations of each skin lesion type) or other characteristics of the training data set. Alternatively, the relevance threshold may be determined based at least in part on manual user input setting a relevance threshold for the skin lesion diagnosis process.

In certain embodiments, the image analysis system 65 may determine an appropriate routing for the image (e.g., together with the document/report containing the embedded image) based at least in part on the skin lesion diagnosis and/or the relevance score assigned to the skin lesion diagnosis. For example, upon determining the relevance score exceeds a routing threshold value, the image (e.g., together with the document/report containing the embedded image) may be routed to a first computing entity 30 (e.g., corresponding with a nurse) for final approval. However, upon determining that the relevance score does not exceed the routing threshold value, the image (e.g., together with the document/report containing the embedded image) may be routed to a second user computing entity 30 (e.g., corresponding with a physician) for final approval.

Figure 22:
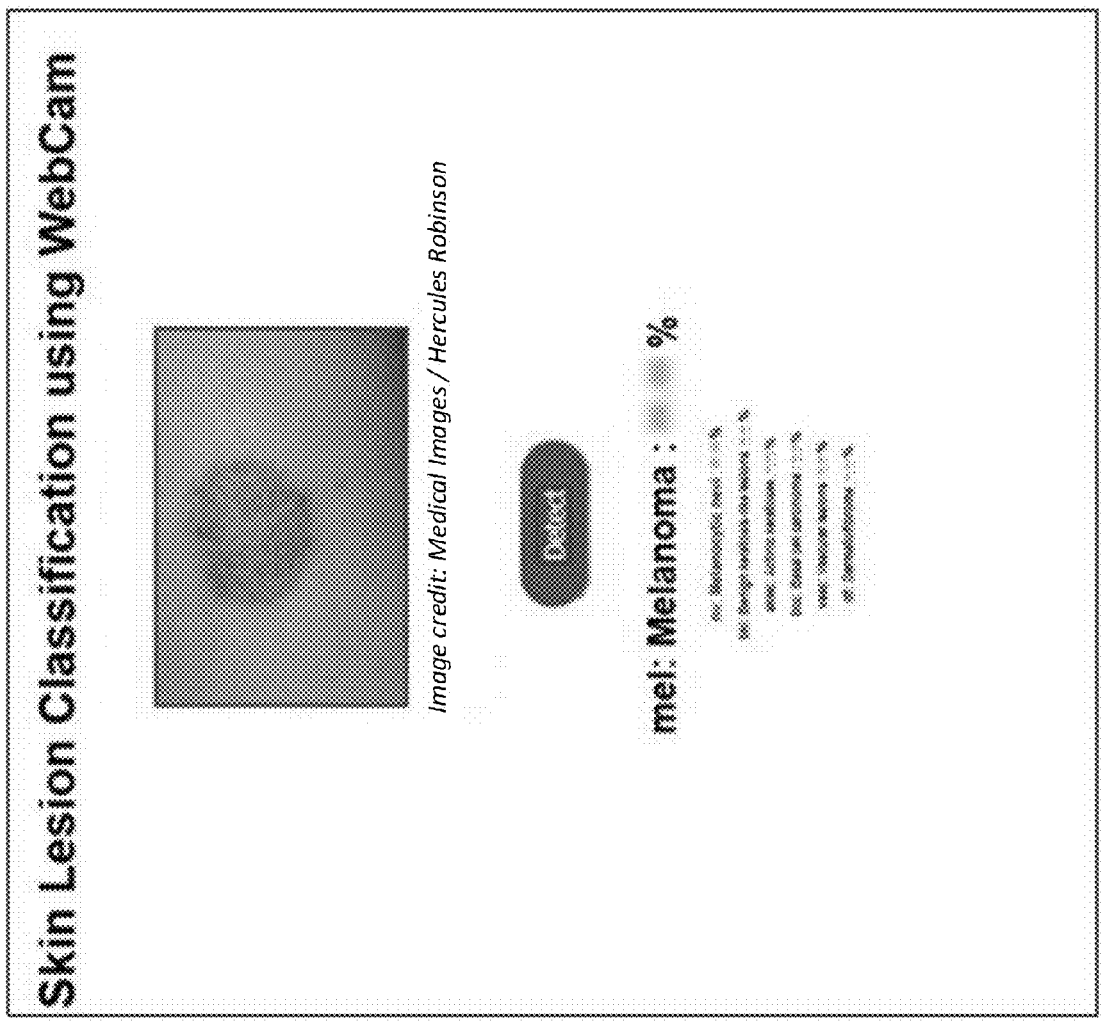
FIG. 22 is an example image relating to a skin lesion analysis in accordance with certain embodiments.

Moreover, the image analysis system 65 may provide one or more image analysis tools, such as a user interface providing additional data regarding the skin lesion diagnosis. For example, the image analysis tools may provide a visual indication of relevance scores for each of a plurality of skin lesion types, thereby providing an indication of the skin lesion type diagnosed for the image of the skin lesion. The image analysis tools may additionally enable the user to view additional representative images from the image training data to visually compare the image under analysis against images of various skin lesion types. FIG. 22 provides an example user interface of an image analysis tool showing an image under analysis together with indications of relevance scores for various skin lesion types reflected within a training data set.

n. Lung Nodule Analysis Example

As noted above, the image analysis system 65 may be configured for executing one of a plurality of image analysis processes, which may be selected based at least in part on user input, based at least in part on detected features within an image, based at least in part on detected text within a report/document containing the image, and/or the like. As another example, the image analysis system 65 may be configured for diagnosing lung nodules based on CT images.

As discussed in reference to the Blepharoptosis diagnosis, sinus opacification diagnosis, and scoliosis diagnosis processes discussed above, the image analysis system 65 may first extract images provided for analysis, and may determine whether the images are of sufficient quality and content to enable a diagnosis of a lung nodule. Because the identification and diagnosis of lung nodules is based on a CT image, the image analysis system 65 may be configured for implementing pre-processing and image quality check processes similar to that discussed above in reference to sinusitis.

Accordingly, after extracting images from the document (e.g., utilizing an edge detection algorithm based on a detected difference in color intensity between a generally white-background of a document and a generally-black background of a CT image), the image analysis system 65 may be configured to determine whether the CT image is of a sufficient size (e.g., in pixels) to enable an accurate determination of a lung nodule identification and diagnosis. Moreover, as discussed above, the image analysis system 65 may perform one or more image editing processes, such as image rotation, image sharpening, and/or the like to enable a more accurate determination of a lung nodule diagnosis.

Figure 23B:
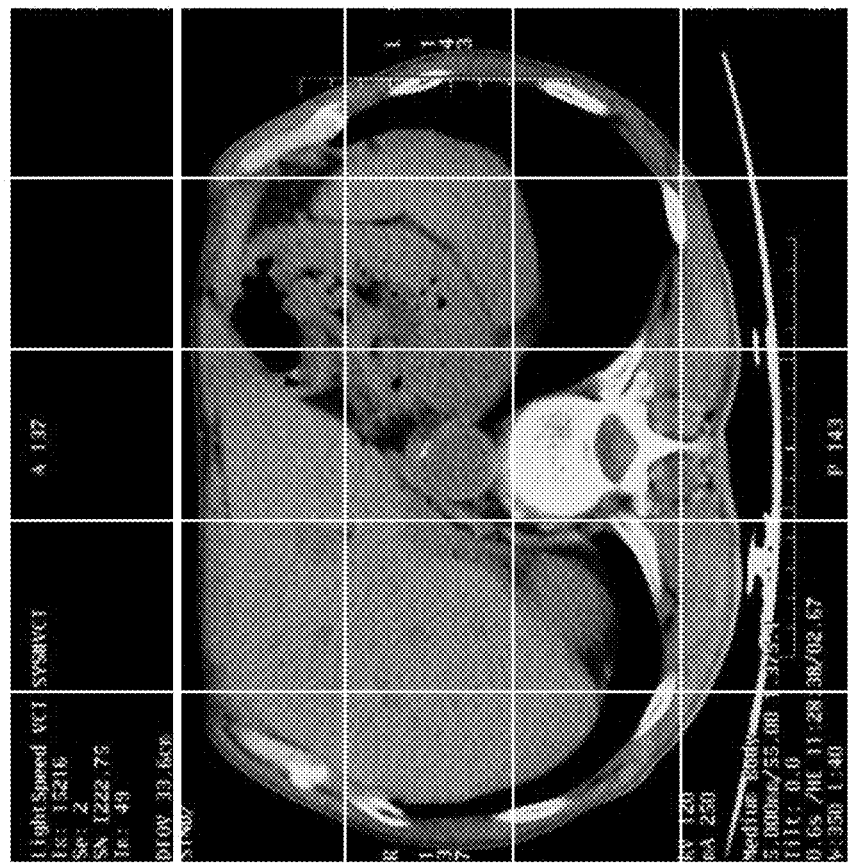
FIGS. 23-23B are example images relating to a lung nodule analysis in accordance with certain embodiments.
Figure 23A:
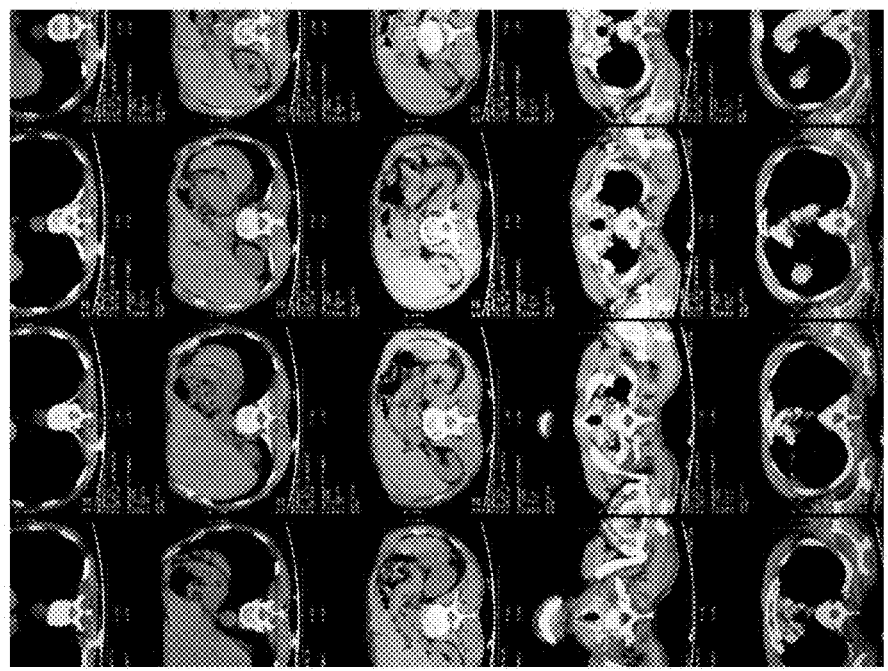

Once the image analysis system 65 has determined that the image is of sufficient size and quality to enable the identification and diagnosis of lung nodules included therein, the image analysis system may utilize one or more machine-learning based models for determining whether the content of the extracted image contains images of a patient's lungs with sufficient clarity and orientation so as to enable an accurate assessment of whether the patient's lungs have any nodules thereon, and whether those lung nodules are cancerous. As just one example, the image analysis system 65 may utilize a convolutional neural network to compare the contents of the extracted images with an image training set (example images of which are shown in FIG. 23A) to determine whether an extracted image such as that shown in FIG. 23B matches images within the training set that are deemed sufficient to enable the identification and diagnosis of lung nodules.

The image analysis system 65 utilizes a machine-learning based (e.g., convolutional neural network) lung nodule detection model to identify lung nodules within an image and to determine whether the detected lung nodules are cancerous. It should be understood that the image analysis system 65 of certain embodiments may be configured to implement a single-stage convolutional neural network configuration for both identifying lung nodules and classifying those lung nodules as cancerous or benign (e.g., identifying cancerous lung nodules separately from identifying benign lung nodules), or the image analysis system 65 of certain embodiments may be configured to implement a multi-stage convolutional neural network configuration that first identifies lung nodules, and then distinguishes between those lung nodules deemed cancerous and those lung nodules deemed benign.

The convolutional neural network may utilize a training data set comprising a plurality of CT images of patient lungs comprising data identifying lung nodules therein (including data identifying the location of boundaries of those lung nodules), or indicating that no lung nodules are present within the image. The training data set may additionally comprise diagnosis data for each identified lung nodule, indicating whether the identified lung nodule is cancerous or benign. The image analysis system 65 is configured for utilizing the training data to facilitate the identification of lung nodules within CT images provided as a part of a document/report for diagnosis of lung nodules therein.

As just one example, the image analysis system 65 is configured for executing a multi-stage convolutional neural network-based analysis of patient lung images. As a first stage, the image analysis system 65 is configured to identify and localize lung nodules within an image. Identification of nodules may comprise steps for generating candidate files corresponding with individual portions of an image that may be determined to comprise a region within an image that may be determined to be a lung nodule. These candidate files may be generated by first reviewing an image to identify regions of interest within an image, such as by detecting differences in intensity of color within the image. To avoid false positives and to thus decrease the number of candidate files, only those differences in color intensity within the data file corresponding with shapes determined to correspond with lung nodules may be flagged as potential candidates. For example, regions having a distinct color intensity that is distinguishable from surrounding regions, but having sharp corners or other shape characteristics that are generally not associated with lung nodules may be excluded from generation of candidate files. It should be understood that the identification of candidate files indicative of potential nodules may additionally comprise three-dimensional considerations of regions within images that may be indicative of lung nodules. In such configurations, a plurality of images (each image corresponding with a different imaging plane of the patient's lungs) may be considered simultaneously, so as to consider potential lung nodule shapes in three dimensions (e.g., within the two-dimensions represented within an individual image, as well as how various features may change in a third dimension represented by a series of adjacent image planes reflected within a plurality of images).

Identification of candidate files may proceed by identifying regions of changed color intensity within images and/or the identification of candidate files may additionally comprise execution of candidate nodule machine-learning based models (e.g., convolutional neural networks utilizing the above-mentioned training data for identifying and localizing regions of interest within individual images that may be reflective of a candidate nodule). For example, utilizing a candidate nodule machine-learning based model may comprise determining whether any individual regions within an image are determined to be similar to identified nodules within the training data set.

Once candidate files are generated for each prospective nodule, the image analysis system 65 executes a nodule classification model (e.g., a machine-learning based model, such as a convolutional neural network) to classify each candidate file as being reflective of a benign nodule, a cancerous nodule, a null nodule (reflecting a determination that the candidate is not a nodule at all), and/or the like. The classification model may be configured to apply one of a plurality of discrete classifications to each candidate file.

In various embodiments, classifying each candidate file may comprise detecting a closest match between various characteristics of a particular nodule relative to labeled nodules reflected within the training data set, as reflected within the image. For example, classifying each candidate file may comprise analyzing characteristics of the nodule such as the contours of the boundaries of a particular nodule (e.g., in two-dimensions within a single image or in three-dimensions across multiple images), the color intensity profile of the nodule within the one or more images (e.g., based at least in part on the average color intensity of the nodule, the location of variations in color intensity, and/or the like), the relative location of the nodule in comparison with the overall lung represented within the one or more images, and/or the like. In certain embodiments, the image analysis system 65 utilizes a convolutional neural network to generate a vector representation of the candidate file (e.g., a vector representation of each nodule reflected within the image). This vector representation of the candidate file may be compared against vector representations of each of a plurality of nodules reflected within the training data set so as to determine a vector distance between the candidate file and each of a plurality of nodules reflected within the training data. As noted above, the training data may have corresponding labels, such that the image analysis system 65 may be configured to determine an average distance between the nodule reflected within the candidate file and a plurality of nodules having a common classification. Accordingly, the image analysis system is configured to determine a closest average vector distance between the candidate file and a particular classified nodule type, as reflected within the training data. In certain embodiments, the image analysis system 65 assigns relevance scores to each possible nodule classification based at least in part on the average distance between the candidate file and training data having an associated nodule classification. The image analysis system 65 may be configured to assign relevance scores for each of the plurality of available classifications, and to select a highest relevance score as an automatically identified diagnosis of the nodule reflected within the candidate file (and the image(s) embedded within the document/report provided for analysis).

In certain embodiments, the image analysis system 65 may determine an appropriate routing for the image(s) (e.g., together with the document/report containing the embedded image(s)) based at least in part on the lung nodule diagnosis and/or the relevance score assigned to the lung nodule diagnosis. For example, upon determining the relevance score exceeds a routing threshold value, the image(s) (e.g., together with the document/report containing the embedded image(s)) may be routed to a first computing entity 30 (e.g., corresponding with a nurse) for final approval. However upon determining that the relevance score does not exceed the routing threshold value, the image(s) (e.g., together with the document/report containing the embedded image(s)) may be routed to a second user computing entity 30 (e.g., corresponding with a physician) for final approval.

Moreover, the image analysis system 65 may provide one or more image analysis tools, such as a user interface providing additional data regarding the lung nodule diagnosis. For example, the image analysis tools may provide a visual indication of relevance scores for each of a plurality of lung nodule types, thereby providing an indication of the lung nodule type diagnosed for the image of the skin lesion. The image analysis tools may additionally enable the user to view additional representative images from the image training data to visually compare the image under analysis against images of various lung nodule types. FIGS. 23A-23B illustrate example aspects of an example user interface of an image analysis tool showing an image under analysis together with various example training data images of various lung nodules as reflected within a training data set.

o. Mammogram Analysis Example

As noted above, the image analysis system 65 may be configured for executing one of a plurality of image analysis processes, which may be selected based at least in part on user input, based at least in part on detected features within an image, based at least in part on detected text within a report/document containing the image, and/or the like. As another example, the image analysis system 65 may be configured for detecting and diagnosing masses visible within an input mammograph. The image analysis system 65 may be configured to execute mammograph analysis based at least in part on two-dimensional images and/or three-dimensional images (e.g., image sets). Moreover, in certain embodiments, mammograph analysis may be performed utilizing relative-based measurements, such as for establishing a relative size of a detected mass within an image, or absolute-based measurements, such as for establishing an absolute size of a detected mass within an image, such as utilizing metadata indicative of an image scale within an analyzed image.

Figure 24:
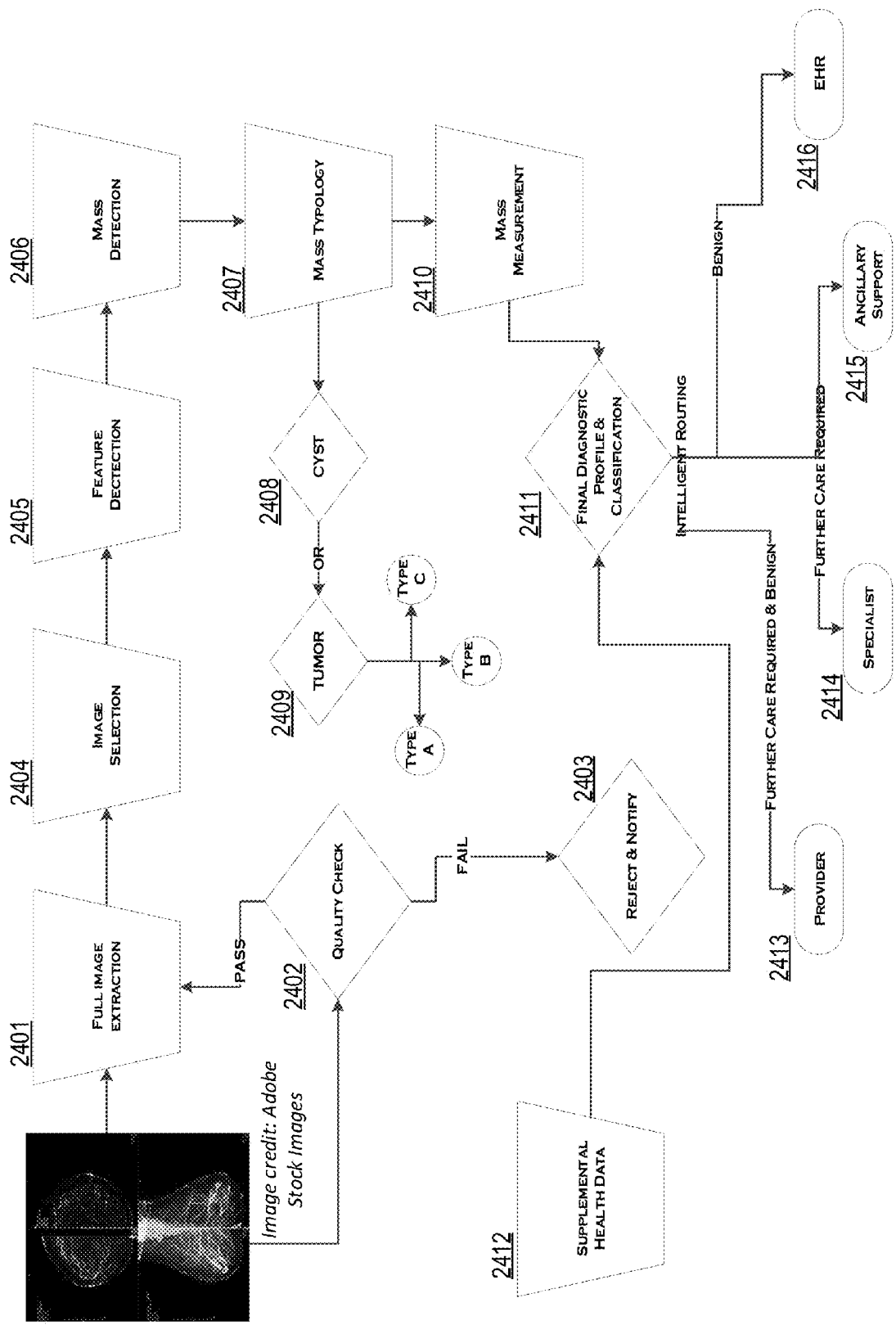
FIG. 24 is an example flowchart illustrating analysis of a mammography in accordance with certain embodiments.

FIG. 24 provides an example flowchart illustrating steps associated with analysis of a mammograph in accordance with certain embodiments. As discussed in the examples provided above, the image analysis system 65 may first extract images provided for analysis, as reflected at Block 2401. As discussed herein, the images may be extracted from an input file, such as a document/report generated based at least in part by a healthcare provider, which may contain both textual descriptions of the healthcare provider's assessment of a particular patient's condition, and images (e.g., mammographs). The input files may comprise a plurality of images, and accordingly the image analysis system 65 is configured to determine whether the images are of sufficient size (e.g., in pixels), quality, and content to enable a diagnosis of a breast mass. The image analysis system 65 may be configured for implementing pre-processing and image quality check processes (as reflected at Block 2402) such as those discussed above in reference to sinusitis or other non-photograph related image preprocessing configurations discussed herein. Those images that fail the relevant quality control checks are rejected, as indicated at Block 2403, and the image analysis system 65 may be configured to transmit a notification to the user computing entity 30 originally providing the input files indicating that one or more images included within the provided input file are not suitable for automated image analysis. It should be understood that such notifications may only be generated upon determining that all images within a relevant input file failed the relevant quality control check, and in such embodiments, the process may continue upon selecting (in Block 2404) at least one image that satisfies applicable criteria for analysis.

Moreover, because the input data file may comprise a plurality of images, the preprocessing steps may additionally comprise an image selection step, as reflected at Block 2403. As discussed above, the image analysis system 65 may be configured to generate quality scores, relevance scores, and/or the like for each image in those instances in which an input document comprises a plurality of images therein. Such scores may be based at least in part on detected image quality, detected image size, detected image content (e.g., utilizing detected features as a part of a criteria for generating a score), and/or the like. The scores assigned to each image may be generated based at least in part on application of a machine-learning based scoring model as discussed herein. As indicated at Block 2404, one or more images are ultimately selected for further analysis (e.g., the highest scored images may be selected for further analysis).

With reference to Block 2405, the image analysis system 65 executes one or more feature detection models for detecting individual features reflected within the image. Such features may comprise an overall breast shape (e.g., based on differences in color intensity within the image), one or more dense portions within the image, and/or the like.

Utilizing one or more machine-learning based models, the image analysis system 65 identifies one or more features as a mass subject to further analysis, as reflected at Block 2406. As discussed in reference to the lung nodule analysis discussed above, the image analysis system 65 may be configured to identify one or more features identified within an image as a mass candidate when initially identifying such features. Each of those mass candidates may be isolated for further image based analysis, such as by cropping the containing image around the detected mass candidate, such that further analysis and ultimate determinations of a candidate as being a mass (as indicated at Block 2406) may proceed utilizing the smaller, cropped images encompassing the mass candidate.

In certain embodiments, a determination of a particular mass candidate as a mass subject to further analysis may comprise applying a machine-learning based (e.g., convolutional neural network) model trained using a training data set of a plurality of images having corresponding labels indicating whether the image includes a mass. Such processes may proceed in a manner analogous to that for detecting lung nodules, as discussed above, utilizing an appropriate training data set for identifying breast masses.

As indicated at Block 2407, the image analysis system 65 is configured for determining a typology for all those masses detected as noted above. The image analysis system 65 may utilize one or more classification machine-learning models, such as convolutional neural networks, for assigning a classification to individual images, selected from a defined set of available classifications. With reference to the specific example of Blocks 2408-2409 of FIG. 24, the image analysis system 65 may be configured to distinguish between benign cysts and tumors, and to assign corresponding classifications to images based on the determined contents thereof. As additionally indicted at Block 2409, the image analysis system 65 may be additionally configured to assign one or more sub-classifications (e.g., assigning a tumor type sub-classification) through application of the classification model.

With reference to Block 2410 of FIG. 24, the image analysis system 65 is configured to perform one or more mass measurement processes for detecting a size of a mass identified within an image. The mass measurement processes may comprise one or more absolute-measurement processes such as those discussed above (and utilizing metadata indicative of an image scale embedded within one or more images), after utilizing the detection of a feature having a known size for generation of a scale to be utilized for performing absolute measurements within the image. In other embodiments, the mass measurement processes may comprise one or more relative-measurement processes such as those discussed above for establishing a relative size of a detected mass within an image. For example, the size of a mass may be identified as a percentage of an image (e.g., based on number of pixels identified as associated with the detected mass relative to the total number of pixels within an image encompassing a breast region).

In other embodiments, the image analysis system 65 is configured to perform one or more relative measurement processes for detecting a relative size and/or location of a mass identified within an image. The mass measurement processes may comprise detection of a boundary assigned with each mass, and boundaries assigned to one or more additional detected features within the image, thereby enabling a determination of relative positions of the detected masses relative to other detected features within the image.

As indicated at Block 2411, the image analysis system 65 is configured to generate a final diagnostic profile and classification for any detected masses within an image. Such diagnostic profile may comprise patient-specific diagnostic indications, which may be based at least in part on supplemental health data received by the image analysis system 65, as indicated at Block 2412 (e.g., data indicative of a family history of breast cancer, a personal history of surgery or trauma in the region of the identified lesion, a personal history of infection such as fever and/or localized redress, and/or the like).

With reference to Blocks 2413-2416, the image analysis system 65 may be configured to determine an appropriate routing for the image(s) (e.g., together with the document/report containing the embedded image(s)) based at least in part on the final diagnostic profile and classification as indicated at Block 2411. For example, upon determining that the final diagnostic profile indicates that the mass is benign but further care is provided, the image analysis system 65 may route the image (and containing document/report) to a user computing entity 30 associated with a healthcare provider. Upon determining that the final diagnostic profile indicates that further care is required (regardless of diagnosis), the image analysis system 65 may transmit the image (and including document/report) to a user computing entity 30 associated with a specialist and/or a user computing entity 30 associated with a user providing ancillary support. In certain embodiments, upon determining that the diagnosis indicates the mass is benign, the image analysis system 65 may route the image (and including document/report) to an Electronic Health Record (EHR) system.

Moreover, the image analysis system 65 may provide one or more image analysis tools, such as a user interface providing additional data regarding a determined diagnosis accompanying a mammograph. For example, the image analysis tools may provide a visual indication of relevance scores for each of a plurality of mass types (e.g., a benign cyst, a cancerous tumor, and/or the like), thereby providing an indication of mass type assigned to a detected mass within an image. The image analysis tools may additionally comprise one or more interactive user interface elements enabling a user to selectively apply one or more visual overlays to an analyzed image, such visual overlays may comprise a visual outline of a detected mass, a scaled grid having grid squares of a defined size to provide a visual indication of an absolute measurement corresponding with a detected mass. Moreover, as discussed above in reference to the lung nodule analysis, the image analysis tools may be configured to enable a user to selectively display one or more example images from the training data set to provide a visual comparison with images providing examples of known mass types that may be utilized by a user for confirmation of a determined mass type classification.

p. Nasal Deformity Example

Figure 25:
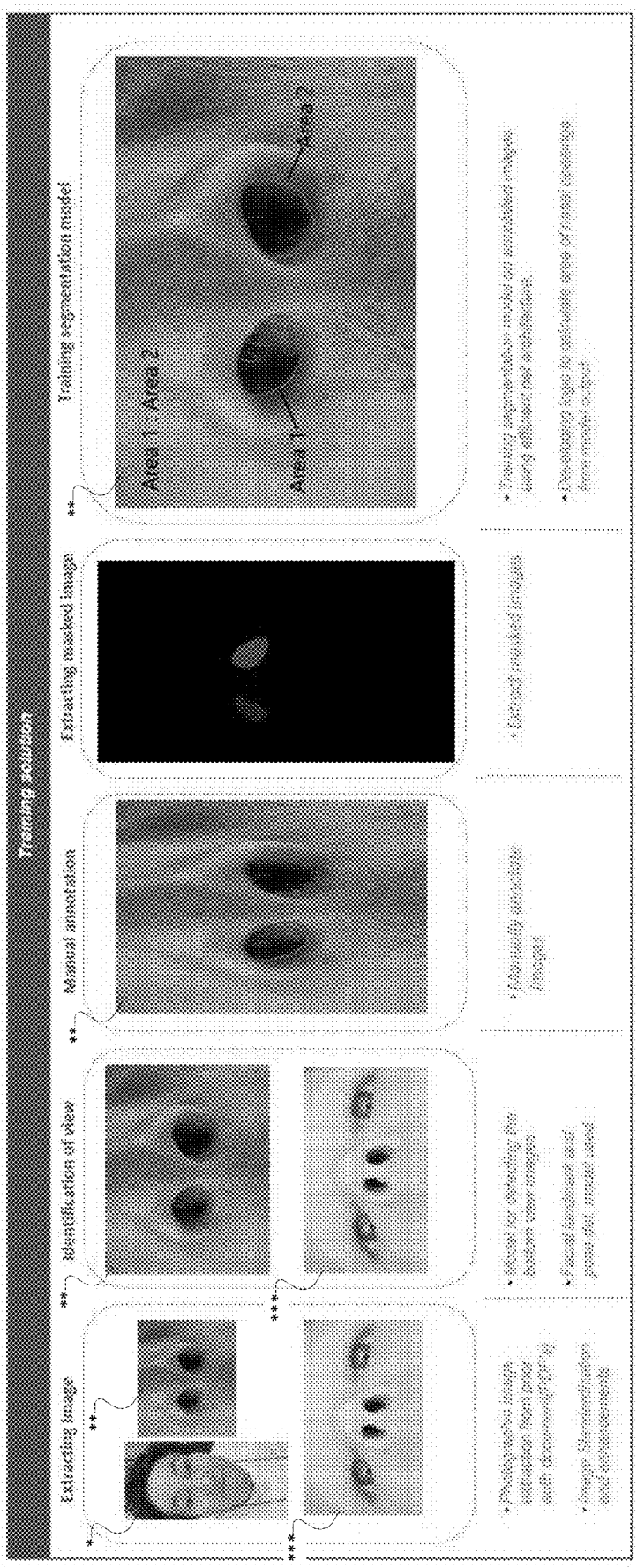
FIG. 25 illustrates example processes for detecting nasal deformities in accordance with certain embodiments.
Figure 26A:
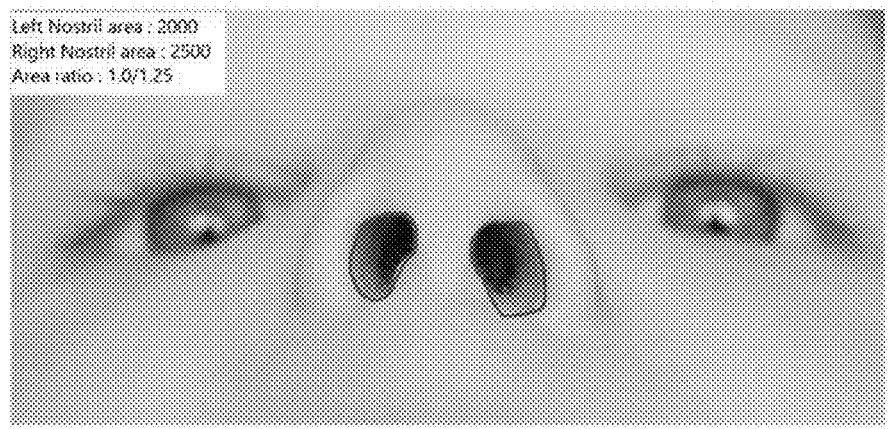
FIGS. 26A-26C illustrate example outputs of detections of nasal deformities in accordance with certain embodiments.
Figure 26B:
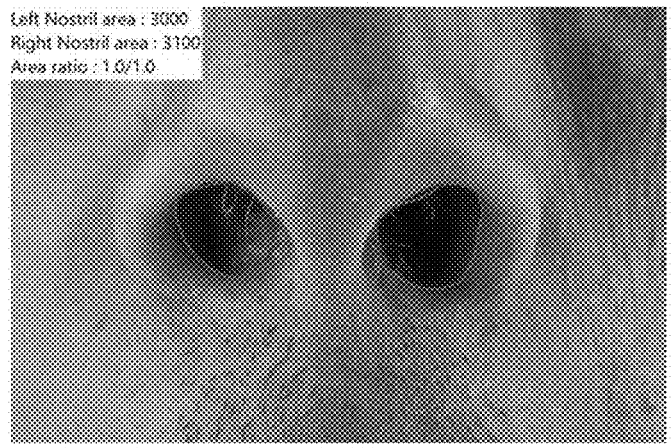
Figure 26C:
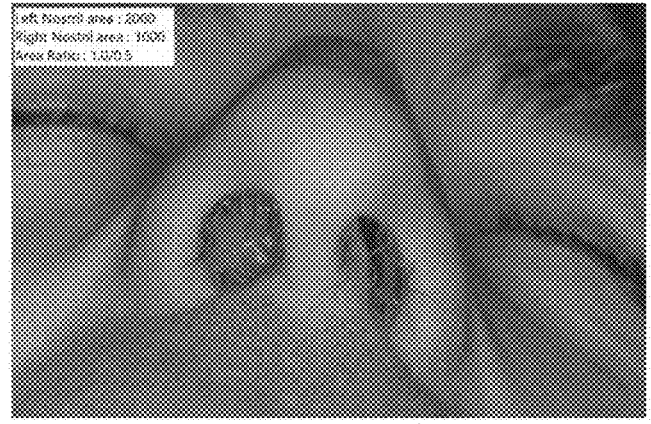

With reference to FIGS. 25-26C, the image analysis system 65 may be configured for automatically identifying a nasal opening deformity (e.g., a nasal opening collapse) that may be corrected through a rhinoplasty procedure (e.g., instances of nasal deformity and/or structural defects of the nose for which a rhinoplasty is a medical necessity for correction, for example, to alleviate breathing difficulties) utilizing an image analysis process.

As discussed in reference to the Blepharoptosis diagnosis process and other examples discussed above, the image analysis system 65 may first extract images provided for analysis, and to determine whether the images are of sufficient quality and content to enable a finding of structural deficiencies of the nose. Such images may be extracted from documents/reports or other data source files, as reflected at FIG. 25.

After extracting images from the source document (e.g., utilizing an edge detection algorithm based on a detected difference in color intensity between a generally white-background of a document and a darker colored background of a photograph, the image analysis system 65 may be configured to determine whether the photograph is of a sufficient size (e.g., in pixels) to enable an accurate determination of a finding of nose structural deficiency. Moreover, as discussed above, the image analysis system 65 may perform one or more image editing processes, such as image rotation, image sharpening, and/or the like to enable a more accurate determination of the location of edges of nasal openings and/or a determination of whether a user's nose has one or more structural deficiencies.

Once the image analysis system 65 has determined that the extracted image (examples of which are provided in FIGS. 25-26C) is of sufficient size and quality to enable a finding of nose structural deficiencies, the image analysis system may utilize one or more machine-learning based models for determining whether the content of the extracted image contains images of an underside of the patient's nose with sufficient clarity and orientation so as to enable an accurate assessment of whether the patient is suffering from structural deficiencies (e.g., collapse) of the nose, for which a rhinoplasty is a medical necessity. As just one example, the image analysis system 65 may utilize a convolutional neural network to compare the contents of the extracted images with an image training set to determine whether the extracted image matches images within the training set that are deemed sufficient to enable a finding of a structural deficiency of the nose. Accordingly, the image training set may comprise a plurality of images having corresponding image tags identifying those images as being of a sufficient quality and orientation to enable a determination of a finding of a nasal structural deficiency, and a plurality of images having corresponding image tags identifying those images as being of an insufficient quality and/or an insufficient orientation to enable a determination of a finding of a nasal structural deficiency.

With reference to FIG. 25, the image analysis system 65 applies a machine-learning based (e.g., convolutional neural network) nasal passage detection model to identify edges of the nasal passages identifiable within the image. The nasal passage detection models may be configured to identify features within portions of the image having a known nasal passage shape, to identify relationships between various expected nasal passage shapes reflected within the image to identify a likely location of the nasal passages within the image, to identify other shapes corresponding to features within the image having known spatial relationships to nasal passages (e.g., the shape and/or location of eyes, the shape and/or location of a tip of a nose, the shape and/or location of a bridge of a nose, visible between the patient's eyes, and/or the like), thereby enabling the automatic identification of nasal passages that do not have an expected nasal passage shape. As the image analysis system 65 may be configured to identify structurally deformed (e.g., collapsed) nasal passages, the image analysis system 65 utilizes a machine learning based model to identify nasal passages that does not require those nasal passages to have an expected shape.

The image analysis system 65 may then identify boundaries of each detected nasal passage, for example, utilizing edge detection methodologies for identifying changes in image color intensity around an area identified as encompassing a nasal passage. In certain embodiments, the image analysis system 65 is configured to generate an overlay (e.g., a color overlay, an image overlay, an outline overlay, and/or the like) having a shape size, and location corresponding with the identified location of each nasal passage within the image, utilizing the identified boundaries of the nasal passages to form the boundaries of the overlays. Examples of such overlays are provided in FIGS. 25 and 26A-26C. The location, size, and boundaries of each nasal passage may be stored (e.g. in metadata associated with the image) for further analysis. Additionally, as indicated in FIG. 25, the spatial relationship between identified nasal passages may be utilized to characterize one nasal passage as a "right" nasal passage, and another nasal passage as a "left" nasal passage, and the overlay of the right nasal passage may be provided with a first color (e.g., red), and the overlay of the left nasal passage may be provided with a second color (e.g., green), so as to enable a user to easily distinguish between each nasal passage overlay, even if the nasal passage overlays are provided in a user interface without the context of the original image utilized to generate the overlays.

As indicated in FIG. 25, the image analysis system 65 is configured to identify one or more characteristics of the identified image overlays, such as a relative location between the image overlays of the left nasal passage and the right nasal passage, relative sizes (e.g., area, length, width, and/or the like, such as measured in pixels) of each of the left nasal passage and the right nasal passage, and/or the like. Utilizing the identified characteristics, the image analysis system 65 may determine relative characteristics between the identified nasal cavities. As just one example with reference to FIG. 25, the image analysis system 65 may identify area measurements (e.g., in pixels) for each of the left nasal passage and the right nasal passage, and to determine a ratio of the areas between the left nasal passage and the right nasal passage. This determined area ratio may be compared against a reference area ratio (e.g., 1:1), indicating a normal ratio between the areas of nasal passages of human noses. Deviations from the reference area ratio may be indicative of a degree of nasal structural deficiency. It should be understood that a deviation from the reference ratio may be indicative of either a left nasal passage being larger than a right nasal passage, or a right nasal passage being larger than a left nasal passage, and therefore deviations from the example reference ratio of 1:1 in either direction (e.g., >1:1 or 1:>1) may be indicative of a deviation from the reference ratio that may be indicative of a medical necessity of a rhinoplasty.

As indicated, the image analysis system 65 may generate data indicative of a size (e.g., based on number of pixels, pixel-based area measurements, and/or the like) of the nasal passages. This nasal passage size data may be stored for further analysis in a memory storage area. The image analysis system 65 may comprise and utilize a nasal passage analysis engine encompassing machine-learning based (e.g., convolutional neural network based) models for determining whether a particular image is indicative of nasal structural deficiencies, such as a nasal cavity collapse. For example, the nasal analysis engine may utilize a training data set (e.g., a labeled training data set, such as a manually labeled training data set) to distinguish between those images demonstrating nose structural deficiencies for which a rhinoplasty is a medical necessity, and those images demonstrating lesser degrees of nose structural deficiencies (e.g., having no nose structural deficiencies) for which a rhinoplasty is not a medical necessity. Utilizing the provided training data, the nasal analysis engine may be configured to generate a threshold nasal passage area ratio that may be utilized as an image analysis criteria to classify newly received images as indicating a level of nasal structural deficiency for which a rhinoplasty procedure is a medical necessity, from those images that do not indicate a level of nasal structural deficiency for which a rhinoplasty procedure is a medical necessity. As indicative above, deviations from a reference ratio may be indicative of either a left nasal passage being larger than a right nasal passage, or a right nasal passage being larger than a left nasal passage, and therefore the threshold nasal passage area ratio may identify a relative difference between areas of the left nasal passage and the right nasal passage, rather than a defined minimum ratio value. As non-limiting examples, the threshold nasal passage area ratio may identify a relative difference in area of 200% between nasal passages, and such a relative difference may be satisfied by a ratio of 2:1, 1:2, 1:0.5, or 0.5:1.

However, it should be understood that the nasal analysis engine may identify other (alternative or additional) criteria for distinguishing between those images indicative of a necessity of a rhinoplasty from those images that are not indicative of a necessity of a rhinoplasty, such as an identified relative distance between nasal passages (e.g., a distance, in pixels, between nasal passages relative to a size (e.g., a width, measured in pixels) of one or more nasal passages), a distance between a nasal passage (e.g., measured in pixels) relative to another identified feature within an image relative to a size (e.g., a width, measured in pixels) of one or more nasal passages, and/or the like.

Upon determining whether the embedded image satisfies nasal structural deficiency finding criteria (e.g., determining the medical necessity of a rhinoplasty), the image analysis system 65 assigns diagnosis data to be associated with the embedded image (and/or the documents/reports comprising the embedded image). The image analysis system 65 may thus generate and transmit data indicative of the resulting automatically generated diagnosis to the user computing entity 30 providing the embedded image, and may provide the document/report containing the embedded image, together with the embedded image (which may be annotated, such as with a visual overlay of the nasal passage, as well as a visual indication of the ratio between the nasal passage areas (e.g., as indicated in FIGS. 26A-26C). The images provided in FIGS. 26A-26C are example outputs of certain embodiments, including visual overlays of identified nasal passages and indications of size ratios between identified nasal passages.

As discussed in the Blepharoptosis analysis above, based on a determination of whether a rhinoplasty is a medical necessity, the image analysis system 65 may route the embedded image (e.g., together with the document/report containing the embedded image) to an appropriate user computing entity 30 for final approval of the determined diagnosis. For example, upon determining that a rhinoplasty is a medical necessity, the embedded image (e.g., together with the document/report containing the embedded image) may be routed to a first user computing entity (e.g., operated by a nurse) for approval, and upon determining a rhinoplasty is not a medical necessity, the embedded image (e.g., together with the document/report containing the embedded image) may be routed to a second user computing entity 30 (e.g., operated by a physician) for evaluation.

Moreover, the image analysis system 65 may provide one or more image analysis tools, such as a user interface having a plurality of user input elements configured to enable a user to selectively apply one or more overlays to the embedded image that are indicative of the results of the medical necessity of the rhinoplasty analysis (e.g., based on determined characteristics of the detected nasal passages within the embedded image). As mentioned above, the image analysis system 65 may be configured to generate a visual overlay that may be selectively applied or removed from the embedded image to indicate the size, shape, and location of each of the identified nasal passages. Moreover, the image analysis tool may automatically calculate an area ratio between the identified nasal passages, and to display the calculated area ratio within the embedded image as indicated in the example visual displays of FIGS. 26A-26C.

q. Additional Spinal Analysis Example

As noted above, the image analysis system 65 may be configured for executing one of a plurality of image analysis processes, which may be selected based at least in part on user input, based at least in part on detected features within an image, based at least in part on detected text within a report/document containing the image, and/or the like. In addition to the above-mentioned example of analyzing X-ray images of a patient's spine for a scoliosis diagnosis, the image analysis system 65 may be additionally configured for analyzing certain X-ray images of a patient's spine for other analyses, such as for determining whether vertebrae show indications of thinning, for determining whether spinal disks show indications of thinning, and/or for determining whether a spinal canal shows indications of constriction.

As discussed in reference to the various examples provided above, the image analysis system 65 may first extract images provided for analysis, and to determine whether the images are of sufficient quality and content to enable a determination of desired characteristics of the patient's spine. The image analysis system 65 may be configured to implement a pre-processing and image quality check process analogous to that discussed above in reference to the mentioned scoliosis analysis example.

After extracting images from a containing document (e.g., utilizing an edge detection algorithm based on a detected difference in color intensity between a generally white-background of a document and a generally-black background of an X-ray image), the image analysis system 65 may be configured to determine whether the X-ray image is of a sufficient size (e.g., in pixels) to enable an accurate determination of a desired characteristic of the patient's spine (e.g., vertebrae thickness, disk thickness, and/or spinal canal thickness). Moreover, as discussed above, the image analysis system 65 may perform one or more image editing processes, such as image rotation, image sharpening, and/or the like to enable a more accurate determination of certain characteristics of the patient's spine. However, it should be understood that certain image analysis processes, including feature detection processes as discussed herein, may be orientation agnostic, so as to be able to perform appropriate image analysis regardless of the orientation of the extracted image.

Once the image analysis system 65 has determined that the image is of sufficient size and quality to enable a determination of one or more desired characteristics of the patient's spine, and upon determining that the image is of a sufficient orientation to enable a spinal characteristic analysis, the image analysis system 65 may utilize one or more machine-learning based models (e.g., classification models) for determining whether the content of the extracted image contains images of a patient's spine with sufficient clarity, content, and orientation so as to enable an accurate assessment of the various characteristics of the patient's spine. As just one example, the image analysis system 65 may utilize a convolutional neural network to compare the contents of the extracted images with an image training set to determine whether the extracted images match images within the training set that are deemed sufficient to enable a desired analysis of the patient's spine. As discussed in reference to FIG. 20A, above (discussing a scoliosis diagnosis example), and with further reference to FIG. 27, the image analysis system 65 applies a machine-learning based (e.g., convolutional neural network) spinal detection model to identify the spine and to classify certain features thereof within the image. The spinal detection model may be configured to identify portions of the image having a known spinal shape (e.g., given an orientation of the spine relative to the imager used to generate the image), to identify known relationships between various expected shapes represented within the X-ray image (e.g., expected changes in diameter of a spinal canal proximate top and bottom ends of the spine; expected numbers of detected vertebrae within the image, detected orientation of vertebrae relative to a detected spinal canal, and/or the like). By identifying certain features and relationships between those certain features, the image analysis system 65 is configured to determine whether the image is of a proper content and orientation of the spine to enable further analysis and classification of features identified therein. Specifically in reference to the image of FIG. 27, the image analysis system 65 is configured to determine whether the image is a mid-sagittal view of the patient's spine. After determining that an image is of an appropriate quality and content to enable one or more analyses of the patient's spine, in certain embodiments the image analysis system 65 may be configured to crop an image to specifically focus on areas of the image within which the measured vertebrae are located.

In certain embodiments, the identified spinal shape may be identified as having a color intensity deviation of less than a defined threshold percentage. The acceptable color intensity deviation may be identified by an appropriate machine-learning based model trained via a training data set in which the spine is identified in each image within the training data set, thereby enabling the machine-learning model to identify color intensity deviations within the indicated boundaries of an identified spine within each image of the training data set, so as to establish a maximum color deviation likely to be indicative of a continuous spine. The maximum color deviation may accommodate differences in color intensity in the X-ray image due at least in part to the presence of cartilage disks between individual bone vertebrae of the spine.

Figure 27:
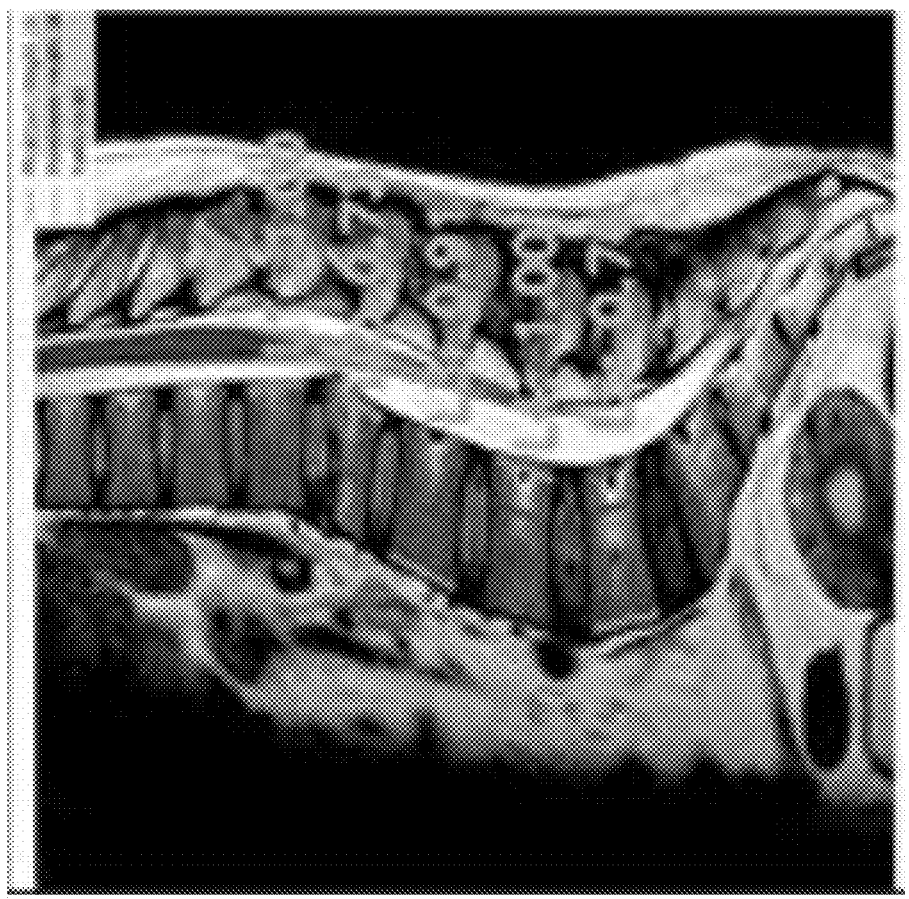
FIG. 27 illustrates an example mid-sagittal X-rays spinal view for classifying images according to vertebrae thinning in accordance with certain embodiments.

FIG. 27 additionally illustrates the graphical output resulting from just one example analysis of an image of a patient's spine. Once the image analysis system 65 determines that an image is sufficient for measuring vertebrae thickness, the image analysis system 65 may utilize the above-noted differences in color intensity to identify the individual boundaries of each vertebrae. Any of a variety of methodologies may be utilized for identifying individual vertebrae. Certain embodiments may execute processes for identifying individual vertebrae without further image manipulation. However, in other embodiments, the image analysis system 65 may generate one or more binary image masks based on detected intensity differences within regions of the image within identified boundaries of the spine. The binary masks may thus emphasize the boundaries of each vertebrae, which may then be utilized to identify the location of each vertebrae boundary. Moreover, in certain embodiments, the image analysis system 65 may additionally utilize a machine-learning based vertebrae detection model to label each vertebrae. As just one example, the vertebrae detection model may utilize a labeled training data set in which each of a plurality of vertebrae within each image are individually labeled to uniquely identify each vertebrae visible within the image. The image analysis system 65 may then utilize this training data to review the embedded image provided for analysis to individually identify each vertebrae within the provided image. As examples, criteria utilized for identifying and labeling each vertebrae may comprise relative location-based criteria (e.g., relative location within the overall image, relative location compared with other identified vertebrae, relative location compared with other identified features of the image, and/or the like). By identifying labels for each vertebrae, later analysis (e.g., thickness ratio measurements of each vertebrae, thickness ratio measurements of disks between vertebrae, and/or the like) may be correlated with the vertebrae labels, such that generated graphical user interfaces may provide information regarding calculated aspects of the image with respect to relevant vertebrae labels.

As a part of identifying each vertebrae and to provide additional analysis thereof, the image analysis system 65 may identify a vertical edge of each vertebrae and may denote the identified vertical edge with a line (e.g., a green line in the image of FIG. 27). The vertical edge may be identified and a height (e.g., in pixels) of the identified vertical edge may be determined within the image. The image analysis system 65 may then scan across each identified vertebrae to identify a thinnest portion (in height, measured by pixels) of each vertebrae, and the image analysis system 65 may denote the identified thinnest point with a second line (e.g., a red line in the image of FIG. 27). The image analysis system 65 may then classify each vertebrae by calculating a thickness ratio for each vertebrae using relative measurements between the identified vertical edge (selected based at least in part on an assumption that the vertical edge is likely the thickest point of the vertebrae) and the identified thinnest point of the vertebrae, and the image analysis system 65 may generate an overlaid indication of a thickness ratio for each vertebrae.

Based on the determined thickness ratio between the vertical edge of a detected vertebrae and a thinnest portion of the detected vertebrae, the image analysis system 65 may execute one or more threshold based models for classifying each vertebrae by determining whether the vertebrae demonstrate significant thinning that may be indicative of listhesis, that may be indicative of a need for Total Artificial Disk Replacement (TADR). For example, a threshold-based model may indicate that a calculated thickness ratio below an established threshold may be designated as indicating a significant thinning of the vertebrae for which the thickness ratio falls below the threshold, whereas a thickness ratio above the established threshold does not demonstrate significant thinning of the vertebrae. It should be understood that the established ratio may be applicable to all vertebrae visible within the X-ray image, or separate, vertebrae specific established thresholds may be utilized for each vertebrae (e.g., a first established threshold utilized for the L1 vertebrae, a second established threshold utilized for the L2 vertebrae, and/or the like).

Upon determining whether any of the calculated thickness ratios for vertebrae visible within the X-ray image satisfies an established threshold (e.g., being below the established threshold), the image analysis system 65 assigns diagnosis data to be associated with the embedded image (and/or the documents/reports comprising the embedded image). The image analysis system 65 may thus generate and transmit data indicative of the resulting classification and automatically generated thickness ratios for each vertebrae visible within the X-ray image, as well as an indication of which vertebrae (if any) fall below an established threshold. Such diagnosis data may be utilized, for example, for preapproval of a TADR procedure for the patient. The image analysis system 65 may transmit the generated diagnosis data to the user computing entity 30 providing the embedded image, and may provide the document/report containing the embedded image, together with the embedded image (which may be annotated, such as with a visual overlay of the identified vertebrae, the locations within each vertebrae utilized for calculating a thickness ratio, and/or the calculated thickness ratio for each vertebrae).

As discussed in reference to the examples above, based on a determination of whether any of the vertebrae thickness ratios satisfy applicable thresholds, the image analysis system 65 may route the embedded image (e.g., together with the document/report containing the embedded image) to an appropriate user computing entity 30 for final approval of the determined designation of thinning of each visible vertebrae. For example, upon a determination that at least one vertebrae demonstrates significant thinning, the embedded image (e.g., together with the document/report containing the embedded image) may be routed to a first user computing entity 30 (e.g., operated by a nurse) for approval, and upon determining that none of the vertebrae visible within the X-ray image demonstrate significant thinning, the embedded image (e.g., together with the document/report containing the embedded image) may be routed to a second user computing entity 30 (e.g., operated by a physician) for approval.

Figures 28A, 28B:
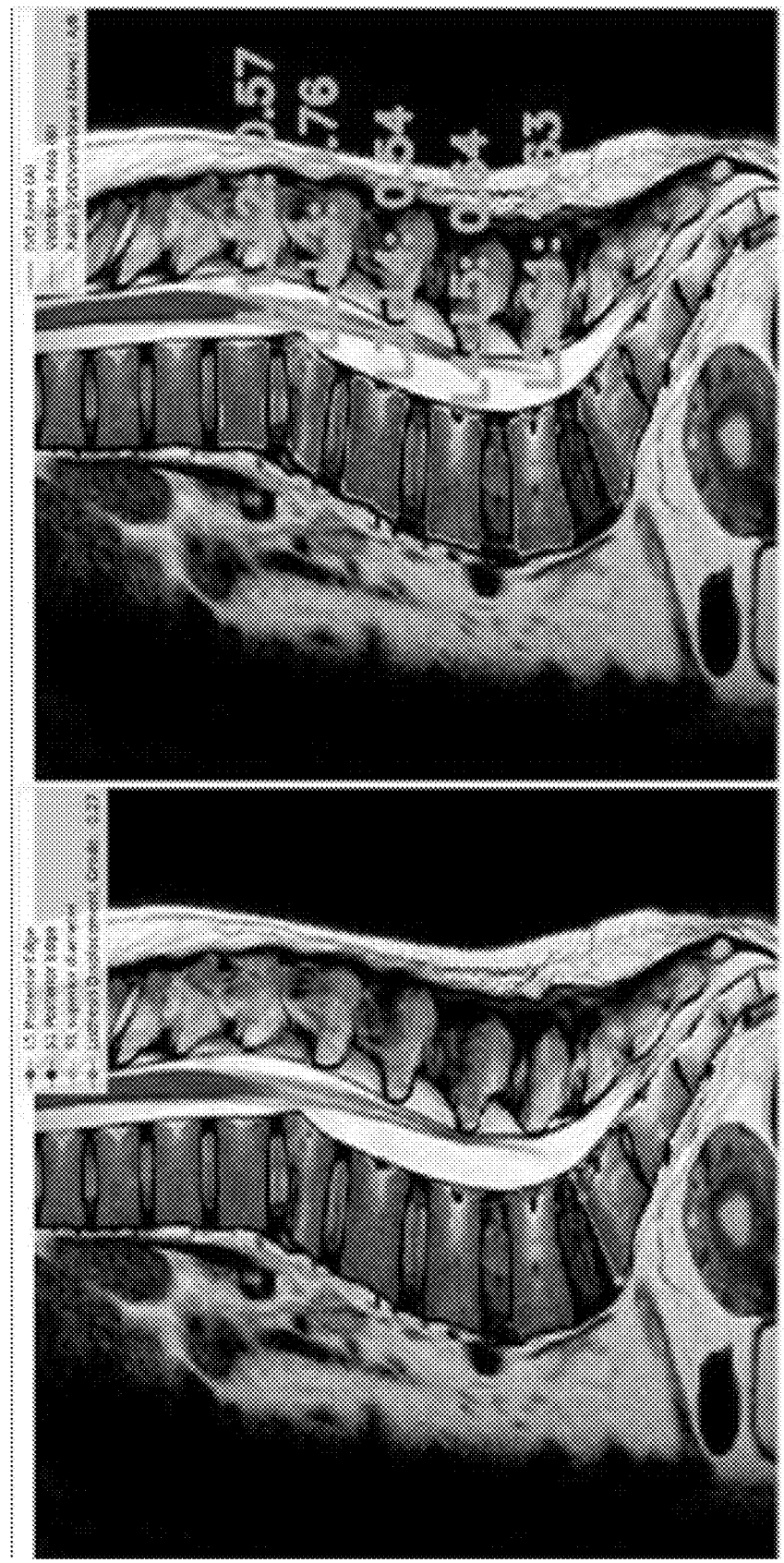
FIGS. 28A-28B illustrate example mid-sagittal X-rays spinal views for classifying images according to disk thinning in accordance with certain embodiments.

FIGS. 28A-28B illustrate another example analysis of a patient's spinal X-ray that may be performed by the image analysis system 65. The analysis illustrated in FIGS. 28A-28B may utilize images analogous to those discussed in reference to FIG. 27 (e.g., a mid-sagittal view). FIGS. 28A-28B specifically focus on detection of thinning of spinal disks located between detected vertebrae, and accordingly the detected size and locations of each of the detected vertebrae may be utilized for detecting whether any of the disks located between vertebrae demonstrate significant thinning. However, as the features for detection within the image are identical to those discussed in reference to FIG. 27, the image analysis system 65 may execute analogous processes for ensuring the image is of appropriate quality and content for enabling such analysis, and for identifying and/or labelling vertebrae (and other features) within the image.

FIG. 28A illustrates just one example of a graphical output resulting from an example analysis of an image of a patient's spine. Once the image analysis system 65 determines that an image is sufficient for measuring sizes of vertebrae disks, the image analysis system 65 may identify certain boundaries and/or other measurements to be utilized for classifying vertebrae disks by calculating vertebrae disk size ratios (e.g., ratios of sizes between a disk and an adjacent vertebrae). As shown in FIG. 28A, the image analysis system 65 identifies vertical edges of adjacent vertebrae (indicated by the red line and the dark blue line in FIG. 28A), as well as a horizontal edge of a lower vertebrae of the adjacent vertebrae (indicated by the yellow line in FIG. 28A). The image analysis system 65 may additionally identify a listhesis displacement point (indicated with a cyan point in FIG. 28A) that may be utilized as a reference point for measuring disk thickness (e.g., in pixels) within the image. Utilizing the relative location of each of the detected features of adjacent vertebrae, the image analysis system 65 may be configured to utilize relative measurement techniques to determine whether the image demonstrates features indicative of a listhesis diagnosis (e.g., based on generated measurement ratios between various measurements). Upon determining whether the image is indicative of a listhesis diagnosis, the image analysis system 65 may be configured to assign diagnosis data to the image (and the document/report including the embedded image) indicative of whether the image is subject to a positive listhesis diagnosis (indicating presence of listhesis) or a negative listhesis diagnosis (indicating no evidence of listhesis). As discussed in reference to FIG. 27 above, the image and the document/report containing the image may be routed to one of a plurality of available user computing entities 30 (e.g., a first user computing entity 30 or a second user computing entity 30) for approval or denial of claims submitted with the documents. Moreover, the diagnosis data may be further transmitted to the user computing entity 30 that originally submitted the documentation with the embedded image, so as to provide the submitting user with an indication of whether the image data shows evidence of listhesis.

FIG. 28B illustrates another example analysis that may be performed on a patient's spinal image according to certain embodiments. Once the image analysis system 65 determines that an image is sufficient for identifying edges of each vertebrae within an image, the image analysis system 65 may utilize the above-noted differences in color intensity to identify the individual boundaries of each vertebrae. Any of a variety of methodologies may be utilized for identifying individual vertebrae without further image manipulation. However, as discussed above, binary mask-based analysis may be utilized to identify boundaries of vertebrae in accordance with certain embodiments. Moreover, as discussed above, the image analysis system 65 may additionally utilize a machine-learning based vertebrae detection model to label each vertebrae, as discussed above.

As a part of identifying each vertebrae and to provide additional analysis thereof, the image analysis system 65 may identify edges of each vertebrae that are adjacent to disks (in red lines, as shown in FIG. 28B), and edges of each vertebrae that are not adjacent to disks (in green lines, as shown in FIG. 28B). As illustrated in FIG. 28B, the image analysis system 65 may additionally identify boundaries of disks between adjacent vertebrae (as indicated by the orange lines in FIG. 28B), such that an area of each vertebrae and an area of each disk (calculated in square pixels) may be calculated, such that a relative measurement technique may be utilized for calculating a ratio as to the area of a disk relative to the area of each adjacent vertebrae that may be utilized as a classification of each disk. The image analysis system 65 may generate an overlaid indication of a disk-to-vertebra area ratio for each disk (each disk may be characterized by two ratios, one ratio relative to a vertebrae above the disk and one ratio relative to a vertebrae below the disk).

Based on the determined area ratio determined for each disk, the image analysis system 65 may execute one or more threshold models for classifying the disks by determining whether the disks demonstrate significant thinning that may be indicative of a need for a vertebroplasty procedure. For example, a threshold-based model may indicate that a calculated area ratio below an established threshold may be designated as indicating a significant thinning of the disk for which the area ratio falls below the threshold, whereas an area ratio above the established threshold does not demonstrate significant thinning of the disk. It should be understood that the established ratio may be applicable to all disks visible within the X-ray image, or separate, disk specific established thresholds may be utilized for each disk (e.g., a first established threshold utilized for the disk between the L1-L2 vertebrae, a second established threshold utilized for the disk between the L2-L3 vertebrae, and/or the like).

Upon determining whether any of the calculated area ratios for the disks visible within the X-ray image satisfies an established threshold (e.g., being below the established threshold), the image analysis system 65 assigns diagnosis data to be associated with the embedded image (and/or documents/reports comprising the embedded image). The image analysis system 65 may thus generate and transmit data indicative of the resulting automatically generated area ratios for each disk visible within the X-ray image, as well as an indication of which disk (if any) fall below the established threshold. Such diagnosis data may be utilized, for example, for preapproval of a vertebroplasty procedure for the patient. The image analysis system 65 may transmit the generated diagnosis data to the user computing entity 30 providing the embedded image, and may provide the document/report containing the embedded image, together with the embedded image (which may be annotated, such as with a visual overlay of the identified disks, the boundaries of vertebrae and disks utilized for calculating area ratios, and/or the like).

As discussed in reference to the examples above, based on a determination of whether any of the disk area ratios satisfy applicable thresholds, the image analysis system 65 may route the embedded image (e.g., together with the document/report containing the embedded image) to an appropriate user computing entity 30 for final approval of the determined designation of thinning of each visible disk. For example, upon a determination that at least one disk demonstrates significant thinning, the embedded image (e.g., together with the document/report containing the embedded image) may be routed to a first user computing entity 30 (e.g., operated by a nurse) for approval, and upon determining that none of the disks visible within the X-ray image demonstrate significant thinning the embedded image (e.g., together with the document/report containing the embedded image) may be routed to a second user computing entity 30 (e.g., operated by a physician) for approval.

Figure 29:
FIG. 29 illustrates another example mid-sagittal X-ray spinal view for classifying images according to spinal canal restrictions in accordance with certain embodiments.

FIG. 29 illustrates yet another example analysis of a patient's spinal X-ray that may be performed by the image analysis system 65. The analysis illustrated in FIG. 29 may utilize images analogous to those discussed in reference to FIGS. 27-28B (e.g., a mid-sagittal view). FIG. 29 specifically focuses on detection of a constriction of a spinal canal extending adjacent to the spinal vertebrae for classification of features within the embedded image. To classify whether a patient's spinal canal demonstrates constriction, measurements of the width of the patient's spinal canal (in pixels within the image)—representative of the diameter of the patient's spinal canal—may be performed at a plurality of locations along the length of the detected spinal canal and relative measurement techniques may be utilized to calculate ratios between multiple measurements, and the calculated ratios may be utilized to determine whether spinal canal constriction is present. For convenience of automatically classifying the measurement locations along the length of the spinal canal, the measurements may be taken at locations approximately centrally located relative to adjacent vertebrae and disks, and those locations may be designated in a graphical overlay placed onto the image, as discussed herein.

To identify widths (measured in pixels) of the spinal canal visible within the embedded image at various locations along the length of the spinal canal, the image analysis system 65 identifies boundaries of the spinal canal within the image. Once the image analysis system 65 determines that an image is sufficient for classifying the spinal canal by measuring various widths of the spinal canal, the image analysis system 65 may identify certain boundaries and/or other measurements to be utilized for determining a width of the spinal canal, as well as for assigning location labels for the calculated spinal canal widths. Accordingly, the image analysis system 65 may utilize one or more machine-learning based models (e.g., classification models) for identifying individual boundaries of each vertebrae and the spinal canal. Certain embodiments may execute processes for identifying individual vertebrae and for identifying the spinal canal without further image manipulation. However, in other embodiments, the image analysis system 65 may generate one or more binary image masks based on detected intensity differences within regions of the image within identified boundaries of the spine. The binary masks may thus emphasize the boundaries of each vertebrae and/or the boundaries of the spinal canal, which may then be utilized to identify the location of each vertebrae boundary and the spinal canal boundaries. Moreover, the image analysis system 65 may additionally utilize a machine-learning based vertebrae detection model to label each vertebrae (so as to enable a labelling of locations where the width of the spinal canal is measured).

As a part of identifying each vertebrae, the image analysis system 65 may identify boundaries of each vertebrae, thereby enabling a determination of a centerline of each vertebrae such that measurements of the spinal canal may be taken at a location at least substantially aligned with the locations of centerlines of each vertebrae. Similarly, boundaries of each vertebrae may be utilized for estimating centerlines of disks between vertebrae (based on a central location between adjacent bottom and top edges of adjacent vertebrae), such that measurements of the spinal canal may be taken at a location at least substantially aligned with the locations of centerlines of each disk. When performing the width measurements of the spinal canal, each of these identified locations (including the centerline of specific vertebrae and the centerline of specific disks) may be labeled with a graphical overlay on the image to facilitate analysis of the data provided with the image.

Utilizing the identified locations of centerlines of vertebrae and disks within the image, the image analysis system 65 is configured to draw a line across the width of the spinal canal at each of these locations, and to provide a label for each of these lines corresponding to the vertebrae or disk location where the lines are drawn. The lines are drawn parallel and aligned with the determined centerlines of the vertebrae and disks, and the lines are draw such that opposite ends of the lines are located at the detected edges of the spinal canal. The image analysis system 65 then calculates a length (in pixels) of each generated line, and the image analysis system 65 generates two length ratios for each drawn line (with the exception of the top-most line and the bottom-most line, for which only a single ratio is calculated). These length ratios are calculated to compare the lengths of each generated line with the lengths of the adjacent lines. With reference to the example of FIG. 29, for the line labelled L1 (corresponding to a location adjacent the L1 vertebrae), a single ratio is calculated, comparing the L1 line against the L1_L2 line (the line immediately below the L1 line, that is aligned with the disk located between the L1 and L2 vertebrae). No other ratios are calculated since no other lines are adjacent the L1 line. For the line labeled L1_L2, two ratios are calculated, a first ratio comparing the L1_L2 line against the L1 line length, and a second ratio comparing the L1_L2 line against the L2 line length (the line immediately adjacent and below the L1_L2 line). By generating these length ratios for each generated line, the image analysis system 65 is configured to detect changes in width of the spinal canal at various locations along the length of the spinal canal.

The image analysis system 65 may be configured to utilize an established length ratio threshold for determining whether spinal canal width changes at one or more locations along the length of the spinal canal are indicative of constriction of the spinal canal. It should be understood that a single established length ratio threshold may be utilized along the entirety of the length of the spinal canal, or a plurality of established length ratio thresholds may be utilized, with each established length ratio threshold being applicable to a particular location along the length of the spinal canal.

Upon determining whether any of the calculated length ratios for the spinal canal locations visible within the X-ray image satisfy an established length ratio threshold (e.g., being above the established threshold or being below the established threshold, as specified with respect to a particular threshold), the image analysis system 65 assigns diagnosis data to be associated with the embedded image (and/or the documents/reports comprising the embedded image). The image analysis system 65 may thus generate and transmit data indicative of the classification of the spinal canal and resulting automatically generated length ratios for each line across the width of the spinal canal visible within the X-ray image, as well as an indication of which line (if any) satisfies an applicable length ratio threshold. Such diagnosis data may be utilized, for example, for approval of procedures to address spinal canal construction for the patient. The image analysis system 65 may transmit the generated diagnosis data to the user computing entity 30 providing the embedded image, and may provide the document/report containing the embedded image, together with the embedded image (which may be annotated, such as with a visual overlay illustrating the locations where the widths of the spinal canal are measured).

As discussed in reference to the examples above, based on a determination of whether any of the length ratios generated for widths of any locations along the length of the spinal canal satisfy applicable thresholds, the image of analysis system 65 may route the embedded image (e.g., together with the document/report containing the embedded image) to an appropriate user computing entity 30 for final approval of the determined designation of constriction of the spinal canal. For example, upon a determination that at least one location along the length of the spinal canal demonstrates constriction, the embedded image (e.g., together with the document/report containing the embedded image) may be routed to a first user computing entity (e.g., operated by a nurse) for approval, and upon determining that none of the locations along the length of the spinal canal demonstrate constriction, the embedded image (e.g., together with the document/report containing the embedded image) may be routed to a second user computing entity (e.g., operated by a physician) for approval.

r. Panniculectomy Example

As noted above, the image analysis system 65 may be configured for executing one of a plurality of image analysis processes, which may be selected based at least in part on user input, based at least in part on detected features within an image, based at least in part on detected text within a report/document containing the image, and/or the like. In certain embodiments, the image analysis system 65 is configured for analyzing photographs of a patient's torso for estimation of the location of the patient's pubic symphysis and a location of a lower edge of a patient's hanging abdominal panniculus.

As discussed in reference to the various examples provided above, the image analysis system 65 may first extract images provided for analysis, and to determine whether the images are of sufficient quality and content to enable a determination of an estimated location of the patient's pubic symphysis (e.g., based on a detected widest part of the patient's hips) and a determination of a lower edge of a patient's hanging panniculus. The image analysis system 65 may be configured to implement a pre-processing and image quality check process analogous to that discussed in reference to other photograph-based examples discussed above.

After extracting images from a containing document (e.g., utilizing an edge detection algorithm based on a detected difference in color intensity between a generally white-background of a document and a colored background of a photograph), the image analysis system 65 may be configured to determine whether the photograph is of a sufficient size (e.g., in pixels) to enable an accurate detection of the location of a patient's pubic symphysis and hanging abdominal panniculus. Moreover, as discussed above, the image analysis system 65 may perform one or more image editing processes, such as image rotation, image sharpening, and/or the like to enable a more accurate detection of the patient's pubic symphysis and hanging abdominal panniculus. However, it should be understood that certain image analysis processes, including feature detection processes as discussed herein, may be orientation agnostic, so as to be able to perform appropriate image analysis regardless of the orientation of the extracted image.

Figure 30:
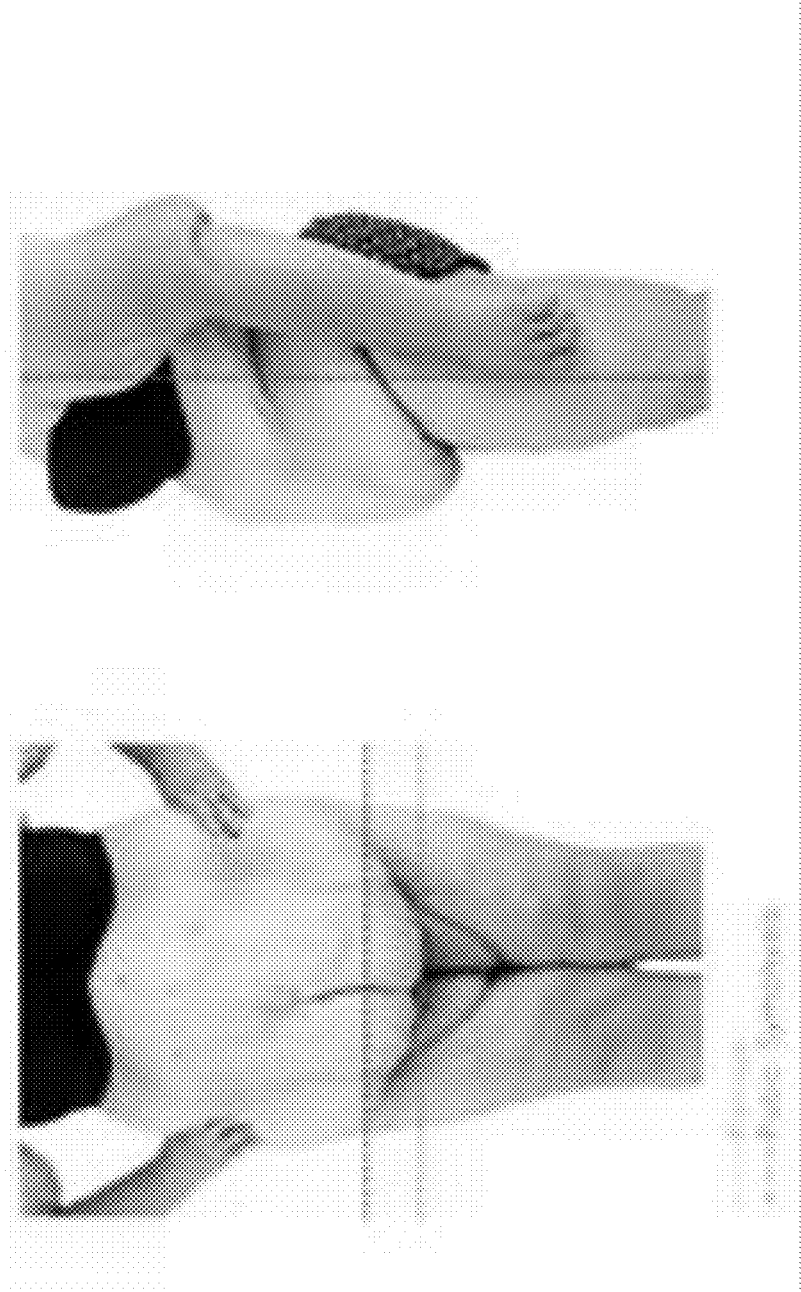
FIG. 30 illustrates torso images views in accordance with certain embodiments.

Once the image analysis system 65 has determined that the image is of sufficient size and quality to enable a detection of an estimated location of the patient's pubic symphysis and hanging abdominal panniculus, and upon determining that the image is of a sufficient orientation to enable an analysis of the location of the hanging abdominal panniculus, the image analysis system 65 may utilize one or more machine-learning based models (e.g., classification models) for determining whether the content of the extracted image contains images of a patient's torso with sufficient clarity, content, and orientation so as to enable an accurate assessment of an estimated location of the patient's pubic symphysis and hanging abdominal panniculus. As just one example, the image analysis system 65 may utilize a convolutional neural network to compare the contents of the extracted images with an image training set to determine whether the extracted images match images within the training set that are deemed sufficient to enable a desired analysis of the patient's torso. For example, the classification model may be configured to determine whether a sufficient proportion of the patient's torso is shown in the photograph, such as extending between at least the patient's shoulders/neck to the patient's knees or lower thighs. By identifying certain features and relationships between those certain features, the image analysis system 65 is configured to determine whether the image is of a proper content and orientation to enable further analysis. Moreover, as indicated at FIG. 30 (which includes an annotated version of images provided for analysis, the annotations are discussed in greater detail below), the image analysis system 65 may look for a frontal and side-view of the patient's torso. The image analysis system 65 may utilize one or more machine-learning based models to implement relative measurement techniques to compare the patient's torso positioning (e.g., slouched, straight, bent, arched, and/or the like) within the frontal and side-views to determine whether the patient has at least substantially the same posture in both frontal and side-view images. Moreover, the image analysis system 65 identifies and overlays a posture detection line in the side-view image. This posture detection line need not utilize any absolute measurement-based criteria, and may instead utilize relative measurement techniques to be compared against a posture criteria for further analysis. Because the bottom edge location of a hanging abdominal panniculus relative to a pubic symphysis varies as the patient bends at the waist, the posture detection line and posture criteria may be compared to ensure the patient is standing sufficiently straight to enable an accurate assessment of the size of the patient's hanging abdominal panniculus. Upon determining that the detected posture line does not satisfy the posture criteria, such as based on a determination that the posture line reflects a bend in the patient's waist of a sufficiently large angle that an accurate assessment of the relative location of the patient's hanging abdominal panniculus relative to the pubic symphysis cannot be achieved, the image analysis system 65 may generate a notification to a user computing entity 30 indicating that the provided images are unacceptable for further analysis. In certain embodiments, the posture criteria may specify a maximum bend angle (e.g., measured at an angle centered on the patient's hips in the side-view of the patient's torso) for satisfaction of the posture criteria. Accordingly, if the patient's torso is bent beyond the maximum bend angle (as determined by an analysis of a bend angle within the annotated torso detection line, as reflected in FIG. 30, for example), the image analysis system 65 determines that the images do not satisfy the posture criteria. As yet another example, the posture criteria may specify that the frontal view and the side-view should reflect an approximately equivalent posture so as to enable an appropriate determination of the patient's hanging abdominal panniculus. Utilizing a machine-learning based model to identify features visible within each of the frontal and side-views, so as to detect the relative locations of those identified features, the image analysis system 65 determines whether the patient's torso is at a substantially similar posture (e.g., based on a determination that the relative distances (e.g., measured in pixels) between detected features within the frontal and side-views are approximately identical (e.g., within some defined tolerance of numbers of pixels)) so as to determine whether an accurate assessment of the location of the patient's hanging abdominal panniculus may be achieved. If the image analysis system 65 determines that the posture criteria are not completely satisfied, the image analysis system 65 may reject the images from further analysis.

As mentioned, FIG. 30 illustrates an example graphical output resulting from an example analysis of the patient's torso. Once the image analysis system 65 determines that an image is sufficient for approximating the location of a patient's pubic symphysis and hanging abdominal panniculus, the image analysis system 65 may utilize a machine-learning based model for identifying and classifying specific features within the image, such as a widest point of the patient's hips, a lower edge of a patient's hanging abdominal panniculus, and/or the like. Any of a variety of methodologies may be utilized for identifying boundaries of the various identified features. Certain embodiments may execute processes for identifying boundaries of the identified features without further image manipulation. In other embodiments, the image analysis system 65 may utilize image manipulation (e.g., changing image contrast) to emphasize feature boundaries, so as to identify precise locations of boundaries of specific features.

To identify the approximate location of the pubic symphysis, the image analysis system 65 identifies the boundaries of the patient's torso and measures a horizontal distance across the patient's torso between identified boundaries of the patient's torso so as to determine a widest point of a patient's hips. As a part of identifying a widest point of the patient's hips, the image analysis system 65 is further configured to utilize a machine-learning based model to approximate a boundary between the patient's hips and the patient's abdomen so as to avoid false positive determinations of a widest point of the patient's hips in the event the widest point of the patient's torso is located within the patient's abdomen, shoulders, or elsewhere outside of the patient's hips. As reflected in FIG. 30, the image analysis system 65 is configured to generate an annotated line at the detected widest point of the patient's hips (as shown with the red dashed horizontal line of FIG. 30) to reflect the results of the machine-learning based identification of this point. This widest point of the patient's hips is used clinically to approximate the location of the patient's pubic symphysis, without additional imaging processes required to generate additional images of the patient's torso.

As mentioned, the image analysis system 65 is further configured to identify a lower boundary of a patient's hanging abdominal panniculus. Similar to the above-discussion regarding the identification of other features within the image, the image analysis system 65 may be configured to utilizes differences in contrast within the image and/or other differences in color intensity within the image, as well as machine-learning based modelling to determine an approximate location and shape of a hanging abdominal panniculus. Upon detecting the lower boundary of the hanging abdominal panniculus, the image analysis system 65 is configured to identify a lowest point of the detected lower boundary of the hanging abdominal panniculus, and to generate and overlay a horizontal line tangent to this detected lowest point of the hanging abdominal panniculus (shown in a green line in the annotated view of FIG. 30).

Upon detecting a location of the pubic symphysis and a location of the lowest point of the hanging abdominal panniculus, the image analysis system 65 implements a relative-measurement based hanging abdominal panniculus criteria to classify the hanging abdominal panniculus by comparing the detected location of the pubic symphysis and a location of the lowest point of the hanging abdominal panniculus. Specifically, the relative-measurement based hanging abdominal panniculus criteria determines which of the lower edge of the hanging abdominal panniculus or the estimated location of the pubic symphysis is higher on the patient's body. Upon determining the lowest point of the hanging abdominal panniculus is below the pubic symphysis, the image analysis system 65 is configured to generate a positive diagnosis data for the hanging abdominal panniculus. Upon determining the lowest point of the hanging abdominal panniculus is above the pubic symphysis, the image analysis system 65 is configured to generate a negative diagnosis data for the hanging abdominal panniculus. The diagnosis data is assigned to be associated with the embedded image (and/or the documents/reports comprising the embedded image). The image analysis system 65 may thus generate and transmit data indicative of the resulting automatically generated diagnosis data, as well as the annotated images. Such diagnosis data may be utilized, for example, for preapproving a claim for appropriate medical treatment to address the hanging abdominal panniculus. The image analysis system 65 may transmit the generated diagnosis data to the user computing entity 30 providing the embedded image, and may provide the document/report containing the embedded image, together with the embedded image (which may be annotated, such as with a visual overlay of the posture detection line, the hanging abdominal panniculus line, and the pubic symphysis line).

As discussed in reference to the examples above, based on a determination of whether the hanging abdominal panniculus is below or above the pubic symphysis, the image analysis system 65 may route the embedded image (e.g., together with the document/report containing the embedded image) to an appropriate user computing entity 30 for final approval of a payment claim associated with the submitted document/report. For example, upon a determination that the hanging abdominal panniculus is below the pubic symphysis, the embedded image (e.g., together with the document/report containing the embedded image) may be routed to a first user computing entity 30 (e.g., operated by a nurse) for approval, and upon determining that the hanging abdominal panniculus is above the pubic symphysis, the embedded image (e.g., together with the document/report containing the embedded image) may be routed to a second user computing entity 30 (e.g., operated by a physician) for approval.

s. Breast Surgery Example

As noted above, the image analysis system 65 may be configured for executing one of a plurality of image analysis processes, which may be selected based at least in part on user input, based at least in part on detected features within an image, based at least in part on detected text within a report/document containing the image, and/or the like. In certain embodiments, the image analysis system 65 is configured for analyzing photographs of a patient's upper torso for estimation of whether the patient's bra straps have created an indention within the patient's shoulders, which may be utilized as a proxy for a determination that the patient's breasts are sufficiently heavy to justify breast surgery.

As discussed in reference to the various examples provided above, the image analysis system 65 may first extract images provided for analysis, and to determine whether the images are of sufficient quality and content to enable a determination of whether the patient's shoulders are indented from the patient's bra straps. The image analysis system 65 may be configured to implement a pre-processing and image quality check process analogous to that discussed in reference to other photograph-based examples discussed above.

After extracting images from a containing document (e.g., utilizing an edge detection algorithm based on a detected difference in color intensity between a generally white background of a document and a colored background of a photograph), the image analysis system 65 may be configured to determine whether the photograph is of a sufficient size (e.g., in pixels) to enable an accurate assessment of whether the patient's shoulders are indented from the patient's bra strap. Moreover, as discussed above, the image analysis system 65 may perform one or more image editing processes, such as image rotation, image sharpening, and/or the like to enable a more accurate assessment of the patient's shoulders to determine whether the patient's shoulders are indented. However, it should be understood that certain image analysis processes, including feature detection processes as discussed herein, may be orientation agnostic, so as to be able to perform appropriate image analysis regardless of the orientation of the extracted image.

FIGS. 31A-31B illustrate examples of image pre-processing filters that may be applied to extracted images to ensure that images are of sufficient quality and content to enable a determination of whether the patient's shoulders are indented. It should be noted that certain embodiments may be utilize any detected features within a patient's breasts (not fully shown in FIGS. 31A-31B) visible within uncensored images to assist in determining whether the images are of sufficient size, quality, and/or content for classification and further analysis. Specifically, FIG. 31A illustrates an example image deemed unacceptable for further analysis, and such images are discarded as a result of the image preprocessing processes. With reference to FIG. 31A specifically, images of a patient's back may be excluded as failing to show the appropriate content of the image to enable an analysis thereof. Other images deemed unacceptable for further analysis may comprise images containing only text as they do not provide any images that can be analyzed. Substandard quality images may also be excluded from further analysis, as such images cannot be utilized to reliably locate specific features within an image. Black-and-white or greyscale images may also be excluded, as such images may not provide adequate contrast between features that would enable an analysis thereof. Images containing a plurality of sub-images (e.g., of different orientations) may also be excluded as not containing any image of adequate size for further analysis. Side view images, lateral view images, oblique images, or images of a patient's upper torso from perspectives other than a straight frontal view may also be excluded as an accurate assessment of the patient's shoulders cannot be completed. Cropped images of the patient's shoulders only may also be excluded, as such photos do not provide a complete overview of the patient's breast characteristics to determine whether breast surgery is warranted. As yet another example, straight frontal images of the patient's upper torso, but having the patient's shoulders obscured (e.g., by the patient's hair) may be excluded, as such images do not enable an accurate assessment of indentions of the patient's shoulders. It should be understood that a machine-learning based preprocessing methodology as discussed herein may be utilized to recognize and exclude such images from further analysis. By contrast, FIG. 31B shows example straight frontal images in sufficient color, quality, size, and content (e.g., having visible shoulders) that may be further analyzed.

Once the image analysis system 65 has determined that the image is of sufficient size, quality, and content to enable an assessment of whether the patient's shoulders have been indented by the patient's bra straps, the image analysis system 65 may utilize one or more machine-learning based models (e.g., classification models) for determining whether the content of the extracted image contains images of the patient's upper torso with sufficient clarity, content, and orientation so as to enable an accurate assessment of the patient's shoulders so as to be able to determine whether the patient's shoulders are indented by the patient's bra straps. As just one example, the image analysis system 65 may utilize a convolutional neural network to compare the contents of the extracted images with an image training set to determine whether the extracted images match images within the training set that are deemed sufficient to enable a desired analysis of the patient's shoulders. For example, the classification model may be configured to determine whether a sufficient proportion of the patient's upper torso is shown in the photograph, extending from the patient's upper neck/chin and below a patient's breasts. By identifying certain features and relationships between those certain features, the image analysis system 65 is configured to determine whether the image is of a proper content and orientation to enable further analysis.

Figure 32B:
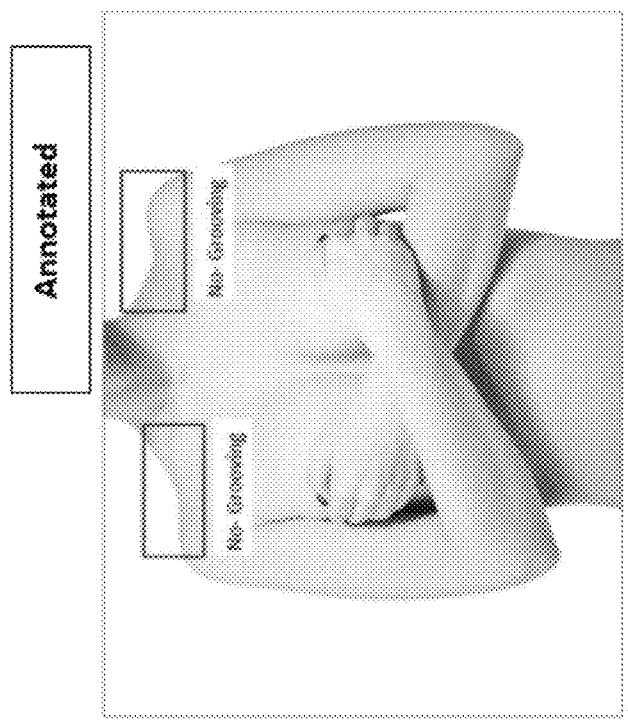
Figure 32A:
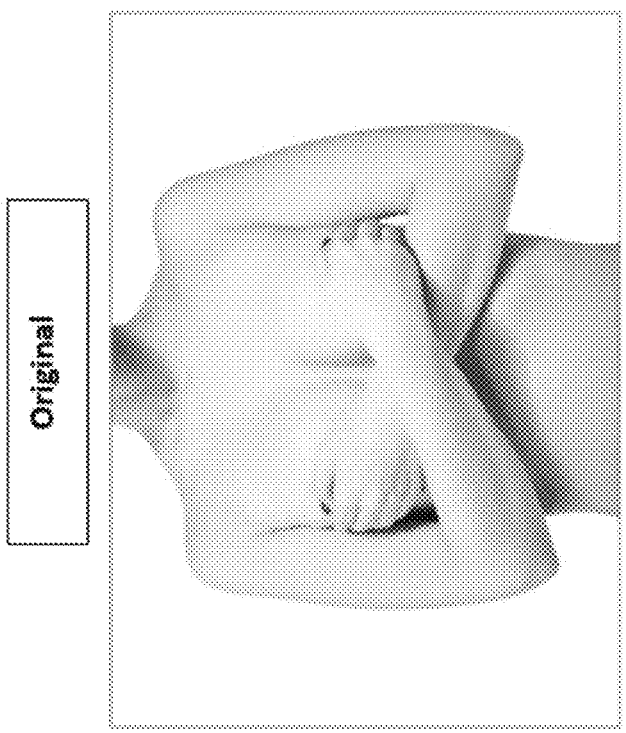

FIGS. 32A-32B illustrate example original and annotated graphical output of images for analyzing a patient's breast weight by reviewing the patient's shoulders for bra strap indentions. Again, it should be understood that the image analysis system 65 may utilize features otherwise unshown in the images of FIGS. 32A-32B (e.g., the location of the patient's nipple) as a part of the machine-learning modelling and/or training of those machine-learning models.

Once the image analysis system 65 determines that an image is sufficient for assessing the patient's shoulders for indentions (such as in an image of FIG. 32A), the image analysis system 65 may utilize a machine-learning based model for identifying a specific region of interest within the image as including the patient's shoulders (as outlined in the red rectangles shown in FIG. 32B). The region of interest may be identified as extending from an edge of the patient's neck to a point where the downward slope of the patient's shoulders exceeds a defined maximum downward slope (where the patient's shoulders slope into the patient's arms). Within the identified region of interest, the image analysis system 65 applies a relative-measurement based machine learning model to classify the embedded image by detecting indentions in the patient's shoulders, such as by detecting sudden and short changes in slope in a detected edge of the patient's shoulders. In certain embodiments, the image analysis system 65 is configured to utilize a binary determination of whether indentions are identified or not. In other embodiments, the image analysis system 65 is configured to utilize a threshold-based determination of characteristics of those indentions, such as by determining whether the indentions are present or not, and if the indentions are present, are they shallow or deep indentions. The distinction between shallow and deep indentions may be based at least in part a threshold (e.g., a pixel-based threshold) automatically established by a machine-learning based model trained utilizing labelled training data distinguishing between shallow and deep indentions. The provided images may not have any features that can be utilized to establish an absolute measurement scale, and accordingly distinctions between shallow and deep indentions are determined based on relative differences between the depth of an indention and the size of other detected features within the image.

Based on detected indentions within the patient's shoulders (or absence of indentions in the patient's shoulders), the image analysis system 65 implements a breast surgery criteria, which may specify that an indention should be present or an indention should be classified as a deep indention to be assigned positive diagnosis data for the patient's breast characteristics. Upon determining the patient's shoulders are not indented (or for certain breast surgery criteria, the patient's shoulders have shallow indentions), the image analysis system 65 is configured to generate negative diagnosis data for the patient's breast characteristics. The diagnosis data is assigned to be associated with the embedded image (and/or the documents/reports comprising the embedded image). The image analysis system 65 may thus generate and transmit data indicative of the resulting automatically generated diagnosis data, as well as the annotated images. Such diagnosis data may be utilized, for example, for preapproving a claim for breast surgery. The image analysis system 65 may transmit the generated diagnosis data to the user computing entity 30 providing the embedded image, and may provide the document/report containing the embedded image together with the embedded image (which may be annotated, such as with a visual overlaid box around the region of interest of the patient's shoulders).

As discussed in reference to the examples above, based on a determination of whether the patient's shoulders have indentions satisfying applicable breast surgery criteria, the image analysis system 65 may route the embedded image (e.g., together with the document/report containing the embedded image) to an appropriate user computing entity 30 for final approval of a payment claim associated with the submitted document/report. For example, upon a determination that the patient's shoulders are indented sufficiently to satisfy breast surgery criteria, the embedded image (e.g., together with the document report containing the embedded image) may be routed to a first user computing entity 30 (e.g., operated by a nurse) for approval, and upon determining that the patient's shoulders are not indented sufficiently to satisfy breast surgery criteria, the embedded image (e.g., together with the document/report containing the embedded image) may be routed to a second user computing entity 30 (e.g., operated by a physician) for approval.

t. Rhinoplasty Example

As noted above, the image analysis system 65 may be configured for executing one of a plurality of image analysis processes, which may be selected based at least in part on user input, based at least in part on detected features within an image, and/or the like. In certain embodiments, the image analysis system 65 is configured for analyzing photographs of a patient's face for determining whether the patient's nose is sufficiently misaligned as to require a rhinoplasty procedure.

As discussed in reference to the various examples provided above, the image analysis system 65 may first extract images provided for analysis, and to determine whether the images are of sufficient quality and content to enable a determination of whether the patient's nose is misaligned. The image analysis system 65 may be configured to implement a pre-processing and image quality check process analogous to that discussed in reference to other photograph-based examples discussed above.

After extracting images from a containing document (e.g., utilizing an edge detection algorithm based on a detected difference in color intensity between a generally white background of a document and a colored background of a photograph), the image analysis system 65 may be configured to determine whether the photograph is of a sufficient size (e.g., in pixels) to enable an accurate assessment of characteristics of the patient's nose (e.g., shape, size, location, orientation, and/or the like). Moreover, as discussed above, the image analysis system 65 may perform one or more image editing processes, such as image rotation, image sharpening, and/or the like to enable a more accurate assessment of the patient's nose to ascertain various characteristics of the patient's nose. However, it should be understood that certain image analysis processes, including feature detection processes as discussed herein, may be orientation agnostic, so as to be able to perform appropriate image analysis regardless of the orientation of the extracted image.

Once the image analysis system 65 has determined that the image is of sufficient size and quality to enable a detection of various characteristics of the patient's nose (including orientation relative to other portions of the patient's face), and upon determining that the image is of sufficient orientation to enable a desired comparison between the location of portions of the patient's nose and other portions of the patient's face, the image analysis system 65 may utilize one or more machine-learning based models (e.g., classification models) for determining whether the content of the extracted image contains images of the patient's face with sufficient clarity, content, and orientation so as to enable an accurate assessment of characteristics of the patient's nose. As just one example, the image analysis system 65 may utilize a convolutional neural network to compare the contents of the extracted images with an image training set to determine whether the extracted images match images within the training set that are deemed sufficient to enable a desired analysis of the patient's face and nose. For example, the classification model may be configured to determine whether the entirety of the patient's head and neck are shown within the photograph. By identifying certain features and relationships between those certain features, the image analysis system 65 is configured to determine whether the image is of a proper content and orientation to enable further analysis.

Figure 33:
FIGS. 33-34B illustrate example facial images for classifying images relating to rhinoplasty requirements according to certain embodiments.
Figure 34A:
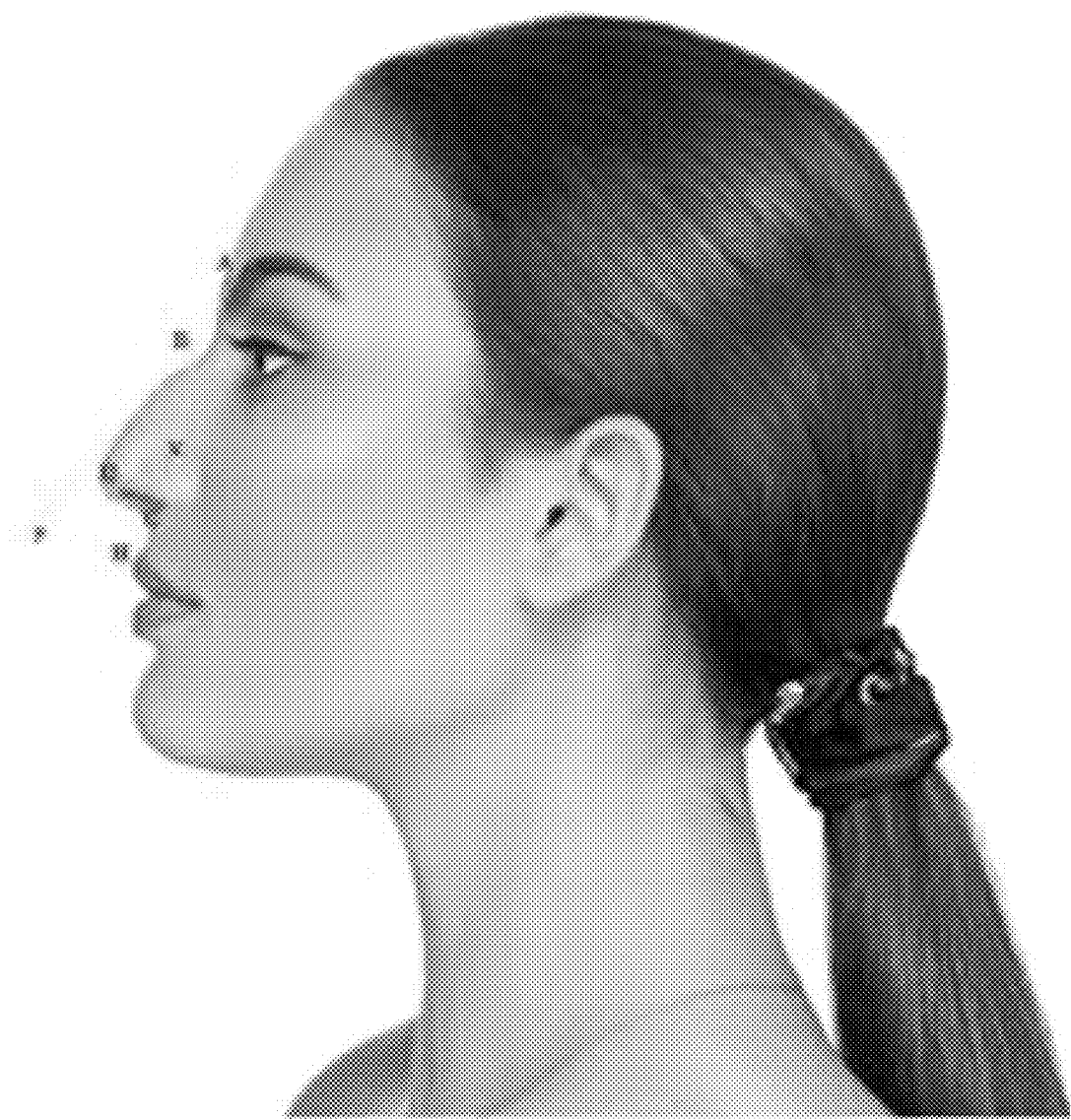
Figure 34B:
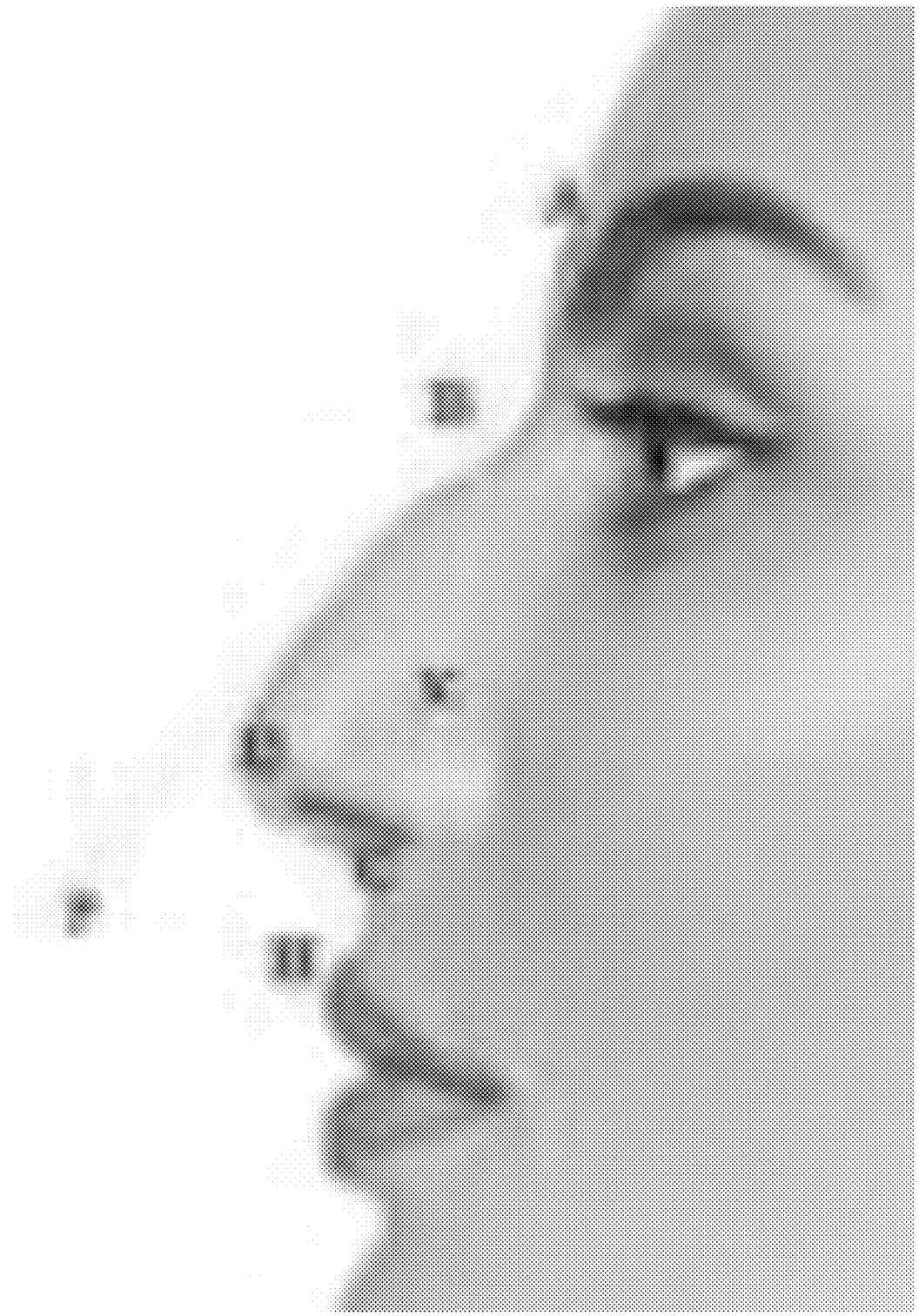

FIGS. 33-34B illustrate input images and corresponding graphical output resulting from an example analysis of a patient's face. As is evidence from the figures, FIG. 33 illustrates an analysis conducted on a frontal view of the patient's face (for determining whether any misalignment of the patient's nose is evident from the frontal view) and FIGS. 34A-34B illustrate an example input image overlaid with graphical output for a side-view analysis of a patient's face (for determining whether any misalignment of the patient's nose is evident from the side view), with FIG. 34B being a closeup of FIG. 34A. Each of these analyses may be conducted utilizing relative measurement-based criteria for classifying features of the patient's nose. However it should be understood that one or more of these analyses, such as the frontal view analysis, may be performed at least partially utilizing one or more absolute measurements, as a patient's irises may be utilized as a reference feature for establishing a scale for absolute measurements within the image. Once the image analysis system 65 determines that an image is sufficient for analyzing characteristics of the patient's nose, the image analysis system 65 may utilize a machine-learning based model for identifying specific features within the image, such as the patient's irises (e.g., utilizing one or more methods for identifying a patient's irises as discussed in the Blepharoptosis example above), the patient's mouth, a left-most edge of the patient's nose, a right-most edge of the patient's nose, a tip of the patient's nose, and/or the like. Any of a variety of methodologies may be utilized for identifying boundaries of the various identified features. Certain embodiments may execute processes for identifying boundaries of the identified features without further image manipulation. In other embodiments, the image analysis system 65 may utilize image manipulation (e.g., changing image contrast) to emphasize feature boundaries, so as to identify precise locations of boundaries of specific features.

To identify the approximate location of various aspects of the patient's nose and to determine an alignment of the patient's nose relative to other aspects of the patient's face, the image analysis system 65 utilizes machine-learning based modelling to identify and establish a set of reference lines within the patient's face, relative to the patient's eyes and mouth. Specifically, the image analysis system 65 identifies a first horizontal reference line between identified center-points of the patient's irises (this horizontal reference line is visible in yellow within FIG. 33 extending between the patient's irises. A second, vertical reference line is additionally established, extending from a center of the horizontal reference line to an identified center-point of the patient's mouth (the patient's mouth being identified utilizing a machine-learning based classification model). This vertical reference line is visible within FIG. 33.

The image analysis system 65 additionally identifies a top-most point of the patient's nose (identified as the intersection between the first reference line and the second reference line), a tip of the patient's nose (identified through machine-learning based analysis for recognizing and identifying the tip of the patient's nose), a left-most edge of the patient's nose and a right-most edge of the patient's nose. The image analysis system 65 draws two triangles relative to these points. The triangles extend between the identified top-most point to the identified left most point (for a first triangle) and to the identified right most point (for a second triangle), and from the identified left/right most point to the tip of the patient's nose, and from the tip of the patient's nose to the top-most point of the patient's nose. The image analysis system 65 may additionally measure (e.g., in pixels or in absolute measurements, utilizing the size of the patient's irises to provide a reference scale for the image) each side-length of the generated triangles. In certain embodiments, the image analysis system 65 may additionally measure an angle between the vertical reference line and the line extending between the tip of the patient's nose to the top-most point of the patient's nose.

Utilizing a machine-learning model, the image analysis system 65 executes a relative-measurement based analysis of the embedded image and determines a ratio between triangle side-lengths of a left triangle and a right triangle (e.g., determining a ratio of lengths between the top-most point and the left-most point of the patient's nose; and between the top-most point and the right-most point of the patient's nose) so as to estimate the symmetry of the patient's nose and to thereby classify the patient's nose as symmetrical or asymmetrical.

For side-view images, the image analysis system 65 identifies and generates reference lines between various portions of the patient's face and nose. As visible specifically in FIGS. 34A and 34B (FIG. 34B being a close-up view of a relevant portion of FIG. 34A), a first reference line is drawn tracing the outermost edge of the patient's nose to a detected location of the bridge of the patient's nose, and upward from the bridge of the patient's nose along a portion of the patient's forehead. A second reference line extends vertically downward from the corner of the first reference line, at the detected bridge of the patient's nose. A third reference line extends vertically upward from an upper edge of the patient's mouth to a lowermost edge of the patient's nose, and from the lowermost edge of the patient's nose to the tip of the patient's nose. Utilizing these reference lines, the machine-learning model generates one or more measurements (e.g., in pixels) indicating the extent to which certain portions of the patient's nose crosses these reference lines, or does not directly track the reference lines. In other words, the image analysis system 65 identifies areas of the patient's nose that deviate from corresponding reference lines.

Upon identifying and generating reference lines within the embedded images, the image analysis system 65 implements rhinoplasty criteria to classify the image and to thereby determine whether the embedded images (and the automatically generated measurements associated therewith) are indicative of a need for a rhinoplasty procedure. For example, the rhinoplasty criteria may examine a frontal view of the patient's face to determine whether the patient's nose is sufficiently asymmetrical as to require a rhinoplasty procedure. A determination of sufficient asymmetry may be performed by comparing ratios of measurements on the left and right sides of the patient's nose relative to a symmetry threshold, and if the ratio satisfies the symmetry threshold (e.g., being below or above the symmetry threshold, depending on the configuration), the image analysis system 65 generates a positive diagnosis data for the rhinoplasty procedure. As a specific example, if the distance measured between the top-most point and the left-most point of the patient's nose is drastically different from the distance measured between the top-most point and the right-most point of the patient's nose (the distances measured in pixels, for example), the generated ratio between these measurements may exceed a symmetry threshold, thereby causing the image analysis system 65 to generate the positive diagnosis data to be associated with the embedded image (and/or the document/report containing the embedded image). The rhinoplasty criteria may additionally implement a plurality of additional criteria. For example, symmetry thresholds may be established for multiple measurements to be performed on opposing sides of the patient's nose (e.g., length measurements, angle measurements between intersecting lines drawn onto the patient's nose, and/or the like). Orientation thresholds may additionally be implemented as comparing an angle between the vertical reference line and the line extending between the top-most point of the patient's nose to the tip of the patient's nose. The orientation threshold in such an instance may be implemented as an angle threshold, with an angle exceeding the angle threshold being indicative of a needed rhinoplasty procedure and a positive diagnosis data to be associated with the embedded image.

For side view analyses, the rhinoplasty criteria may specify a threshold distance between a detected edge of the patient's nose and a generated reference line to be associated with the patient's nose. The threshold distance in such criteria may be representative of a convex or concave feature on the patient's nose that drastically extends beyond an expected boundary of the nose (the expected boundary being represented by the reference line) or that is drastically inset relative to the expected boundary of the nose. As such differences between a detected boundary of a nose and an expected boundary of a nose may result in difficulty breathing for the patient (e.g., based on relatively closed nasal passage), detections of differences between the expected and actual boundaries of the patient's nose may be utilized for generation of positive diagnosis data indicative of a needed rhinoplasty procedure to be associated with the embedded image.

In the event that none of the rhinoplasty criteria are satisfied, the image analysis system 65 may be configured to generate negative diagnosis data for the rhinoplasty procedure. The diagnosis data (whether positive diagnosis data or negative diagnosis data) is assigned to be associated with the embedded image (and/or the documents/reports comprising the embedded image). The image analysis system 65 may thus generate and transmit data indicative of the resulting automatically generated diagnosis data, as well as the annotated images. Such diagnosis data may be utilized, for example, for preapproving a claim for a rhinoplasty procedure. The image analysis system 65 may transmit the generated diagnosis data to the user computing entity 30 providing the embedded image, and may provide the document/report containing the embedded image, together with the embedded image (which may be annotated, such as with a visual overlay of the reference lines and/or lines bounding the patient's nose).

As discussed in reference to the examples above, based on a determination of whether the images satisfy one or more rhinoplasty criteria, the image analysis system 65 may route the embedded image (e.g., together with the document/report containing the embedded image) to an appropriate user computing entity 30 for final approval of a payment claim associated with the submitted document/report. For example, upon a determination that the patient's nose satisfies one or more rhinoplasty criteria, the embedded image (e.g., together with the document/report containing the embedded image) may be routed to a first user computing entity 30 (e.g., operated by a nurse) for approval, and upon determining that the patient's nose does not satisfy any of the rhinoplasty criteria, the embedded image (e.g., together with the document/report containing the embedded image) may be routed to a second user computing entity (e.g., operated by a physician) for approval.

IV. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

For example, it should be understood that other healthcare conditions may be automatically diagnosed in accordance with example configurations as discussed herein, such as through machine-learning based configurations for detecting individual features within images and determining whether those features (or relationships between various features) are indicative of particular diagnoses. Such configurations may be utilized for automatic determinations of whether medical claims submitted to a payor meet applicable criteria for approval, so as to increase the speed at which healthcare providers receive payment for services provided to patients, and/or to increase the speed at which patients receive approval for seeking particular specialized medical care selected based at least in part on diagnoses provided to a patient.

Other embodiments are configured for providing classification methodologies analogous to those discussed herein in other contexts outside of the medical field. Such embodiments may be utilized for diagnosing mechanical issues with machinery based on visual inspections, determining whether a particular machine includes all appropriate components, detecting architectural problems with a building design, and/or the like. It should be understood that embodiments may be usable in any of a variety of contexts so as to provide classification and/or diagnoses processes based on image analyses as discussed herein.

That which is claimed:

1. A system comprising:
    memory; and one or more processors communicatively coupled to the memory, the one or more processors configured to:
        receive an image comprising image content and associated metadata for a patient;
        identify diagnosis criteria comprising at least one feature identification model;
        apply the at least one feature identification model to the image content to identify a first feature and a second feature specified by the identified diagnosis criteria within the image content;
        determine orientation information of the first feature and the second feature within the image content;
        determine a positioning of the first feature and the second feature;
        determine a location of the first feature relative to the second feature within the image content based at least in part on the orientation information of the first feature and the second feature and the positioning of the first feature and the second feature; and
        determine a diagnosis for the patient based at least in part on the diagnosis criteria and the location of the first feature relative to the second feature.

2. The system of claim 1, wherein to determine the location of the first feature relative to the second feature, the one or more processors are configured to determine an angle between the first feature and the second feature.

3. The system of claim 1, wherein to determine the location of the first feature relative to the second feature, the one or more processors are configured to determine a distance between portions of the first feature and the second feature, and wherein the distance is a percentage of a size of either the first feature or the second feature.

4. The system of claim 1, wherein the at least one feature identification model comprises a supervised machine-learning feature identification model configured to:
    identify the first feature and the second feature; and
    determine a classification of one or more of the first feature or the second feature; and
    wherein to determine the diagnosis for the patient, the one or more processors are configured to determine image characteristics based at least in part on the classification of the one or more of the first feature or the second feature.

5. The system of claim 4, wherein to determine the classification of the one or more of the first feature or the second feature, the one or more processors are configured to classify a skin lesion, and wherein the at least one feature identification model comprises a convolutional neural network.

6. The system of claim 4, wherein to determine the classification of the one or more of the first feature or the second feature, the one or more processors are configured to classify a breast mass within a mammograph, and wherein the supervised machine-learning feature identification model comprises a convolutional neural network.

7. The system of claim 4, wherein the one or more of the first feature and the second feature represent one or more vertebrae, and wherein to determine the classification of the one or more of the first feature or the second feature, the one or more processors are configured to determine a ratio between measurements of the one or more vertebrae.

8. The system of claim 4, wherein the one or more of the first feature or the second feature comprise a pubic symphysis and a lower edge of a hanging abdominal panniculus, and wherein to determine the classification of the one or more of the first feature or the second feature, the one or more processors are configured to compare a location of the pubic symphysis relative to a location of the lower edge of a hanging abdominal panniculus.

9. The system of claim 4, wherein to determine the classification of the one or more of the first feature or the second feature, the one or more processors are configured to detect an indention within an image of a patient's shoulder.

10. The system of claim 4, wherein to determine the classification of the one or more of the first feature or the second feature, the one or more processors are configured to detect a symmetry of a detected nose.

11. A computer-implemented method comprising:
    receiving, by one or more processors, an image comprising image content and associated metadata for a patient;
    identifying, by the one or more processors, diagnosis criteria comprising at least one feature identification model;
    applying, by the one or more processors, the at least one feature identification model to the image content to identify a first feature and a second feature specified by the identified diagnosis criteria within the image content;
    determining, by the one or more processors, orientation information of the first feature and the second feature within the image content;
    determining, by the one or more processors, a positioning of the first feature and the second feature;
    determining, by the one or more processors, a location of the first feature relative to the second feature within the image content based at least in part on the orientation information of the first feature and the second feature and the positioning of the first feature and the second feature; and
    determining, by the one or more processors, a diagnosis for the patient based at least in part on the diagnosis criteria, and the location of the first feature relative to the second feature.

12. The computer-implemented method of claim 11, wherein determining the location of the first feature relative to the second feature comprises determining an angle between the first feature and the second feature.

13. The computer-implemented method of claim 11, wherein determining the location of the first feature and the second feature comprises determining a distance between portions of the first feature and the second feature, and wherein the distance is a percentage of a size of either the first feature or the second feature.

14. The computer-implemented method of claim 11, wherein the at least one feature identification model comprises a supervised machine-learning feature identification model for:
   identifying the first feature and the second feature; and
   determining a classification of one or more of the first feature or the second feature; and
   wherein determining the diagnosis for the patient comprises determining image characteristics based at least in part on the classification of the one or more of the first feature or the second feature.

15. The computer-implemented method of claim 14, wherein determining the classification of the one or more of the first feature or the second feature comprises classifying a skin lesion, and wherein the at least one feature identification model comprises a convolutional neural network.

16. The computer-implemented method of claim 14, wherein determining the classification of the one or more of the first feature or the second feature comprises classifying a breast mass within a mammograph, and wherein the supervised machine-learning feature identification model comprises a convolutional neural network.

17. One or more non-transitory computer-readable storage media including instructions that, when executed by one or more processors, cause the one or more processors to:
   receive an image comprising image content and associated metadata for a patient;
   identify diagnosis criteria comprising at least one feature identification model;
   apply the at least one feature identification model to the image content to identify a first feature and a second feature specified by the identified diagnosis criteria within the image content;
   determine orientation information of the first feature and the second feature within the image content;
   determine a positioning of the first feature and the second feature;
   determine a location of the first feature relative to the second feature within the image content based at least in part on the orientation information of the first feature and the second feature and the positioning of the first feature and the second feature; and
   determine a diagnosis for the patient based at least in part on the diagnosis criteria and the location of the first feature relative to the second feature.

18. The one or more non-transitory computer-readable storage media of claim 17, wherein to determine the location of the first feature relative to the second feature, the instructions further cause the one or more processors to determine an angle between the first feature and the second feature.

19. The one or more non-transitory computer-readable storage media of claim 17, wherein to determine the location of the first feature relative to the second feature, the instructions further cause the one or more processors to determine a distance between portions of the first feature and the second feature, and wherein the distance is a percentage of a size of either the first feature or the second feature.

20. The one or more non-transitory computer-readable storage media of claim 17, wherein the at least one feature identification model comprises a supervised machine-learning feature identification model configured to:
   identify the first feature and the second feature; and
   determine a classification of one or more of the first feature or the second feature; and
   wherein determining the diagnosis for the patient comprises determining image characteristics based at least in part on the classification of the one or more of the first feature or the second feature.

21. The one or more non-transitory computer-readable storage media of claim 20, wherein determining the classification of the one or more of first feature and the second feature comprises classifying a skin lesion, and wherein the at least one feature identification model comprises a convolutional neural network.

22. The one or more non-transitory computer-readable storage media of claim 20, wherein to determine the classification of the one or more of the first feature or the second feature, the instructions further cause the one or more processors to classify a breast mass within a mammograph, and wherein the supervised machine-learning feature identification model comprises a convolutional neural network.

* * * * *